(12) United States Patent
Maeng et al.

(10) Patent No.: US 8,716,309 B2
(45) Date of Patent: May 6, 2014

(54) PHARMACEUTICAL COMPOSITION COMPRISING PYRIDONE DERIVATIVES

(75) Inventors: Cheol Young Maeng, Daejeon (KR); Young Koo Jang, Daejeon (KR); Su Bong Cha, Gyeonggi-do (KR); Hye Won Shin, Daejeon (KR); Chan Mi Joung, Daejeon (KR); Hwa Ryun Cha, Gyeongsangnam-do (KR); Eun Jung Yi, Gyeonggi-do (KR)

(73) Assignee: SK Biopharmaceuticals Co., Ltd., Seoul (KR)

(*) Notice: Subject to any disclaimer, the term of this patent is extended or adjusted under 35 U.S.C. 154(b) by 0 days.

(21) Appl. No.: 13/980,819

(22) PCT Filed: Jan. 30, 2012

(86) PCT No.: PCT/KR2012/000648
§ 371 (c)(1),
(2), (4) Date: Jul. 19, 2013

(87) PCT Pub. No.: WO2012/102580
PCT Pub. Date: Aug. 2, 2012

(65) Prior Publication Data
US 2013/0317059 A1     Nov. 28, 2013

(30) Foreign Application Priority Data

Jan. 28, 2011 (KR) .................. 10-2011-0008960

(51) Int. Cl.
*A01N 43/90* (2006.01)
*A61K 31/44* (2006.01)
*C07D 453/02* (2006.01)

(52) U.S. Cl.
USPC ............................ 514/305; 546/133; 546/137

(58) Field of Classification Search
USPC .................................. 546/133, 137; 514/305
See application file for complete search history.

(56) References Cited

U.S. PATENT DOCUMENTS

| 4,404,138 A | 9/1983 | Connor et al. ............. 260/244.4 |
| 2003/0018042 A1 | 1/2003 | Eifion ............................. 514/278 |
| 2005/0020568 A1 | 1/2005 | Galli et al. ................ 514/210.21 |
| 2013/0296340 A1* | 11/2013 | Maeng et al. ............ 514/255.05 |

OTHER PUBLICATIONS

Banerjee, et al. (2000), "Cellular expression of α7 nicotinic acetylcholine receptor protein in the temporal cortex in Alzheimer's and Parkinson's disease—a stereological approach." *Neurobiol. Disease*, 7:666-672.
Bevins, et al. (2006) "Object recognition in rats and mice: a one-trial non-matching-to-sample learning task to study 'recognition memory'." *Nat Protoc.*, 1(3):1306-1311.
Bitner, et al. (2010) "In vivo pharmacological characterization of a novel selective α7 neuronal nicotinic acetylcholine receptor agonist ABT-107: preclinical considerations in Alzheimer's disease." *J. Pharmacol. Exp. Ther.*, 334:875-886.
Burghaus, et al. (2000) "Quantitative assessment of nicotinic acetylcholine receptor proteins in the cerebral cortex of Alzheimer patients." *Mol. Brain Res.*, 76:385-388.
Castner, et al. (2011) "Immediate and sustained improvements in working memory after selective stimulation of α7 nicotinic acetylcholine receptors." *Biol. Psychiatry*, 69:12-18.
Ennaceur, et al. (1988) "A new one-trial test for neurobiological studies of memory in rats.1: Behavioral data." *Behavioral Brain Res.*, 31:47-59.
Gotti, et al. (2004) "Neuronal nicotinic receptors: from structure to pathology." *Prog.Neurobiol.*, 74:363-396.
Gotti, et al. (2006) "Brain nicotinic acetylcholine receptors: native subtypes and their relevance." *Trends in Pharmacol.*, Sci. 27:482-491.
Jones, et al. (1999) "Subjective and physiological effects of intravenous nicotine and cocaine in cigarette smoking cocaine abusers[1]." *J. Pharmacol. Exp. Ther.*, 288:188-197.
Levin, et al. (2006) "Nicotinic effects on cognitive function: behavioral characterization, pharmacological specification, and anatomic localization." *Psychopharmacology*, 184:523-539.
Marrero, et al. (2009) "Convergence of alpha 7 nicotinic acetylcholine receptor-activated pathways for anti-apoptosis and anti-inflammation: central role for JAK2 activation of STAT3 and NF-κB." *Brain Res.*, 1256:1-7.
Oshikawa, et al. (2003) "Nicotinic acetylcholine receptor α7 regulates cAMP signal within lipid rafts." *Am. J. Physiol. Cell Physiol.*, 285:567-574.
Ospina, et al. (1998) "Calcium regulation of agonist binding to α7-type nicotinic acetylcholine receptors in adult and fetal rat hippocampus." *J. Neurochem.*, 70:1061-1068.
Spinelli (2006) "Enhancing effects of nicotine and impairing effects of scopolamine on distinct aspects of performance in computerized attention and working memory tasks in marmoset monkeys." *Neuropharmacology*, 51:238-250.
Wallace et al. (2011) "RG3487, a novel nicotinic α7 receptor partial agonist, improves cognition and sensorimotor gating in rodents." *J. Pharmacol. Exp. Ther.*, 336:242-253.
Woodruff-Pak, et al. (2000) "Nicotinic modulation in an animal model of a form of associative learning impaired in Alzheimer's disease." *Behav. Brain Res.*, 113:11-19.
International Search Report (ISR) in PCT/KR2012/000648, dated Jun. 21, 2012.

* cited by examiner

*Primary Examiner* — Niloofar Rahmani
(74) *Attorney, Agent, or Firm* — Harness, Dickey & Pierce, P.L.C.

(57) ABSTRACT

A pyridone derivative compound and a pharmaceutically acceptable salt, isomer, solvate or hydrate thereof, and a preventive or therapeutic pharmaceutical composition for cognitive disorders that includes the pyridone derivative compound or a pharmaceutically acceptable salt, isomer, solvate or hydrate thereof.

13 Claims, No Drawings

PHARMACEUTICAL COMPOSITION COMPRISING PYRIDONE DERIVATIVES

CROSS-REFERENCE TO RELATED APPLICATIONS

This application is a national phase application of PCT Application No. PCT/KR2012/000648, filed on Jan. 30, 2012, which claims the benefit and priority to Korean Patent Application No. 10-2011-0008960, filed Jan. 28, 2011. The entire disclosures of the applications identified in this paragraph are incorporated herein by references.

TECHNICAL FIELD

The present invention relates to an azabicycloalkane-substituted pyridone derivative compound as an agonist or partial agonist of α 7-nicotinic acetylcholine receptor (nAChR), and a pharmaceutically acceptable salt, isomer, solvate or hydrate thereof.

BACKGROUND ART

Nicotinic acetylcholine receptors (nAChR), which are of a ligand-gated ion channel family, are prevalent in the central nervous system (CNS) and peripheral nervous system (PNS), and are involved in a variety of physiological functions. These receptors serve as important factors in controlling the CNS's physiological functions via controlling the release of a variety of neurotransmitters, such as acetylcholine, norepinephrine, dopamine, serotonin, and gamma-aminobutyric acid (GABA). Therefore, with the control of such neurotransmitters and the cellular signal transfer system, AChR may be used in treating diseases associated with cognitive function, learning and memory, neurodegeneration, pain and inflammation, neuropsychosis and mood disorder, and compulsive and addictive behaviors, controlling and treating inflammation or inflammatory diseases, and in relieving pains.

Diverse nAChR subtypes are present in the CNS and PNS. Typically, nAChR are ionic channels able to selectively transmit diverse cations with five monomers surrounding a central ion conducting pore of the ionic channel. In humans, at least 12 monomers, α2~α10, and β2~β4 are expressed, where these monomers form diverse homomeric or heteromeric complexes through combination with each other. Heteromeric α4β2 nAChR with high binding affinity to nicotin and homomeric α7 nAChR with low affinity to nicotin are known to be main expressions in the CNS [Gotti C, Zoli M, Clementi F (2006) Trends in Pharmacol. Sci. 27; 482-491].

Nicotinic α7 receptors, which are expressed in the cerebral cortex and hippocampus that are responsible for brain's cognitive and sensory functions are found both in presynaptic and postsynaptic terminals, and thus, have been suggested as a significant factor in synaptic pass [Burghaus L, Schutz U, Krempel U, de Vos R A I, Jansen Steur E N H, Wevers A, Lindstrom J, Schroder H (2000), Mol. Brain. Res. 76; 385-388; Banerjee C, Nyengaard R J, Wevers A, de Vos R A I, Jansen Steur E N H, Lindstrom J, Pilz K, Nowacki S, Bloch W, Schroder H (2000), Neurobiol. Disease, 7; 666-672]. Nicotinic α7 receptors are inherently highly permeable to calcium ions, and thus, have been proposed as a significant factor in diverse calcium-dependent neurotransmission systems [Oshikawa J, Toya Y, Fujita T, Egawa M, Kawabe J, Umemura S, Ishikawa Y (2003) Am. J. Physiol. Cell Physiol. 285; 567-574; Marrero M B, Bencherif M (2009) Brain Res. 1256; 1-7; Ospina J A, Broide R S, Acevedo D, Robertson R T, Leslie F M (1998) J. Neurochem. 70; 1061-1068].

Since nicotinic acetylcholine receptors are involved in the control of various cerebral functions, including cognitive function and attentiveness, substances that are able to directly or indirectly activate such nicotinic acetylcholine receptors are expected to be ultimately beneficial in relieving cognitive impairments, such as Alzheimer type dementia, schizophrenia associated cognitive disorders, and attention deficit such as attention deficit hyperactivity disorder (ADHD) [Levin E D, McClernon F J, Rezvani A H (2006) Psychopharmacology 184; 523-539].

DISCLOSURE OF INVENTION

Technical Problem

The present invention provides an azabicycloalkane-substituted pyridone derivative compound as an agonist or partial agonist of α7-nicotinic acetylcholine receptor (nAChR), and a pharmaceutically acceptable salt, isomer, solvate, or hydrate thereof.

Solution to Problem

According to aspects of the present invention, there are provided a pyridone derivative compound represented by Formula I or Formula II below, and a pharmaceutically acceptable salt, isomer, solvate, or hydrate thereof, wherein in Formulae I and II, A is a C6-C12 aryl group substitutable with at least one selected from the group consisting of a halo group, an amino group, a C1-C6 alkyl group, a C2-C6 alkynyl group, a C3-C7 cycloalkyl group, a C1-C6 alkoxy group, a C6-C12 aralkoxy group, a C6-C12 aryloxy group, a C1-C6 alkylthio group, a C6-C12 aralkylthio group, a C6-C12 arylthio group, a C1-C6 alkylsulfonyl group, and a C2-C10 heteroaryl group; and B is O or NH.

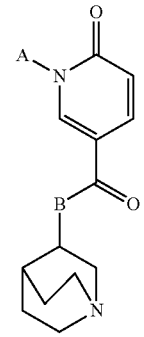

Formula I

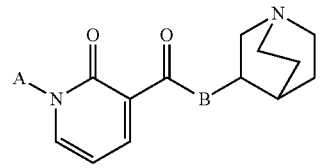

Formula II

The term "aryl" used herein refers to an aromatic carbocyclic system with at least one ring, wherein the rings may be linked together by condensation such as naphthyl or by a pendant method such as biphenyl. At least one hydrogen atom in the aryl group may be substituted with, for example, a halogen atom, an alkyl group, or an alkoxy group.

The term "heteroaryl group" used herein refers to a system with at least one aromatic ring that includes at least one heteroatom selected from among N, O, and P, and of which the rest of the rings is carbon, such as thiazole, thienyl, or the like. The rings may be fused with or linked by a single bond with one or two phenyl rings and/or an additional hetero ring, such as benzothiazole. At least one hydrogen atom in the heteroaryl group may be substituted with, for example, a halogen atom, an alkyl group, or an alkoxy group.

Non-limiting examples of C6-C12 aryloxy groups used herein are phenyloxy, naphthyloxy, and biphenyloxy. At least one hydrogen atom in the aryloxy group may be substituted with a substituent such as a halogen atom or an alkyl group.

Non-limiting examples of the C6-C12 aralkoxy group used herein are phenylmethoxy and phenylethoxy. At least one hydrogen atom in the C6-C12 aralkoxy group may be substituted with a substituent such as a halogen atom or an alkyl group.

Non-limiting examples of the C6-C12 aralkylthio group are phenylmethylthio and phenylethylthio.

In some embodiments, B in Formula I and II may be NH, and the C6-C12 aryl group may be phenyl, biphenyl, or naphthyl.

In some embodiments, the azabicyclo aryl-substituted pyridone derivative compound of Formula I or Formula II may be prepared from any known compound or any compound readily obtainable therefrom by one of ordinary skill in the art. Therefore, the following descriptions associated with methods of preparing the pyridone derivative compound are provided only for illustrative purposes, and are not intended to limit the scope of the present invention. For example, the order of unit operations may be changed if needed.

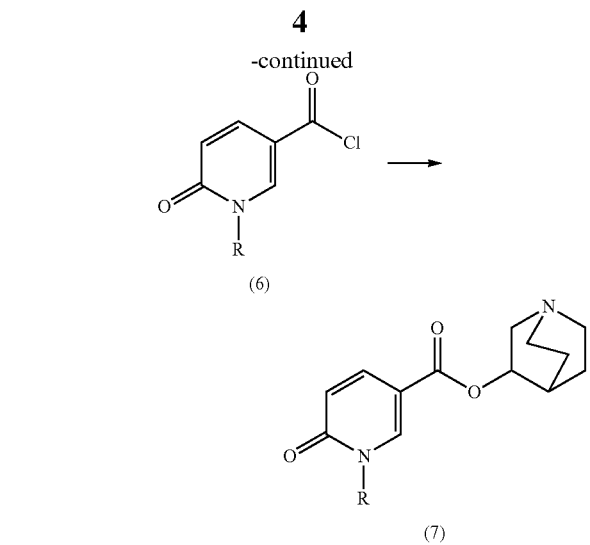

In the scheme illustrated above, R may be an aryl group. After synthesis of 6-oxo-3-carbonylchloride from 6-pyridone-3-carboxylic acid, a final compound 7 may be obtained via introduction of quinuclidinol.

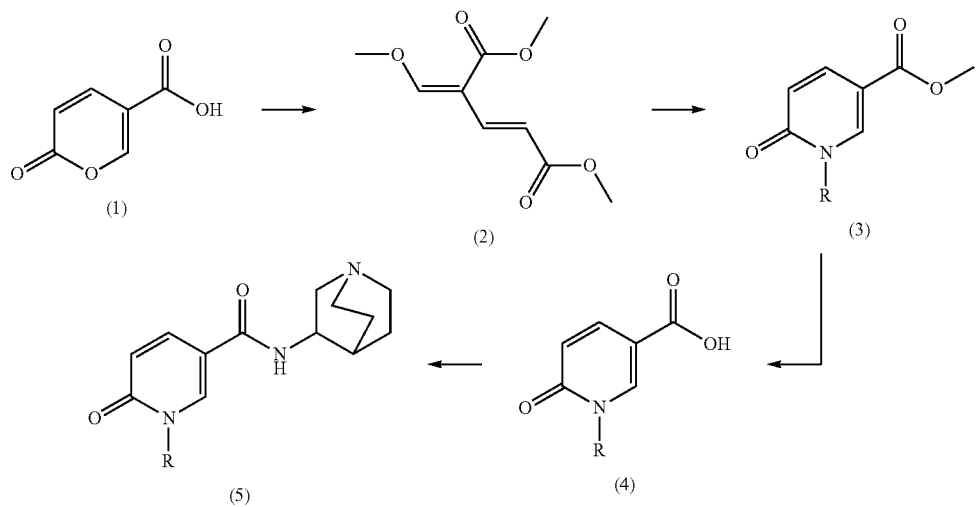

In the scheme illustrated above, R may be an aryl group. In a general synthesis method illustrated in the above scheme, after synthesis of an intermediate 2 from a coumarilic acid 1 as a starting material, the intermediate 2 may react with an amino heteroaryl compound and dimethylformamide (DMF) at about 150° C. to obtain a 6-pyridone compound 3, which may be then hydrolyzed into 6-pyridone-3-carboxyl acid 4, and then a final compound 5 may be obtained via introduction of quinuclidine.

Scheme 2: Synthesis of pyridone derivative

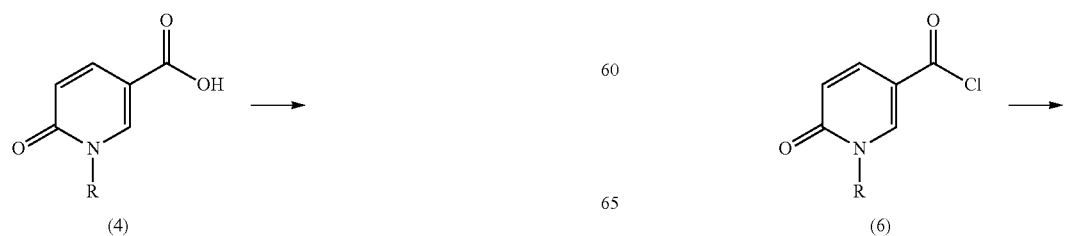

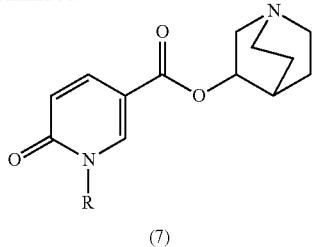

(7)

In the scheme illustrated above, R may be an aryl group. After 2-oxo-1-aryl-1,2-dihydro-pyridine-3-carboxylic acid methyl ester is synthesized from 2-oxo-1,2-dihydro-pyridine-3-carboxylic acid methyl ester and is then hydrolyzed into carboxylic acid, a final compound II may be obtained via introduction of quinuclidine.

Examples of the pyridine derivative are the compounds represented by Formula I or Formula II, pharmaceutically acceptable salts, such as additional acid or base salts, and any stereochemical isomer thereof, wherein these salts are not specifically limited and may be any salt that is able to retain activity of a parent compound thereof in a target subject and does not cause any undesirable effect. Examples of these salts are both inorganic and organic salts, such as acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene-sulfonic acid, benzoic acid, stearic acid, cresylic acid, lactic acid, bicarbonic acid, bisulfuric acid, bitartaric acid, oxalic acid, butylic acid, calcium edatate, camsylic acid, carbonic acid, chlorobenzoic acid, citric acid, edetic acid, toluenesulfonic acid, edicylinic acid, ecylinic acid, fumaric acid, gluceptic acid, pamoic acid, gluconic acid, glycollarsanylic acid, methyl nitrate, polygalactronic acid, hexyllisorcynonic acid, malonic acid, hydrobamic acid, hydrochlorinic acid, hydroiodic acid, hydroxy-naphtholic acid, isethionic acid, lactobionic acid, mandelic acid, estolinic acid, mucic acid, muconic acid, p-nitromethanesulfonic acid, hexamic acid, phantothenic acid, monohydrogen phosphoric acid, dihydrogen phosphoric acid, salicylic acid, sulfamine acid, sulfanilic acid, methanesulfonic acid, and theoclic acid. Examples of a basic salt are an ammonium salt, a salt of an alkali or alkali earth metal such as lithium, sodium, potassium, magnesium, or calcium, a salt containing an organic base such as benzathine, N-methyl-D-glucamine, or hydrabamine, and a stalt containing an amino acid such as arginine or lysine. These salts may be converted into a free form by treatment with appropriate acid or base. The term "additional salt" may be taken to include solvates obtainable from any of the compounds of Formula I or Formula II and salts thereof. Examples of these solvates are hydrates and alcoholates.

In some embodiments, stereochemical isomers of the pyridone derivative compound may be any compounds derived from the compounds represented by Formula I or Formula II. Unless otherwise mentioned or indicated, the chemical designation of a compound encompasses a mixture of any possible stereochemically isomeric forms which the compound may possess, wherein the mixture may contain any diastereomers and/or enantiomers of the basic molecular structure of the compound. In particular, the stereocenter may be in either R or S-configuration, a substituent of divalent cyclic (partially) saturated radical may be in either the cis- or trans-configuration. A compound with a double bond may have either E or Z-stereochemistry in the double bond. Any stereochemical isomer of the compound of Formula I or Formula II also falls within the scope of the present disclosure.

In some embodiments, the pyridone derivative compound may be selected from the group consisting of N-(1-azoniabicyclo[2.2.2]octan-3-yl)-6-oxo-1-phenyl-3-pyridinecarboxamide, N-(1-azabicyclo[2.2.2]octan-3-yl)-1-(2-chlorophenyl)-6-oxo-3-pyridinecarboxamide, N-(1-azabicyclo[2.2.2]octan-3-yl)-1-(3-chlorophenyl)-6-oxo-3-pyridinecarboxamide, N-(1-azabicyclo[2.2.2]octan-3-yl)-1-(4-chlorophenyl)-6-oxo-3-pyridinecarboxamide, N-[(3R)-1-azabicyclo[2.2.2]octan-3-yl]-1-(4-chlorophenyl)-6-oxopyridine-3-carboxamide, N-[(3S)-1-azabicyclo[2.2.2]octan-3-yl]-1-(4-chlorophenyl)-6-oxopyridine-3-carboxamide, N-(1-azabicyclo[2.2.2]octan-3-yl)-1-(4-fluorophenyl)-6-oxo-3-pyridinecarboxamide, N-(1-azabicyclo[2.2.2]octan-3-yl)-1-(2-fluorophenyl)-6-oxo-3-pyridinecarboxamide, N-(1-azabicyclo[2.2.2]octan-3-yl)-1-(3-fluorophenyl)-6-oxo-3-pyridinecarboxamide, N-(1-azabicyclo[2.2.2]octan-3-yl)-1-(4-bromophenyl)-6-oxo-3-pyridinecarboxamide, N-(1-azabicyclo[2.2.2]octan-3-yl)-1-(2-methylphenyl)-6-oxo-3-pyridinecarboxamide, N-(1-azabicyclo[2.2.2]octan-3-yl)-1-(4-methylphenyl)-6-oxo-3-pyridinecarboxamide, N-(1-azabicyclo[2.2.2]octan-3-yl)-1-(3-methylphenyl)-6-oxo-3-pyridinecarboxamide, N-(1-azabicyclo[2.2.2]octan-3-yl)-1-(4-ethylphenyl)-6-oxo-3-pyridinecarboxamide, N-(1-azabicyclo[2.2.2]octan-3-yl)-6-oxo-1-(4-propylphenyl)-3-pyridinecarboxamide, N-(1-azabicyclo[2.2.2]octan-3-yl)-6-oxo-1-(2-propan-2-ylphenyl)-3-pyridinecarboxamide, N-(1-azabicyclo[2.2.2]octan-3-yl)-6-oxo-1-(4-propan-2-ylphenyl)-3-pyridinecarboxamide, N-(1-azabicyclo[2.2.2]octan-3-yl)-1-(4-cyclohexylphenyl)-6-oxo-3-pyridinecarboxamide, N-(1-azabicyclo[2.2.2]octan-3-yl)-1-(4-methoxyphenyl)-6-oxo-3-pyridinecarboxamide, N-(1-azabicyclo[2.2.2]octan-3-yl)-1-(2-methoxyphenyl)-6-oxo-3-pyridinecarboxamide, N-(1-azabicyclo[2.2.2]octan-3-yl)-1-(3-methoxyphenyl)-6-oxo-3-pyridinecarboxamide, N-(1-azabicyclo[2.2.2]octan-3-yl)-6-oxo-1-[4-(trifluoromethyl)phenyl]-3-pyridinecarboxamide, N-(1-azabicyclo[2.2.2]octan-3-yl)-6-oxo-1-[4-(trifluoromethoxy)phenyl]-3-pyridinecarboxamide, N-(1-azabicyclo[2.2.2]octan-3-yl)-6-oxo-1-[2-(trifluoromethoxy)phenyl]-3-pyridinecarboxamide, N-(1-azabicyclo[2.2.2]octan-3-yl)-1-(2,4-dichlorophenyl)-6-oxo-3-pyridinecarboxamide, N-[(3R)-1-azabicyclo[2.2.2]octan-3-yl]-1-(2,4-dichlorophenyl)-6-oxo-3-pyridinecarboxamide, N-[(3S)-1-azabicyclo[2.2.2]octan-3-yl]-1-(2,4-dichlorophenyl)-6-oxo-3-pyridinecarboxamide, N-(1-azabicyclo[2.2.2]octan-3-yl)-1-(3-chloro-4-methoxyphenyl)-6-oxo-3-pyridinecarboxamide, N-(1-azabicyclo[2.2.2]octan-3-yl)-1-(2-chloro-4-methylphenyl)-6-oxo-3-pyridinecarboxamide, N-(1-azabicyclo[2.2.2]octan-3-yl)-1-(2,5-difluorophenyl)-6-oxo-3-pyridinecarboxamide, N-(1-azabicyclo[2.2.2]octan-3-yl)-1-(3,5-dichlorophenyl)-6-oxo-3-pyridinecarboxamide, N-(1-azabicyclo[2.2.2]octan-3-yl)-1-(2,4-dimethylphenyl)-6-oxo-3-pyridinecarboxamide, N-(1-azabicyclo[2.2.2]octan-3-yl)-1-(2-chloro-4-methylphenyl)-6-oxo-3-pyridinecarboxamide, N-(1-azabicyclo[2.2.2]octan-3-yl)-1-(2,4-difluorophenyl)-6-oxo-3-pyridinecarboxamide, N-(1-azabicyclo[2.2.2]octan-3-yl)-1-(2-chloro-5-methylphenyl)-6-oxo-3-pyridinecarboxamide, N-(1-azabicyclo[2.2.2]octan-3-yl)-1-(4-tert-butyl-2-chlorophenyl)-6-oxo-3-pyridinecarboxamide, N-(1-azabicyclo[2.2.2]octan-3-yl)-1-(2-chloro-4-fluorophenyl)-6-oxo-3-pyridinecarboxamide, N-(1-azabicyclo[2.2.2]octan-3-yl)-1-(4-chloro-2-fluorophenyl)-6-oxo-3-pyridinecarboxamide, N-(1-azabicyclo[2.2.2]octan-3-yl)-1-(3,4-dimethoxyphenyl)-6-oxo-3-pyridinecarboxamide, N-(1-azabicyclo[2.2.2]octan-3-yl)-1-(3,4-dichlorophenyl)-6-oxo-3-pyridinecarboxamide, N-(1-azabicyclo[2.2.2]octan-3-yl)-1-(3,4-difluorophenyl)-6-oxo-3-pyridinecarboxamide, N-(1-azabicyclo[2.2.2]octan-3-yl)-

1-(4-chloro-3-methylphenyl)-6-oxo-3-pyridinecarboxamide, N-(1-azabicyclo[2.2.2]octan-3-yl)-1-(3,5-difluorophenyl)-6-oxo-3-pyridinecarboxamide, N-(1-azabicyclo[2.2.2]octan-3-yl)-1-(4-fluoro-2-methylphenyl)-6-oxo-3-pyridinecarboxamide, N-(1-azabicyclo[2.2.2]octan-3-yl)-1-(2,5-dimethoxyphenyl)-6-oxo-3-pyridinecarboxamide, N-(1-azabicyclo[2.2.2]octan-3-yl)-1-(2,3-dichlorophenyl)-6-oxo-3-pyridinecarboxamide, N-(1-azabicyclo[2.2.2]octan-3-yl)-1-(3-chloro-2-methoxyphenyl)-6-oxo-3-pyridinecarboxamide, N-(1-azabicyclo[2.2.2]octan-3-yl)-1-(3-fluoro-4-methoxyphenyl)-6-oxo-3-pyridinecarboxamide, N-(1-azabicyclo[2.2.2]octan-3-yl)-1-(2,4-dimethoxyphenyl)-6-oxo-3-pyridinecarboxamide, N-(1-azabicyclo[2.2.2]octan-3-yl)-1-(3-chloro-4-fluorophenyl)-6-oxo-3-pyridinecarboxamide, N-(1-azabicyclo[2.2.2]octan-3-yl)-1-(4-chloro-3-methoxyphenyl)-6-oxo-3-pyridinecarboxamide, N-(1-azabicyclo[2.2.2]octan-3-yl)-1-(2-methoxy-5-methylphenyl)-6-oxo-3-pyridinecarboxamide, N-(1-azabicyclo[2.2.2]octan-3-yl)-1-(4-chloro-2-methylphenyl)-6-oxo-3-pyridinecarboxamide, N-(1-azabicyclo[2.2.2]octan-3-yl)-1-(4-methoxy-2-methylphenyl)-6-oxo-3-pyridinecarboxamide, N-(1-azabicyclo[2.2.2]octan-3-yl)-1-[4-chloro-3-(trifluoromethyl)phenyl]-6-oxo-3-pyridinecarboxamide, N-(1-azabicyclo[2.2.2]octan-3-yl)-1-(5-chloro-2-methoxyphenyl)-6-oxo-3-pyridinecarboxamide, N-(1-azabicyclo[2.2.2]octan-3-yl)-1-[2-chloro-4-(trifluoromethoxy)phenyl]-6-oxo-3-pyridinecarboxamide, N-(1-azabicyclo[2.2.2]octan-3-yl)-1-(4-chloro-3-fluorophenyl)-6-oxo-3-pyridinecarboxamide, N-(1-azabicyclo[2.2.2]octan-3-yl)-1-(2,4,5-trimethoxyphenyl)-6-oxo-3-pyridinecarboxamide, N-(1-azabicyclo[2.2.2]octan-3-yl)-1-(2,4,5-trichlorophenyl)-6-oxo-3-pyridinecarboxamide, N-(1-azabicyclo[2.2.2]octan-3-yl)-1-(3,4,5-trifluorophenyl)-6-oxo-3-pyridinecarboxamide, N-(1-azabicyclo[2.2.2]octan-3-yl)-6-oxo-1-(3-phenylphenyl)-3-pyridinecarboxamide, N-(1-azabicyclo[2.2.2]octan-3-yl)-6-oxo-1-(2-phenylmethoxyphenyl)-3-pyridinecarboxamide, N-(1-azabicyclo[2.2.2]octan-3-yl)-6-oxo-1-(2-phenylphenyl)-3-pyridinecarboxamide, N-(1-azabicyclo[2.2.2]octan-3-yl)-1-(4-phenylphenyl)-6-oxo-3-pyridinecarboxamide, N-(1-azabicyclo[2.2.2]octan-3-yl)-1-(2-methoxy-5-phenylphenyl)-6-oxo-3-pyridinecarboxamide, N-(1-azabicyclo[2.2.2]octan-3-yl)-1-[4-(4-chlorophenyl)phenyl]-6-oxo-3-pyridinecarboxamide, N-(1-azabicyclo[2.2.2]octan-3-yl)-1-[4-(4-methoxyphenyl)phenyl]-6-oxo-3-pyridinecarboxamide, N-(1-azabicyclo[2.2.2]octan-3-yl)-1-[4-(4-methylphenyl)phenyl]-6-oxo-3-pyridinecarboxamide, N-(1-azabicyclo[2.2.2]octan-3-yl)-1-(2-chloro-4-phenylphenyl)-6-oxo-3-pyridinecarboxamide, N-(1-azabicyclo[2.2.2]octan-3-yl)-1-[4-(4-chlorophenoxy)phenyl]-6-oxo-3-pyridinecarboxamide, N-(1-azabicyclo[2.2.2]octan-3-yl)-1-[4-(4-methylphenoxy)phenyl]-6-oxo-3-pyridinecarboxamide, N-(1-azabicyclo[2.2.2]octan-3-yl)-6-oxo-1-(4-phenoxyphenyl)-3-pyridinecarboxamide, N-(1-azabicyclo[2.2.2]octan-3-yl)-6-oxo-1-(2-phenoxyphenyl)-3-pyridinecarboxamide, N-(1-azabicyclo[2.2.2]octan-3-yl)-1-(4-ethynylphenyl)-6-oxo-3-pyridinecarboxamide, N-(1-azabicyclo[2.2.2]octan-3-yl)-1-[4-(methylthio)phenyl]-6-oxo-3-pyridinecarboxamide, N-(1-azabicyclo[2.2.2]octan-3-yl)-1-[2-(methylthio)phenyl]-6-oxo-3-pyridinecarboxamide, N-[(3R)-1-azabicyclo[2.2.2]octan-3-yl]-1-[2-(methylthio)phenyl]-6-oxo-3-pyridinecarboxamide, N-[(3S)-1-azabicyclo[2.2.2]octan-3-yl]-1-[2-(methylthio)phenyl]-6-oxo-3-pyridinecarboxamide, N-(1-azabicyclo[2.2.2]octan-3-yl)-1-[2-(ethylthio)phenyl]-6-oxo-3-pyridinecarboxamide, N-(1-azabicyclo[2.2.2]octan-3-yl)-6-oxo-1-[2-(propan-2-ylthio)phenyl]-3-pyridinecarboxamide, N-(1-azabicyclo[2.2.2]octan-3-yl)-6-oxo-1-[2-(phenylmethylthio)phenyl]-3-pyridinecarboxamide, N-(1-azabicyclo[2.2.2]octan-3-yl)-1-[2-(methylthio)-5-(trifluoromethyl)phenyl]-6-oxo-3-pyridinecarboxamide, N-(1-azabicyclo[2.2.2]octan-3-yl)-1-[4-methoxy-2-(methylthio)phenyl]-6-oxo-3-pyridinecarboxamide, N-(1-azabicyclo[2.2.2]octan-3-yl)-1-[2-(ethylthio)-4-methoxyphenyl]-6-oxo-3-pyridinecarboxamide, N-(1-azabicyclo[2.2.2]octan-3-yl)-1-[4-chloro-2-(methylthio)phenyl]-6-oxo-3-pyridinecarboxamide, N-[(3R)-1-azabicyclo[2.2.2]octan-3-yl]-1-[4-chloro-2-(methylthio)phenyl]-6-oxo-3-pyridinecarboxamide, N-[(3S)-1-azabicyclo[2.2.2]octan-3-yl]-1-[4-chloro-2-(methylthio)phenyl]-6-oxo-3-pyridinecarboxamide, N-(1-azabicyclo[2.2.2]octan-3-yl)-1-[4-methyl-2-(methylthio)phenyl]-6-oxo-3-pyridinecarboxamide, N-[(3R)-1-azabicyclo[2.2.2]octan-3-yl]-1-[4-methyl-2-(methylthio)phenyl]-6-oxo-3-pyridinecarboxamide, N-[(3S)-1-azabicyclo[2.2.2]octan-3-yl]-1-[4-methyl-2-(methylthio)phenyl]-6-oxo-3-pyridinecarboxamide, N-(1-azabicyclo[2.2.2]octan-3-yl)-1-[4-tert-butyl-2-(methylthio)phenyl]-6-oxo-3-pyridinecarboxamide, N-(1-azabicyclo[2.2.2]octan-3-yl)-1-[4-chloro-2-(propan-2-ylthio)phenyl]-6-oxo-3-pyridinecarboxamide, N-(1-azabicyclo[2.2.2]octan-3-yl)-1-[2-(methylthio)-4-propylphenyl]-6-oxo-3-pyridinecarboxamide, N-(1-azabicyclo[2.2.2]octan-3-yl)-6-oxo-1-[2-(phenylthio)phenyl]-3-pyridinecarboxamide, N-(1-azabicyclo[2.2.2]octan-3-yl)-1-[2-(methylthio)-4-propan-2-ylphenyl]-6-oxo-3-pyridinecarboxamide, N-(1-azabicyclo[2.2.2]octan-3-yl)-1-[4-chloro-2-(ethylthio)phenyl]-6-oxo-3-pyridinecarboxamide, N-(1-azabicyclo[2.2.2]octan-3-yl)-1-[4-ethyl-2-(methylthio)phenyl]-6-oxo-3-pyridinecarboxamide, N-(1-azabicyclo[2.2.2]octan-3-yl)-1-[4-cyclohexyl-2-(methylthio)phenyl]-6-oxo-3-pyridinecarboxamide, N-(1-azabicyclo[2.2.2]octan-3-yl)-1-(2-methylsulfonylphenyl)-6-oxo-3-pyridinecarboxamide, N-(1-azabicyclo[2.2.2]octan-3-yl)-1-(4-methylsulfonylphenyl)-6-oxo-3-pyridinecarboxamide, N-(1-azabicyclo[2.2.2]octan-3-yl)-1-(1-naphthalenyl)-6-oxo-3-pyridinecarboxamide, N-(1-azabicyclo[2.2.2]octan-3-yl)-1-(2-naphthalenyl)-6-oxo-3-pyridinecarboxamide, N-(1-azabicyclo[2.2.2]octan-3-yl)-6-oxo-1-[2-(2-thiazolyl)phenyl]-3-pyridinecarboxamide, N-(1-azabicyclo[2.2.2]octan-3-yl)-1-[4-chloro-2-(2-thiazolyl)phenyl]-6-oxo-3-pyridinecarboxamide, N-(1-azabicyclo[2.2.2]octan-3-yl)-1-[2-(5-methyl-2-thiazolyl)phenyl]-6-oxo-3-pyridinecarboxamide, N-(1-azabicyclo[2.2.2]octan-3-yl)-1-[2-(1,3-benzothiazole-2-yl)phenyl]-6-oxo-3-pyridinecarboxamide, N-(1-azabicyclo[2.2.2]octan-3-yl)-1-[4-(5-methyl-2-thiophenyl)phenyl]-6-oxo-3-pyridinecarboxamide, N-(1-azabicyclo[2.2.2]octan-3-yl)-1-[2-chloro-4-(5-methyl-2-thiophenyl)phenyl]-6-oxo-3-pyridinecarboxamide, N-(1-azabicyclo[2.2.2]octan-3-yl)-6-oxo-1-(2-thiophene-2-ylphenyl)-3-pyridinecarboxamide, N-(1-azabicyclo[2.2.2]octan-3-yl)-1-[2-(5-methyl-2-thiophenyl)phenyl]-6-oxo-3-pyridine carboxamide, N-(1-azabicyclo[2.2.2]octan-3-yl)-1-[3-(2-methyl-4-thiazolyl)phenyl]-6-oxo-3-pyridinecarboxamide, N-(1-azabicyclo[2.2.2]octan-3-yl)-1-[4-dimethylaminophenyl]-6-oxo-3-pyridinecarboxamide, N-(1-azabicyclo[2.2.2]octan-3-yl)-1-{4-[(methyl-prop-2-ynyl-amino)-methyl]-phenyl}-6-oxo-3-pyridinecarboxamide, (1-azabicyclo[2.2.2]octan-3-yl)-6-oxo-1-phenyl-3-pyridinecarboxylate, (1-azabicyclo[2.2.2]octan-3-yl)-1-(2,4-dichlorophenyl)-6-oxo-3-pyridinecarboxylate, N-(1-azabicyclo[2.2.2]octan-3-yl)-2-oxo-1-phenyl-3-pyridinecarboxamide, N-(1-azabicyclo[2.2.2]octan-3-yl)-1-(4-methoxyphenyl)-2-oxo-3-pyridinecarboxamide, N-(1-azabicyclo[2.2.2]octan-3-yl)-1-(4-chlorophenyl)-2-oxo-3-pyridinecarboxamide, N-(1-azabicyclo[2.2.2]octan-3-yl)-2-oxo-1-[4-(trifluoromethyl)phenyl]-3-pyridinecarboxamide, and N-(1-azabicyclo[2.2.2]octan-3-yl)-1-(4-tert-butylphenyl)-2-oxo-3-pyridinecarboxamide.

In some embodiments, the pyridine derivative compound may be an agonist or partial agonist of an α7 nicotinic acetylcholine receptor.

The term "agonist" used herein is understood to be given its broadest meaning, i.e, as any molecule that partially or entirely activate at least one biological activity of a target material (for example, the α7 nicotinic acetylcholine receptor). For example, the term "agonist" compound refers to a compound that increases or induces the biological activity of a protein (for example, the α7 nicotinic acetylcholine receptor c-Met) to which the agonist compound binds. For example, the pyridine derivative compound may specifically bind to the extracellular domain of the α7 nicotinic acetylcholine receptor to induce intracellular signal transmission, proving efficacy in prevention or treatment of cognitive impairments and in neurological recovery.

Nicotinic α7 receptors are known to be significant in the improvement of cognitive functions in, for example, learning, memory and attention. For example, nicotinic α7 receptors are associated with mild cognition impairment, Alzheimer's disease, age-associated and other cognitive impairments, neuropsychiatric cognitive disorder, attention deficit disorder, attention deficit hyperactivity disorder (ADHD), dementia caused by injection or metabolic disorder, Lewy body dementia, convulsions such as epilepsy, multiple cerebral infarcts, mood disorder, compulsive and addictive behaviors, inflammatory disease, and diseases and conditions associated with the control of pain caused from these disorders. The activity of the nicotinic α7 receptor may be changed or regulated by administration of α7 receptor ligands of which non-limiting examples are antagonists, agonists, partial agonists, and inverse agonists. α7 receptor ligands are usable in treatment and prevention of these various types of cognitive impairments and other conditions and diseases, and agonists and partial agonists thereof are known to improve cognitive functions and attention in rodents, non-human primates, and humans [Gotti C and Clementi F (2004) Prog. Neurobiol. 74; 363-396; Jones H E, Garrett B E, Griffiths, R R (1999) J. Pharmacol. Exp. Ther. 288; 188-197; Castner S A, Smagin G N, Piser T M, Wang Y, Smith J S, Christian E P, Mrzljak L, Williams G V (2011) Biol. Psychiatry 69; 12-18; Wallace T L, Callahan P M, Tehim A, Bertrand D, Tombaugh G, Wang S, Xie W, Rowe W B, Ong V, Graham E, Terry A V Jr, Rodefer J S, Herbert B, Murray M, Porter R, Santarelli L, Lowe D A. (2011) J. Pharmacol. Exp. Ther. 336; 242-253; Bitner R S, Bunnelle W H, Decker M W, Drescher K U, Kohlhaas K L, Markosyan S, Marsh K C, Nikkel A L, Browman K, Radek R, Anderson D J, Buccafusco J, Gopalakrishnan M. (2010) J. Pharmacol. Exp. Ther. 334; 875-886; Woodruff-Pak, D S, Santos I S (2000) Behav. Brain Res. 113; 11-19; Spinelli S, Ballard T, Feldon J, Higgins G A, Pryce C R (2006) Neuropharmacology 51; 238-250].

According to another aspect of the present invention, there is provided a pharmaceutical composition for preventing or treating cognitive impairment that includes the above-described pyridone derivative compound, or a pharmaceutically acceptable salt, isomer, solvate or hydrate thereof in a therapeutically effective amount; and a pharmaceutically acceptable carrier.

In some embodiments, the cognitive impairment may be selected from the group consisting of pre-senile dementia, early onset Alzheimer's disease, senile dementia, Alzheimer type dementia, Lewy corpuscle dementia, micro-infarct dementia, AIDS-related dementia, HIV-dementia, dementia associated with Lewy bodies, Down's syndrome associated dementia, Pick's disease, mild cognitive impairment, age associated memory impairment, recent short-term memory impairment, age-associated cognitive disorder, drug-associated cognitive disorder, immunodeficiency syndrome-associated cognitive disorder, vascular disease-associated cognitive impairment, schizophrenia, attention deficit disorder, (ADHD), and learning deficit disorder. The pharmaceutical composition is neuroprotective in terms of prevention or treatment of, for example, Alzheimer's disease, Parkinson's disease, amyotrophic lateral sclerosis (ALS), or Huntington's disease.

The term "cognitive disorder" used therein refers to withdrawals in a wide range of cognitive functions or cognitive domains in animals, for example, in working memory, attention and vigilance, verbal learning and memory, visual learning and memory, reasoning and problem solving, and in particular, for example, in executive function, task processing speed and/or social cognition. Cognitive disorders are known to exhibit attention deficit, disorganized thought, slow retarded thinking, comprehension difficulty, low attention, loss of problem solving ability, imprecise memory, difficulties in expressing thoughts and/or in integration of thought, sense and behavior, or in erasing unreasonable thoughts. The terms "cognitive disorder" and "cognitive deficit" are interchangeable.

The term "treatment" may be taken to include prevention, suppression, and alleviation (regression) of diseases, disorders, or conditions associated with cognitive impairment in animals that have never been diagnosed with such diseases, disorders, or conditions caused by cognitive impairment, but that are apt to such diseases, disorders, or conditions. Accordingly, the term "therapeutically effective amount" refers to an effective dose of a clinical marker necessary to alleviate, reduce or prevent symptoms of diseases to be treated, or an effective dose of an effective active compound for reducing or retarding onset of such symptoms, which may be empirically determined through experiment in an in vivo and/or in vitro model of a disease to be treated.

In some embodiments, the pharmaceutical composition may be formulated in any form to be administered by any suitable route, for example, by oral, rectal, nasal, pulmonary, topical, transdermal, intracisternal, intraperitoneal, vaginal and parenteral (including subcutaneous, intramuscular, intrathecal, intravenous, and intradermal) route, the oral route being preferred. For oral administration, the pharmaceutical composition may include a pharmaceutically acceptable vehicle commonly used in the art. In some embodiments, for oral liquid formulations such as suspensions, syrups, elixirs, and solutions, examples of vehicles are water, glycol, oil, and alcohol. For solid formulations such as pills, capsules, lozenges, examples of vehicles are starch, sugar, kaoline, lubricants, binders, and disintegrants. However, it will be appreciated that the preferred route will depend on the general condition, age of the subject to be treated, the nature of the condition to be treated, and the active ingredient chosen. In some embodiments, the pharmaceutical composition may be prepared in unit dosage form in terms of convenient administration and dose consistency.

In some embodiments, the pharmaceutical composition may be administered by any suitable route, for example, by parenteral route in the form of injections, or by oral route in the form of, for example, tablets, capsules, powders, granules, pellets, troches, dragees, pills, lozenges, aqueous or non-aqueous solutions, suspensions, water-in-oil or oil-in-water emulsions, elixirs, or syrups. For parenteral administration, the pharmaceutical composition may be prepared as dispersions, suspension, emulsions, sterile injection solutions, or dispersions containing sterile powder. The pharmaceutical composition is also available as a depot injection. Other suitable administration forms of the pharmaceutical composition are suppositories, sprays, ointments, creams, gels, inhalations, and skin patches. The pharmaceutical composition may be prepared in any of the above-listed forms using any method known in the art. Any pharmaceutically acceptable vehicle diluent, excipient, or other additives that are commonly used in the art may be used.

In some embodiments, for clinical purposes, the pharmaceutical composition may be administered in a unit dose form of about 0.001-100 mg/kg or in a multi-dose form. A total daily dose of the active compounds disclosed in the present specification may be from about 0.001 mg/kg to about 100 mg/kg per body weight, and in some embodiments, may be from about 0.01 mg/kg to about 10 mg/kg per body weight, but is not limited thereto, which depends on the generic conditions of a patient and the activity of the active compounds administered. In some embodiments, the pharmaceutical composition may be administered about one to three times a day. In some circumstances, the pyridone derivative compounds of Formula I and Formula II may be in formulating prodrug-type effective pharmaceutical compositions.

In some embodiments, the pharmaceutical composition may further include other auxiliary components that do not inhibit or help the function of the active components, and may be formulated in any of a variety of forms known in the art.

According to another aspect of the present disclosure, there is provided a treatment method of a cognitive impairment, the method including contacting a subject to be treated with the pharmaceutical composition described above. The contacting may be performed in vitro or in vivo. The in vivo contacting may include administering the pharmaceutical composition to the subject. The subject may be cells, tissues, organics, or individuals. In some embodiments, the pharmaceutical composition may be adminimistered to a cell, tissue, or organ by direct contact of the pharmaceutical composition after dissolution in a suitable buffer solution, or may be parenterally administered to an individual. Since described above, the pharmaceutical composition and administration method used in the treatment will not be described herein in detail. The subject to which the pharmaceutical composition is administered may be any animal, for example, humans, or non-humans such as dogs, cats, and mice.

Advantageous Effects of Invention

In some embodiments, the pharmaceutical composition may effectively prevent or treat cognitive disorders associated with cognitive impairments.

MODE FOR THE INVENTION

One or more embodiments of the present disclosure will now be described in detail with reference to the following examples. However, these examples are for illustrative purposes only and are not intended to limit the scope of the one or more embodiments of the present disclosure.

Example 1

Synthesis of N-(1-azoniabicyclo[2.2.2]octan-3-yl)-6-oxo-1-phenyl-3-pyridinecarboxamide

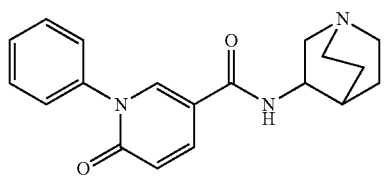 [SMILES: O=C(NC1CN2CCC1CC2)c1ccc(=O)n(-c2ccccc2)c1]

Example 1-1

Synthesis of dimethyl 4-(methoxymethylene)-2-pentanedioate 52 mL (0.73 mmol) of acetyl chloride was slowly dropwise added into a mixed solution of 500 mL of methanol and 50 g (0.36 mol) of coumalic acid at about 0° C. for about 10 minutes while stirring. The resulting reaction solution was stirred under reflux for about 10 hours. After termination of the reaction was determined by liquid chromatography, the solvent was removed in vacuo. The residue was extracted three times with water and ethyl acetate, and an organic solvent phase was purified at a reduced pressure using column chromatography (hexane:ethyl acetate=1:5), thereby obtaining a target compound (Actual yield: 38 g, Percent yield: 53%).

(Major/minor ratio=5.8:1)

$^1$H-NMR (CDCl$_3$,200 MHz, major) δ7.64 (s, 1H), 7.58 (d, 1H), 6.62 (d, 1H), 4.02 (s, 3H), 3.73 (m, 6H)

$^1$H-NMR (CDCl$_3$,200 MHz, minor) δ8.87 (s, 1H), 8.31 (d, 1H), 6.34 (d, 1H), 3.89 (s, 3H), 3.73 (m, 6H)

Example 1-2

Synthesis of methyl 6-oxo-1-phenyl-1,6-dihydro-3-pyridinecarboxylate

After 1.06 g (5.2 mmol) of dimethyl 4-(methoxymethylene)-2-pentanedioate was dissolved in 10 mL of DMF, 510 mg (5.5 mmol) of aniline was added to the solution. Afterward, the resulting reaction solution was stirred under reflux at about 150° C. for 10 hours. After termination of the reaction was determined by liquid chromatography, the reaction solution was diluted with ethyl acetate and was then washed using brine, followed by drying using magnesium sulfate, and filtration. After distillation under reduced pressure, the resulting product was purified using column chromatography (hexane:ethyl acetate=1:2) to obtain a target compound (Actual yield: 750 mg, Yield ratio: 63%).

$^1$H-NMR (CDCl$_3$,200 MHz) δ8.25 (s, 1H), 7.93 (d, 1H), 7.50 (m, 3H), 7.39 (m, 2H), 6.64 (d, 1H), 3.87 (s, 3H)

Example 1-3

Synthesis of 6-oxo-1-phenyl-1,6-dihydro-3-pyridinecarboxylic acid

After 750 mg (3.27 mmol) of methyl 6-oxo-1-phenyl-1,6-dihydro-3-pyridinecarboxylate was dissolved in 9 mL of methanol and 3 mL of water, 235 mg (9.81 mmol) of lithium hydroxide was added to the solution. Afterward, the resulting reaction solution was stirred at about 50° C. for about 5 hours. After termination of the reaction was determined by liquid chromatography, the solvent was removed in vacuo, followed by addition of aqueous HCl to titrate a pH of the reaction product to pH 2. After filtration of the resulting solid compound (Actual yield: 470 mg, Percent yield: 67%), the resulting compound was used without purification.

$^1$H-NMR (DMSO-d$_6$,200 MHz) δ8.18 (s, 1H), 7.88 (d, 1H), 7.49 (m, 5H), 6.54 (d, 2H)

Example 1-4

Synthesis of N-(1-azabicyclo[2.2.2]octan-3-yl)-6-oxo-1-phenyl-3-pyridinecarboxamide N-(1-azabicyclo[2.2.2]octan-3-yl)-6-oxo-1-phenyl-3-pyridinecarboxamide was synthesized using one of the following methods.

Method 1:

After 300 mg (1.39 mmol) of 6-oxo-1-phenyl-1,6-dihydro-3-pyridinecarboxylic acid was dissolved in 10 mL of tetrahydrofuran and 1 mL of DMF, 415 mg (2.08 mmol) of 3-aminoquinuclidine dihydrochloride and 538 mg (4.17 mmol) of diethylisopropylamide were added to the solution. After the reaction solution was stirred at room temperature for about 30 minutes, 635 mg (1.67 mmol) of O-(benzotriazole-1-yl)-N,N,N',N'-tetramethyluroniumhexafluorophosphate (HATU) was added to the reaction solution, which was then stirred at room temperature for about 24 hours. After termination of the reaction was determined by liquid chromatography, the solvent was removed in vacuo, followed by extraction three times with chloroform and an aqueous NaOH solution (pH 12) and purification using liquid chromatography (chloroform:methanol:ammonia water=10:1:0.1) to obtain a target compound (Actual yield: 281 mg, Percent yield: 63%).

Method 2:

After dissolution of 300 mg (1.39 mmol) of 6-oxo-1-phenyl-1,6-dihydro-3-pyridinecarboxylic acid in 10 mL of dichloromethane, 530 mg (4.17 mmol) of oxalyl chloride was added to the solution, and a catalytic amount of DMF was then added thereto. After being stirred at room temperature for about 2 hours, the solvent was removed in vacuo. After addition of 415 mg (2.08 mmol) of quinuclidine dihydrochloride to 10 mL of acetonitrile, 898 mg (6.95 mmol) of diethylisopropylamide was added to the solution. This reaction solution was stirred at room temperature for about 24 hours. After addition of the reaction mixture distilled under reduced pressure to acetonitrile, the 3-aminoquinuclidine dihydrochloride reaction solution was slowly added thereto, followed by stirring at room temperature for about 15 hours and the solvent was removed in vacuo. The resulting compound was extracted three times with chloroform and an aqueous NaOH solution (pH=12), and was then purified using liquid chromatography (chloroform:methanol: ammonia water=10:1:0.1) to obtain a target compound (Actual yield: 360 mg, Percent yield: 80%).

Method 3:

After 300 mg (1.39 mmol) of 6-oxo-1-phenyl-1,6-dihydro-3-pyridinecarboxylic acid was dissolved in 10 mL of acetonitrile, 415 mg (2.08 mmol) of 3-aminoquinuclidine dihydrochloride and 718 mg (5.56 mmol) of diethylisopropylamide were added to the solution. Afterward, 207 mg (1.53 mmol) of 1-hydroxylbenzotriazole (HOBt) and 266 mg (1.39 mmol) of N-(3-dimethylaminopropyl)-N'-ethylcarbodiimide hydrochloride (EDC) were added to the reaction solution. This reaction solution was stirred at room temperature for about 24 hours. After termination of the reaction was determined by liquid chromatography, the solvent was removed in vacuo and then extracted three times with chloroform and an aqueous NaOH solution (pH=12), followed by purification using liquid chromatography (chloroform:methanol: ammonia water=10:1:0.1) to obtain a target compound (Actual yield: 317 mg, Percent yield: 70%).

$^1$H-NMR (CDCl$_3$,200 MHz) δ8.11 (s, 1H), 7.75 (d, 1H), 7.40 (m, 4H), 6.65 (d, 1H), 6.26 (br, 1H), 4.15 (m, 1H), 3.39 (m, 1H), 2.89 (m, 4H), 2.53 (m, 1H), 2.06 (m, 1H), 1.53 (m, 4H)

Example 2

Synthesis of N-(1-azabicyclo[2.2.2]octan-3-yl)-1-(2-chlorophenyl)-6-oxo-3-pyridinecarboxamide

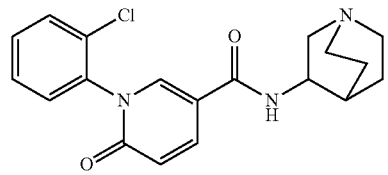 [SMILES: O=C(NC1CN2CCC1CC2)c1ccc(=O)n(-c2ccccc2Cl)c1]

A target compound was obtained in the same manner as in Example 1 and Method 2, except that 2-chloroaniline was used as a starting material.

$^1$H-NMR (CDCl$_3$,200 MHz) δ7.97 (s, 1H), 7.84 (d, 1H), 7.42 (m, 4H), 7.14 (br, d, 1H), 6.54 (d, 1H), 4.06 (m, 1H), 3.25 (m, 1H), 2.77 (m, 4H), 2.56 (m, 1H), 1.92 (m, 1H), 1.65 (m, 3H), 1.45 (m, 1H)

Example 3

Synthesis of N-(1-azabicyclo[2.2.2]octan-3-yl)-1-(3-chlorophenyl)-6-oxo-3-pyridinecarboxamide

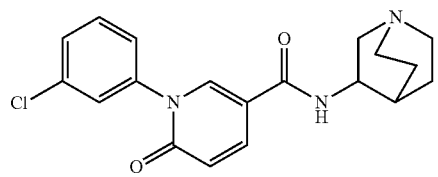 [SMILES: O=C(NC1CN2CCC1CC2)c1ccc(=O)n(-c2cccc(Cl)c2)c1]

A target compound was obtained in the same manner as in Example 1 and Method 2, except that 3-chloroaniline was used as a starting material.

$^1$H-NMR (CDCl$_3$,200 MHz) δ8.11 (s, 1H), 7.83 (d, 1H), 7.29 (m, 4H), 6.94 (br, d, 1H), 6.56 (d, 1H), 4.09 (m, 1H), 3.32 (m, 1H), 2.77 (m, 5H), 2.01 (m, 1H), 1.72 (m, 3H), 1.59 (m, 1H)

Example 4

Synthesis of N-(1-azabicyclo[2.2.2]octan-3-yl)-1-(4-chlorophenyl)-6-oxo-3-pyridinecarboxamide

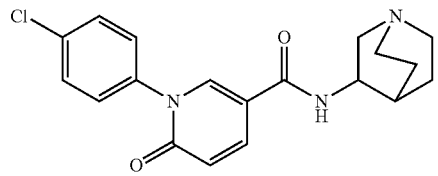 [SMILES: O=C(NC1CN2CCC1CC2)c1ccc(=O)n(-c2ccc(Cl)cc2)c1]

A target compound was obtained in the same manner as in Example 1 and Method 2, except that 4-chloroaniline was used as a starting material.

¹H-NMR (CDCl₃,200 MHz) δ8.20 (s, 1H), 7.84 (d, 1H), 7.42 (d, 2H), 7.25 (d, 2H), 7.04 (br, d, 1H), 6.50 (d, 1H), 4.13 (m, 1H), 3.23 (m, 1H), 2.59 (m, 5H), 2.01 (m, 1H), 1.67 (m, 3H), 1.40 (m, 1H)

Example 5

Synthesis of N-[(3R)-1-azabicyclo[2.2.2]octan-3-yl]-1-(4-chlorophenyl)-6-oxopyridine-3-carboxamide

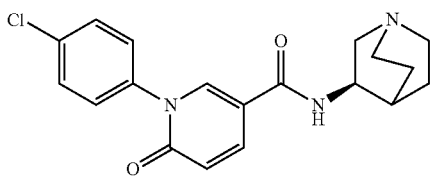 [SMILES: O=C(N[C@H]1CN2CCC1CC2)c1ccc(=O)n(-c2ccc(Cl)cc2)c1]

6-Oxo-1-(4-chlorophenyl)-1,6-dihydro-3-pyridinecarboxylic acid was synthesized in the same manner as in Example 1-2 and Example 1-3, except that 4-chloroaniline was used as a starting material. A target compound was obtained from the synthesized 6-oxo-1-(4-chlorophenyl)-1,6-dihydro-3-pyridinecarboxylic acid and 3R-aminoquinuclidine dihydrochloride in the same manner as in Example 1-4 and Method 2.

¹H-NMR (CDCl₃,200 MHz) δ8.20 (s, 1H), 7.84 (d, 1H), 7.42 (d, 2H), 7.25 (d, 2H), 7.04 (br, d, 1H), 6.50 (d, 1H), 4.13 (m, 1H), 3.23 (m, 1H), 2.59 (m, 5H), 2.01 (m, 1H), 1.67 (m, 3H), 1.40 (m, 1H)

Example 6

Synthesis of N-[(3S)-1-azabicyclo[2.2.2]octan-3-yl]-1-(4-chlorophenyl)-6-oxopyridine-3-carboxamide

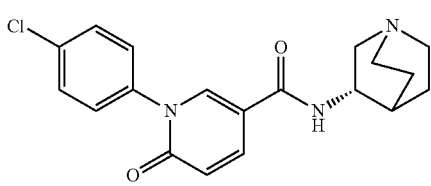 [SMILES: O=C(N[C@@H]1CN2CCC1CC2)c1ccc(=O)n(-c2ccc(Cl)cc2)c1]

6-Oxo-1-(4-chlorophenyl)-1,6-dihydro-3-pyridinecarboxylic acid was synthesized in the same manner as in Example 1-2 and Example 1-3, except that 4-chloroaniline was used as a starting material. A target compound was obtained from the synthesized 6-oxo-1-(4-chlorophenyl)-1,6-dihydro-3-pyridinecarboxylic acid and 3S-aminoquinuclidine dihydrochloride in the same manner as in Example 1-4 and Method 2.

¹H-NMR (CDCl₃,200 MHz) δ8.20 (s, 1H), 7.84 (d, 1H), 7.42 (d, 2H), 7.25 (d, 2H), 7.04 (br, d, 1H), 6.50 (d, 1H), 4.13 (m, 1H), 3.23 (m, 1H), 2.59 (m, 5H), 2.01 (m, 1H), 1.67 (m, 3H), 1.40 (m, 1H)

Example 7

Synthesis of N-(1-azabicyclo[2.2.2]octan-3-yl)-1-(4-fluorophenyl)-6-oxo-3-pyridinecarboxamide

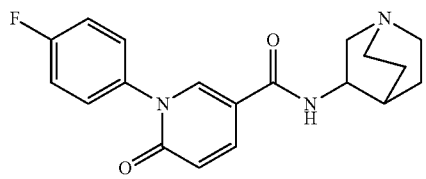 [SMILES: O=C(NC1CN2CCC1CC2)c1ccc(=O)n(-c2ccc(F)cc2)c1]

A target compound was obtained in the same manner as in Example 1 and Method 2, except that 4-fluoroaniline was used as a starting material.

¹H-NMR (CDCl₃,200 MHz) δ8.11 (s, 1H), 7.74 (d, 1H), 7.31 (m, 4H), 6.50 (d, 1H), 6.35 (br, d, 1H), 4.11 (m, 1H), 3.38 (m, 1H), 2.86 (m, 4H), 2.61 (m, 1H), 2.03 (m, 1H), 1.74 (m, 3H), 1.55 (m, 1H)

Example 8

Synthesis of N-(1-azabicyclo[2.2.2]octan-3-yl)-1-(2-fluorophenyl)-6-oxo-3-pyridinecarboxamide

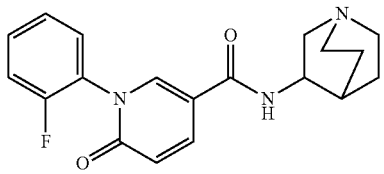 [SMILES: O=C(NC1CN2CCC1CC2)c1ccc(=O)n(-c2ccccc2F)c1]

A target compound was obtained in the same manner as in Example 1 and Method 1, except that 2-fluoroaniline was used as a starting material.

¹H-NMR (CDCl₃,500 MHz) δ8.01 (m, 1H), 7.72 (m, 1H), 7.43 (m, 1H), 7.32 (m, 3H), 6.64 (d, 1H), 6.12 (br, 1H), 4.03 (m, 1H), 3.40 (m, 1H), 2.81 (m, 4H), 2.59 (m, 1H), 2.02 (m, 1H), 1.83 (m, 3H), 1.58 (m, 1H)

Example 9

Synthesis of N-(1-azabicyclo[2.2.2]octan-3-yl)-1-(3-fluorophenyl)-6-oxo-3-pyridinecarboxamide

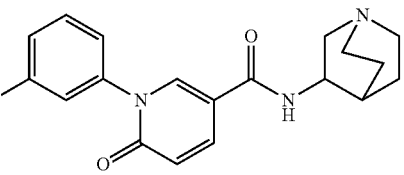

A target compound was obtained in the same manner as in Example 1 and Method 1, except that 3-fluoroaniline was used as a starting material.

¹H-NMR (CDCl₃, 500 MHz) δ 8.08 (s, 1H), 7.69 (d, 1H), 7.51 (m, 1H), 7.15 (m, 3H), 6.67 (d, 1H), 6.17 (br, 1H), 4.15 (m, 1H), 3.44 (m, 1H), 2.95 (m, 4H), 2.67 (d, 1H), 2.05 (m, 1H), 1.68 (m, 3H), 1.43 (m, 1H)

Example 10

Synthesis of N-(1-azabicyclo[2.2.2]octan-3-yl)-1-(4-bromophenyl)-6-oxo-3-pyridinecarboxamide

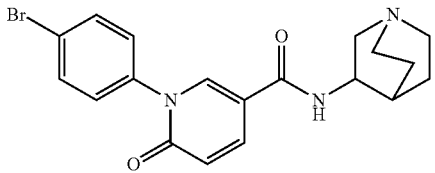

A target compound was obtained in the same manner as in Example 1 and Method 2, except that 4-bromoaniline was used as a starting material.

¹H-NMR (CDCl₃, 200 MHz) δ 8.08 (s, 1H), 7.75 (d, 1H), 7.60 (d, 2H), 7.21 (d, 2H), 6.71 (br, d, 1H), 6.55 (d, 1H), 4.09 (m, 1H), 3.32 (m, 1H), 2.80 (m, 4H), 2.55 (m, 1H), 1.97 (m, 1H), 1.69 (m, 3H), 1.50 (m, 1H)

Example 11

Synthesis of N-(1-azabicyclo[2.2.2]octan-3-yl)-1-(2-methylphenyl)-6-oxo-3-pyridinecarboxamide

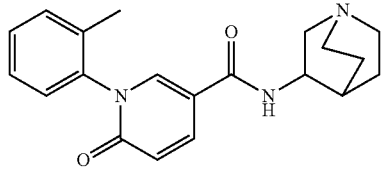

A target compound was obtained in the same manner as in Example 1 and Method 2, except that 2-methylaniline was used as a starting material.

¹H-NMR (CDCl₃, 500 MHz) δ 7.98 (s, 1H), 7.86 (d, 1H), 7.27 (m, 2H), 7.21 (m, 1H), 7.14 (m, 1H), 7.02 (br, d, 1H), 6.45 (d, 1H), 3.95 (m, 1H), 3.17 (m, 1H), 2.74 (m, 4H), 2.49 (m, 1H), 2.17 (s, 3H), 1.84 (m, 1H), 1.58 (m, 3H), 1.29 (m, 1H)

Example 12

Synthesis of N-(1-azabicyclo[2.2.2]octan-3-yl)-1-(4-methylphenyl)-6-oxo-3-pyridinecarboxamide

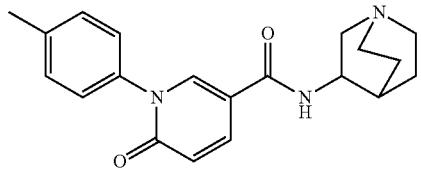 [SMILES: Cc1ccc(-n2cc(C(=O)NC3CN4CCC3CC4)ccc2=O)cc1]

A target compound was obtained in the same manner as in Example 1 and Method 2, except that 4-methylaniline was used as a starting material.

¹H-NMR (CDCl₃, 200 MHz) δ 8.11 (s, 1H), 7.77 (d, 1H), 7.27 (m, 4H), 6.65 (br, d, 1H), 6.57 (d, 1H), 4.09 (m, 1H), 3.34 (m, 1H), 2.89 (m, 5H), 2.48 (s, 3H), 2.01 (m, 1H), 1.72 (m, 3H), 1.52 (m, 1H)

Example 13

Synthesis of N-(1-azabicyclo[2.2.2]octan-3-yl)-1-(3-methylphenyl)-6-oxo-3-pyridinecarboxamide

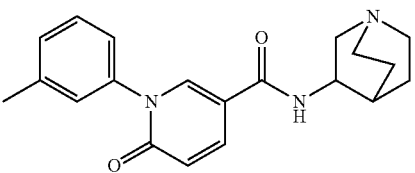 [SMILES: Cc1cccc(-n2cc(C(=O)NC3CN4CCC3CC4)ccc2=O)c1]

A target compound was obtained in the same manner as in Example 1 and Method 1, except that 3-methylaniline was used as a starting material.

¹H-NMR (CDCl₃, 500 MHz) δ 8.07 (s, 1H), 7.78 (d, 1H), 7.39 (m, 1H), 7.25 (m, 1H), 7.15 (m, 2H), 6.62 (d, 1H), 6.37 (br, 1H), 4.08 (m, 1H), 3.40 (m, 1H), 2.83 (m, 4H), 2.59 (m, 1H), 2.40 (s, 3H), 2.20 (m, 1H), 1.63 (m, 3H), 1.42 (m, 1H)

Example 14

Synthesis of N-(1-azabicyclo[2.2.2]octan-3-yl)-1-(4-ethylphenyl)-6-oxo-3-pyridinecarboxamide

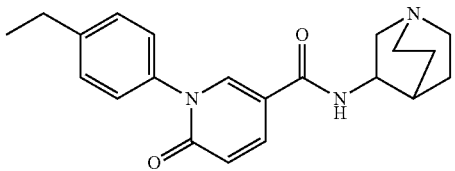 [SMILES: CCc1ccc(-n2cc(C(=O)NC3CN4CCC3CC4)ccc2=O)cc1]

A target compound was obtained in the same manner as in Example 1 and Method 1, except that 4-ethylaniline was used as a starting material.

¹H-NMR (CDCl₃, 500 MHz) δ 8.08 (s, 1H), 7.69 (m, 1H), 7.27 (m, 4H), 6.64 (m, 1H), 6.04 (br, 1H), 4.12 (m, 1H), 3.44 (m, 1H), 2.87 (m, 4H), 2.71 (m, 2H), 2.60 (m, 1H), 2.05 (m, 1H), 1.70 (m, 3H), 1.53 (m, 1H), 1.28 (t, 3H)

Example 15

Synthesis of N-(1-azabicyclo[2.2.2]octan-3-yl)-6-oxo-1-(4-propylphenyl)-3-pyridinecarboxamide

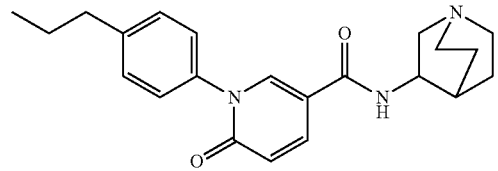 [SMILES: CCCc1ccc(-n2cc(C(=O)NC3CN4CCC3CC4)ccc2=O)cc1]

A target compound was obtained in the same manner as in Example 1 and Method 1, except that 4-propylaniline was used as a starting material.

$^1$H-NMR (CDCl$_3$,500 MHz) δ8.08 (s, 1H), 7.67 (d, 1H), 7.31 (m, 4H), 6.65 (d, 1H), 5.95 (br, 1H), 4.10 (m, 1H), 3.46 (m, 1H), 2.86 (m, 4H), 2.65 (m, 2H), 2.52 (m, 1H), 2.01 (m, 1H), 1.72 (m, 5H), 1.55 (m, 1H), 1.02 (t, 3H)

Example 16

Synthesis of N-(1-azabicyclo[2.2.2]octan-3-yl)-6-oxo-1-(2-propan-2-ylphenyl)-3-pyridinecarboxamide

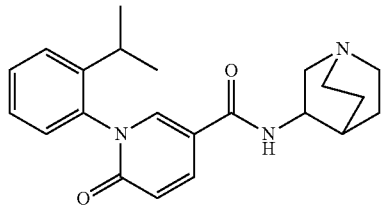 [SMILES: CC(C)c1ccccc1-n1cc(C(=O)NC2CN3CCC2CC3)ccc1=O]

A target compound was obtained in the same manner as in Example 1 and Method 2, except that 2-isopropylaniline was used as a starting material.

$^1$H-NMR (CDCl$_3$,500 MHz) δ8.02 (s, 1H), 7.85 (d, 1H), 7.46 (m, 2H), 7.29 (m, 1H), 7.08 (m, 1H), 6.87 (br, d, 1H), 6.54 (d, 1H), 4.06 (m, 1H), 3.39 (m, 1H), 2.80 (m, 4H), 2.67 (m, 1H), 2.56 (m, 1H), 1.94 (m, 1H), 1.67 (m, 3H), 1.41 (m, 1H), 1.17 (d, 6H)

Example 17

Synthesis of N-(1-azabicyclo[2.2.2]octan-3-yl)-6-oxo-1-(4-propan-2-ylphenyl)-3-pyridinecarboxamide

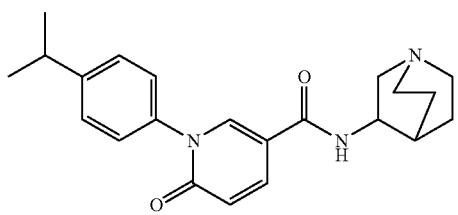 [SMILES: CC(C)c1ccc(-n2cc(C(=O)NC3CN4CCC3CC4)ccc2=O)cc1]

A target compound was obtained in the same manner as in Example 1 and Method 1, except that 4-isopropylaniline was used as a starting material.

$^1$H-NMR (CDCl$_3$,500 MHz) δ8.08 (s, 1H), 7.68 (m, 1H), 7.37 (m, 2H), 7.30 (m, 2H), 6.66 (m, 1H), 5.99 (br, 1H), 4.10 (m, 1H), 3.42 (m, 1H), 2.99 (m, 1H), 2.89 (m, 3H), 2.55 (m, 1H), 2.00 (m, 1H), 1.72 (m, 3H), 1.53 (m, 1H), 1.28 (m, 6H)

Example 18

Synthesis of N-(1-azabicyclo[2.2.2]octan-3-yl)-1-(4-cyclohexylphenyl)-6-oxo-3-pyridinecarboxamide

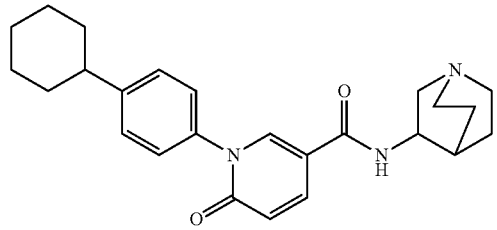 [SMILES: O=C(NC1CN2CCC1CC2)c1ccc(=O)n(-c2ccc(C3CCCCC3)cc2)c1]

A target compound was obtained in the same manner as in Example 1 and Method 1, except that 4-cyclohexylaniline was used as a starting material.

$^1$H-NMR (CDCl$_3$,500 MHz) δ8.07 (s, 1H), 7.68 (d, 1H), 7.34 (d, 2H), 7.30 (d, 2H), 6.65 (d, 1H), 6.01 (br, 1H), 4.12 (m, 1H), 3.43 (m, 1H), 2.87 (m, 4H), 2.58 (m, 2H), 2.02 (m, 1H), 1.90 (m, 4H), 1.79 (m, 1H), 1.73 (m, 3H), 1.54 (m, 1H), 1.47 (m, 4H), 1.28 (m, 1H)

Example 19

Synthesis of N-(1-azabicyclo[2.2.2]octan-3-yl)-1-(4-methoxyphenyl)-6-oxo-3-pyridinecarboxamide

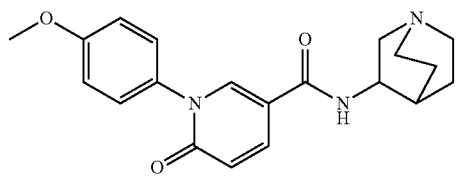 [SMILES: COc1ccc(-n2cc(C(=O)NC3CN4CCC3CC4)ccc2=O)cc1]

A target compound was obtained in the same manner as in Example 1 and Method 2, except that 4-methoxyaniline was used as a starting material.

$^1$H-NMR (CDCl$_3$,200 MHz) δ8.09 (s, 1H), 7.75 (d, 1H), 7.25 (d, 2H), 6.95 (d, 2H), 6.73 (br, d, 1H), 6.53 (d, 1H), 4.05 (m, 1H), 3.83 (s, 3H), 3.30 (m, 1H), 2.61 (m, 5H), 1.95 (m, 1H), 1.70 (m, 3H), 1.46 (m, 1H)

Example 20

Synthesis of N-(1-azabicyclo[2.2.2]octan-3-yl)-1-(2-methoxyphenyl)-6-oxo-3-pyridinecarboxamide

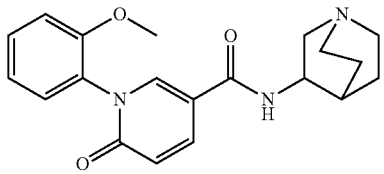 [SMILES: COc1ccccc1-n1cc(C(=O)NC2CN3CCC2CC3)ccc1=O]

A target compound was obtained in the same manner as in Example 1 and Method 1, except that 2-methoxyaniline was used as a starting material.

¹H-NMR (CDCl₃,500 MHz) δ7.98 (s, 1H), 7.78 (d, 1H), 7.48 (t, 1H), 7.24 (s, 1H), 7.13 (t, 2H), 6.72 (d, 1H), 6.12 (br, 1H), 4.11 (m, 1H), 3.87 (s, 3H), 3.78 (m, 1H), 2.85 (m, 4H), 2.53 (m, 1H), 2.05 (m, 1H), 1.82 (m, 3H), 1.52 (m, 1H)

Example 21

Synthesis of N-(1-azabicyclo[2.2.2]octan-3-yl)-1-(3-methoxyphenyl)-6-oxo-3-pyridinecarboxamide

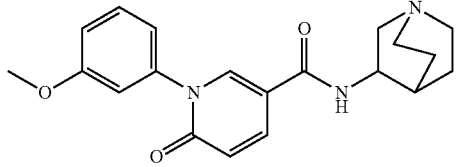 [SMILES: COc1cccc(-n2cc(C(=O)NC3CN4CCC3CC4)ccc2=O)c1]

A target compound was obtained in the same manner as in Example 1 and Method 1, except that 3-methoxyaniline was used as a starting material.

¹H-NMR (CDCl₃,500 MHz) δ7.83 (d, 1H), 7.34 (m, 2H), 7.21 (d, 1H), 6.96 (d, 1H), 6.81 (d, 2H), 6.48 (d, 1H), 4.12 (m, 1H), 3.67 (s, 3H), 3.25 (m, 1H), 2.71 (m, 4H), 2.57 (m, 1H), 1.94 (m, 1H), 1.66 (m, 3H), 1.43 (m, 1H)

Example 22

Synthesis of N-(1-azabicyclo[2.2.2]octan-3-yl)-6-oxo-1-[4-(trifluoromethyl)phenyl]-3-pyridinecarboxamide

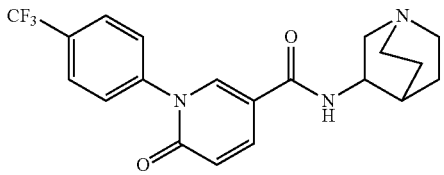 [SMILES: O=C(NC1CN2CCC1CC2)c1ccc(=O)n(-c2ccc(C(F)(F)F)cc2)c1]

A target compound was obtained in the same manner as in Example 1 and Method 2, except that 4-trifluoromethylaniline was used as a starting material.

¹H-NMR (CDCl₃,200 MHz) δ8.09 (s, 1H), 7.83 (d, 1H), 7.79 (d, 2H), 7.66 (d, 2H), 6.67 (br, d, 1H), 6.64 (d, 1H), 4.12 (m, 1H), 3.34 (m, 1H), 2.84 (m, 4H), 2.52 (m, 1H), 2.03 (m, 1H), 1.74 (m, 3H), 1.51 (m, 1H)

Example 23

Synthesis of N-(1-azabicyclo[2.2.2]octan-3-yl)-6-oxo-1-[4-(trifluoromethoxy)phenyl]-3-pyridinecarboxamide

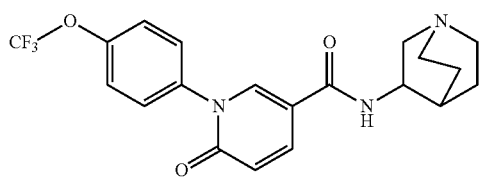 [SMILES: O=C(NC1CN2CCC1CC2)c1ccc(=O)n(-c2ccc(OC(F)(F)F)cc2)c1]

A target compound was obtained in the same manner as in Example 1 and Method 2, except that 4-trifluoromethoxyaniline was used as a starting material.

¹H-NMR (CDCl₃,200 MHz) δ8.09 (s, 1H), 7.73 (d, 1H), 7.40 (m, 4H), 6.65 (d, 1H), 6.25 (br, d, 1H), 4.11 (m, 1H), 3.41 (m, 1H), 2.87 (m, 4H), 2.58 (m, 1H), 2.03 (m, 1H), 1.73 (m, 3H), 1.57 (m, 1H)

Example 24

Synthesis of N-(1-azabicyclo[2.2.2]octan-3-yl)-6-oxo-1-[2-(trifluoromethoxy)phenyl]-3-pyridinecarboxamide

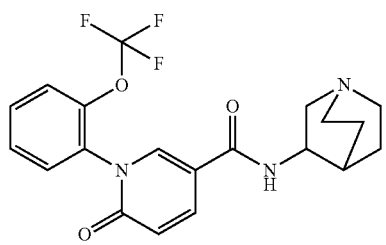 [SMILES: O=C(NC1CN2CCC1CC2)c1ccc(=O)n(-c2ccccc2OC(F)(F)F)c1]

A target compound was obtained in the same manner as in Example 1 and Method 1, except that 2-trifluoromethoxyaniline was used as a starting material.

¹H-NMR (CDCl₃,500 MHz) δ7.99 (s, 1H), 7.72 (m, 1H), 7.58 (m, 1H), 7.44 (m, 3H), 6.67 (m, 1H), 6.09 (br, 1H), 4.13 (m, 1H), 3.43 (m, 1H), 2.92 (m, 4H), 2.62 (m, 1H), 2.03 (m, 1H), 1.73 (m, 3H), 1.64 (m, 1H)

Example 25

Synthesis of N-(1-azabicyclo[2.2.2]octan-3-yl)-1-(2,4-dichlorophenyl)-6-oxo-3-pyridinecarboxamide

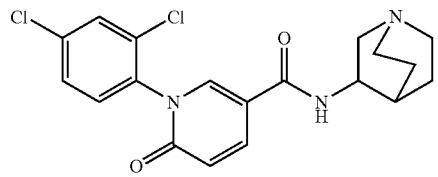 [SMILES: O=C(NC1CN2CCC1CC2)c1ccc(=O)n(-c2ccc(Cl)cc2Cl)c1]

A target compound was obtained in the same manner as in Example 1 and Method 2, except that 2,4-dichloroaniline was used as a starting material.

¹H-NMR (CDCl₃,500 MHz) δ7.96 (s, 1H), 7.87 (d, 1H), 7.54 (s, 1H), 7.36 (d, 1H), 7.22 (d, 1H), 7.02 (br, d, 1H), 6.49 (d, 1H), 4.01 (m, 1H), 3.23 (m, 1H), 2.77 (m, 4H), 2.54 (m, 1H), 1.89 (m, 1H), 1.63 (m, 3H), 1.37 (m, 1H)

Example 26

Synthesis of N-[(3R)-1-azabicyclo[2.2.2]octan-3-yl)-1-(2,4-dichlorophenyl)-6-oxo-3-pyridinecarboxamide

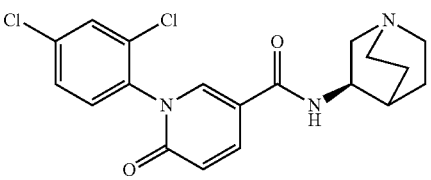 [SMILES: O=C(N[C@H]1CN2CCC1CC2)c1ccc(=O)n(-c2ccc(Cl)cc2Cl)c1]

6-Oxo-1-(2,4-dichlorophenyl)-1,6-dihydro-3-pyridinecarboxylic acid was synthesized in the same manner as in Example 1-2 and Example 1-3, except that 2,4-dichloroaniline was used as a starting material. A target compound was obtained from the synthesized 6-oxo-1-(2,4-dichlorophenyl)-1,6-dihydro-3-pyridinecarboxylic acid and 3R-quinuclidine dihydrochloride in the same manner as in Example 1-4 and Method 2.

$^1$H-NMR (CDCl$_3$,500 MHz) δ7.96 (s, 1H), 7.87 (d, 1H), 7.54 (s, 1H), 7.36 (d, 1H), 7.22 (d, 1H), 7.02 (br, d, 1H), 6.49 (d, 1H), 4.01 (m, 1H), 3.23 (m, 1H), 2.77 (m, 4H), 2.54 (m, 1H), 1.89 (m, 1H), 1.63 (m, 3H), 1.37 (m, 1H)

Example 27

Synthesis of N-[(3S)-1-azabicyclo[2.2.2]octan-3-yl]-1-(2,4-dichlorophenyl)-6-oxo-3-pyridinecarboxamide

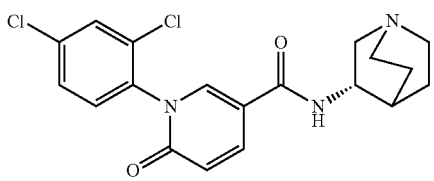 [SMILES: O=C(N[C@@H]1CN2CCC1CC2)c1ccc(=O)n(-c2ccc(Cl)cc2Cl)c1]

6-Oxo-1-(2,4-dichlorophenyl)-1,6-dihydro-3-pyridinecarboxylic acid was synthesized in the same manner as in Example 1-2 and Example 1-3, except that 2,4-dichloroaniline was used as a starting material. A target compound was obtained from the synthesized 6-oxo-1-(2,4-dichlorophenyl)-1,6-dihydro-3-pyridinecarboxylic acid and 3S-quinuclidine dihydrochloride in the same manner as in Example 1-4 and Method 2.

$^1$H-NMR (CDCl$_3$,500 MHz) δ7.96 (s, 1H), 7.87 (d, 1H), 7.54 (s, 1H), 7.36 (d, 1H), 7.22 (d, 1H), 7.02 (br, d, 1H), 6.49 (d, 1H), 4.01 (m, 1H), 3.23 (m, 1H), 2.77 (m, 4H), 2.54 (m, 1H), 1.89 (m, 1H), 1.63 (m, 3H), 1.37 (m, 1H)

Example 28

Synthesis of N-(1-azabicyclo[2.2.2]octan-3-yl)-1-(3-chloro-4-methoxyphenyl)-6-oxo-3-pyridinecarboxamide

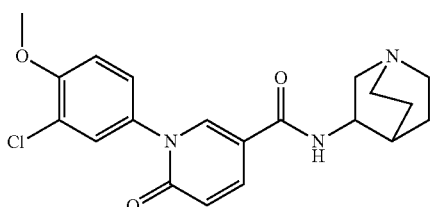

A target compound was obtained in the same manner as in Example 1 and Method 2, except that 3-chloro-4-methoxyaniline was used as a starting material.

$^1$H-NMR (CDCl$_3$,200 MHz) δ8.07 (s, 1H), 7.70 (d, 1H), 7.41 (m, 1H), 7.26 (m, 1H), 7.03 (d, 1H), 6.64 (d, 1H), 6.23 (br, d, 1H), 4.05 (m, 1H), 3.97 (s, 3H), 3.42 (m, 1H), 2.87 (m, 4H), 2.59 (m, 1H), 2.04 (m, 1H), 1.80 (m, 3H), 1.56 (m, 1H)

Example 29

Synthesis of N-(1-azabicyclo[2.2.2]octan-3-yl)-1-(2-chloro-4-methylphenyl)-6-oxo-3-pyridinecarboxamide

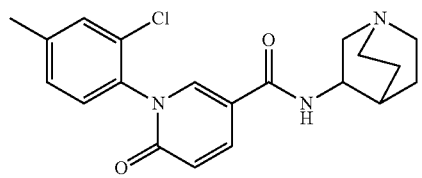 [SMILES: Cc1ccc(-n2cc(C(=O)NC3CN4CCC3CC4)ccc2=O)c(Cl)c1]

A target compound was obtained in the same manner as in Example 1 and Method 2, except that 2-chloro-4-methylaniline was used as a starting material.

$^1$H-NMR (CDCl$_3$,500 MHz) δ7.97 (s, 1H), 7.87 (d, 1H), 7.27 (s, 1H), 7.20 (m, 2H), 7.00 (br, d, 1H), 6.45 (d, 1H), 3.98 (m, 1H), 3.18 (m, 1H), 2.72 (m, 4H), 2.53 (m, 1H), 2.03 (s, 3H), 1.86 (m, 1H), 1.60 (m, 3H), 1.35 (m, 1H)

Example 30

Synthesis of N-(1-azabicyclo[2.2.2]octan-3-yl)-1-(2,5-difluorophenyl)-6-oxo-3-pyridinecarboxamide

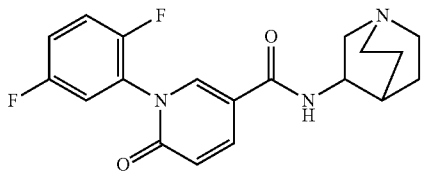 [SMILES: O=C(NC1CN2CCC1CC2)c1ccc(=O)n(-c2cc(F)ccc2F)c1]

A target compound was obtained in the same manner as in Example 1 and Method 1, except that 2,5-difluoroaniline was used as a starting material.

$^1$H-NMR (CDCl$_3$,500 MHz) δ8.02 (m, 1H), 7.75 (d, 1H), 7.17 (m, 3H), 6.65 (d, 1H), 6.25 (br, 1H), 4.11 (m, 1H), 3.41 (m, 1H), 2.85 (m, 4H), 2.66 (m, 1H), 2.04 (m, 1H), 1.84 (m, 3H), 1.63 (m, 1H)

Example 31

Synthesis of N-(1-azabicyclo[2.2.2]octan-3-yl)-1-(3,5-dichlorophenyl)-6-oxo-3-pyridinecarboxamide

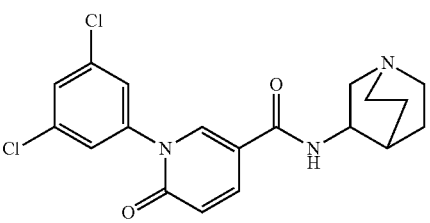 [SMILES: O=C(NC1CN2CCC1CC2)c1ccc(=O)n(-c2cc(Cl)cc(Cl)c2)c1]

A target compound was obtained in the same manner as in Example 1 and Method 1, except that 3,5-dichloroaniline was used as a starting material.

¹H-NMR (CDCl₃,500 MHz) δ8.03 (s, 1H), 7.70 (d, 1H), 7.47 (s, 1H), 7.32 (s, 2H), 6.71 (d, 1H), 6.07 (br, 1H), 4.10 (m, 1H), 3.43 (m, 1H), 2.85 (m, 4H), 2.56 (m, 1H), 2.02 (m, 1H), 1.71 (m, 3H), 1.46 (m, 1H)

Example 32

Synthesis of N-(1-azabicyclo[2.2.2]octan-3-yl)-1-(2,4-dimethylphenyl)-6-oxo-3-pyridinecarboxamide

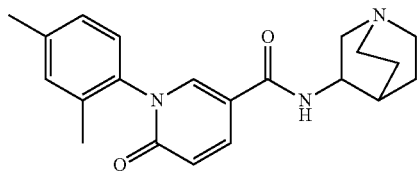 [SMILES: Cc1ccc(-n2cc(C(=O)NC3CN4CCC3CC4)ccc2=O)c(C)c1]

A target compound was obtained in the same manner as in Example 1 and Method 1, except that 2,4-dimethylaniline was used as a starting material.

¹H-NMR (CDCl₃,500 MHz) δ7.96 (s, 1H), 7.81 (d, 1H), 7.18 (m, 3H), 6.63 (d, 1H), 6.10 (br, 1H), 4.13 (m, 1H), 3.47 (m, 1H), 3.05 (m, 1H), 2.95 (m, 4H), 2.38 (s, 3H), 2.12 (s, 3H), 1.97 (m, 1H), 1.51 (m, 3H), 1.40 (m, 1H)

Example 33

N-(1-azabicyclo[2.2.2]octan-3-yl)-1-(2-chloro-4-methylphenyl)-6-oxo-3-pyridinecarboxamide

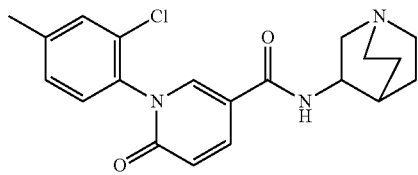 [SMILES: Cc1ccc(-n2cc(C(=O)NC3CN4CCC3CC4)ccc2=O)c(Cl)c1]

A target compound was obtained in the same manner as in Example 1 and Method 2, except that 2-chloro-4-methylaniline was used as a starting material.

¹H-NMR (CDCl₃,500 MHz) δ8.02 (d, 1H), 7.91 (m, 1H), 7.37 (s, 1H), 7.18 (m, 2H), 7.02 (br, 1H), 6.64 (m, 1H), 4.21 (m, 1H), 3.23 (m, 1H), 2.95 (m, 5H), 2.40 (s, 3H), 2.12 (m, 1H), 1.85 (m, 3H), 1.49 (m, 1H)

Example 34

Synthesis of N-(1-azabicyclo[2.2.2]octan-3-yl)-1-(2,4-difluorophenyl)-6-oxo-3-pyridinecarboxamide

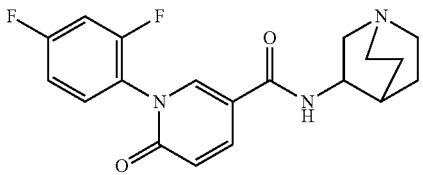 [SMILES: O=C(NC1CN2CCC1CC2)c1ccc(=O)n(-c2ccc(F)cc2F)c1]

A target compound was obtained in the same manner as in Example 1 and Method 1, except that 2,4-difluoroaniline was used as a starting material.

¹H-NMR (CDCl₃,500 MHz) δ8.03 (s, 1H), 7.76 (m, 1H), 7.34 (m, 1H), 7.05 (m, 2H), 6.65 (d, 1H), 6.51 (br, 1H), 4.12 (m, 1H), 3.49 (m, 1H), 3.22 (m, 1H), 2.83 (m, 4H), 2.02 (m, 1H), 1.78 (m, 3H), 1.62 (m, 1H)

Example 35

Synthesis of N-(1-azabicyclo[2.2.2]octan-3-yl)-1-(2-chloro-5-methylphenyl)-6-oxo-3-pyridinecarboxamide

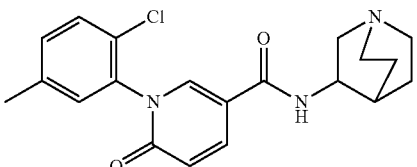

A target compound was obtained in the same manner as in Example 1 and Method 1, except that 1-chloro-5-methylaniline was used as a starting material.

¹H-NMR (CDCl₃,500 MHz) δ7.95 (m, 1H), 7.79 (d, 1H), 7.43 (d, 1H), 7.22 (s, 1H), 7.16 (s, 1H), 6.67 (d, 1H), 6.32 (br, 1H), 4.15 (m, 1H), 3.41 (m, 1H), 2.85 (m, 4H), 2.73 (d, 1H), 2.37 (s, 3H), 2.05 (m, 1H), 1.72 (m, 3H), 1.48 (m, 1H)

Example 36

Synthesis of N-(1-azabicyclo[2.2.2]octan-3-yl)-1-(4-tert-butyl-2-chlorophenyl)-6-oxo-3-pyridinecarboxamide

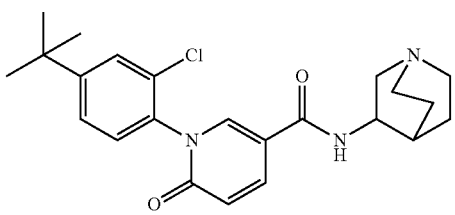 [SMILES: CC(C)(C)c1ccc(-n2cc(C(=O)NC3CN4CCC3CC4)ccc2=O)c(Cl)c1]

A target compound was obtained in the same manner as in Example 1 and Method 1, except that 4-tert-butyl-2-chloroaniline was used as a starting material.

¹H-NMR (CDCl₃,500 MHz) δ7.94 (m, 1H), 7.82 (d, 1H), 7.54 (d, 1H), 7.33 (d, 1H), 7.23 (t, 1H), 6.61 (d, 1H), 6.57 (br,

1H), 4.07 (m, 1H), 3.29 (m, 1H), 2.84 (m, 4H), 2.60 (m, 1H), 1.87 (m, 1H), 1.68 (m, 3H), 1.40 (m, 1H), 1.34 (s, 9H)

Example 37

Synthesis of N-(1-azabicyclo[2.2.2]octan-3-yl)-1-(2-chloro-4-fluorophenyl)-6-oxo-3-pyridinecarboxamide

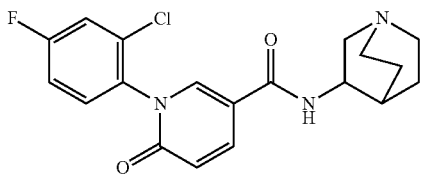 [SMILES: O=C(NC1CN2CCC1CC2)c1ccc(=O)n(-c2ccc(F)cc2Cl)c1]

A target compound was obtained in the same manner as in Example 1 and Method 1, except that 2-chloro-4-fluoroaniline was used as a starting material.
$^1$H-NMR (CDCl$_3$, 500 MHz) δ8.09 (s, 1H), 7.91 (d, 1H), 7.73 (m, 2H), 7.33 (m, 1H), 6.67 (d, 1H), 6.11 (br, 1H), 4.10 (m, 1H), 3.39 (m, 1H), 2.81 (m, 4H), 2.56 (m, 1H), 1.72 (m, 4H), 1.49 (m, 1H)

Example 38

Synthesis of N-(1-azabicyclo[2.2.2]octan-3-yl)-1-(4-chloro-2-fluorophenyl)-6-oxo-3-pyridinecarboxamide

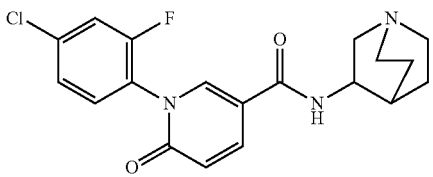 [SMILES: O=C(NC1CN2CCC1CC2)c1ccc(=O)n(-c2ccc(Cl)cc2F)c1]

A target compound was obtained in the same manner as in Example 1 and Method 1, except that 4-chloro-2-fluoroaniline was used as a starting material.
$^1$H-NMR (CDCl$_3$, 500 MHz) δ7.98 (s, 1H), 7.72 (d, 1H), 7.31 (m, 3H), 6.62 (d, 1H), 6.14 (br, 1H), 4.09 (m, 1H), 3.47 (m, 1H), 3.36 (m, 1H), 2.86 (m, 3H), 2.56 (m, 1H), 2.07 (s, 1H), 1.72 (m, 3H), 1.53 (m, 1H)

Example 39

Synthesis of N-(1-azabicyclo[2.2.2]octan-3-yl)-1-(3,4-dimethoxyphenyl)-6-oxo-3-pyridinecarboxamide

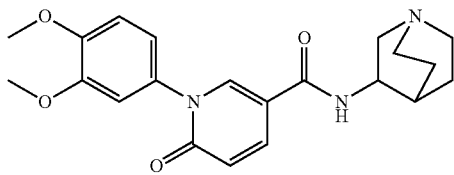 [SMILES: COc1ccc(-n2cc(C(=O)NC3CN4CCC3CC4)ccc2=O)cc1OC]

A target compound was obtained in the same manner as in Example 1 and Method 1, except that 3,4-dimethoxyaniline was used as a starting material.
$^1$H-NMR (CDCl$_3$, 500 MHz) δ8.10 (s, 1H), 7.73 (d, 1H), 6.91 (m, 3H), 6.57 (d, 1H), 6.33 (br, 1H), 4.10 (d, 1H), 3.95 (m, 3H), 3.91 (m, 3H), 3.37 (m, 1H), 2.81 (m, 4H), 2.55 (m, 1H), 2.04 (m, 1H), 1.68 (m, 3H), 1.49 (m, 1H)

Example 40

Synthesis of N-(1-azabicyclo[2.2.2]octan-3-yl)-1-(3,4-dichlorophenyl)-6-oxo-3-pyridinecarboxamide

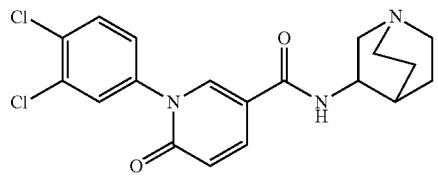 [SMILES: O=C(NC1CN2CCC1CC2)c1ccc(=O)n(-c2ccc(Cl)c(Cl)c2)c1]

A target compound was obtained in the same manner as in Example 1 and Method 1, except that 3,4-dichloroaniline was used as a starting material.
$^1$H-NMR (CDCl$_3$, 500 MHz) δ8.07 (s, 1H), 7.74 (d, 1H), 7.55 (m, 2H), 7.23 (m, 1H), 6.59 (m, 1H), 6.42 (br, 1H), 4.12 (m, 1H), 3.38 (m, 1H), 2.83 (m, 4H), 2.63 (m, 1H), 2.03 (m, 1H), 1.73 (m, 2H), 1.49 (m, 1H)

Example 41

Synthesis of N-(1-azabicyclo[2.2.2]octan-3-yl)-1-(3,4-difluorophenyl)-6-oxo-3-pyridinecarboxamide

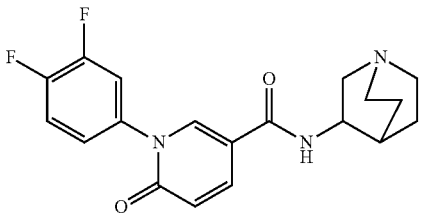 [SMILES: O=C(NC1CN2CCC1CC2)c1ccc(=O)n(-c2ccc(F)c(F)c2)c1]

A target compound was obtained in the same manner as in Example 1 and Method 1, except that 3,4-difluoroaniline was used as a starting material.
$^1$H-NMR (CDCl$_3$, 500 MHz) δ8.08 (s, 1H), 7.72 (d, 1H), 7.32 (m, 2H), 7.16 (m, 1H), 6.65 (d, 1H), 6.29 (br, 1H), 4.10 (m, 1H), 3.40 (m, 1H), 2.87 (m, 4H), 2.53 (m, 1H), 1.98 (m, 1H), 1.67 (m, 3H), 1.48 (m, 1H)

Example 42

Synthesis of N-(1-azabicyclo[2.2.2]octan-3-yl)-1-(4-chloro-3-methylphenyl)-6-oxo-3-pyridinecarboxamide

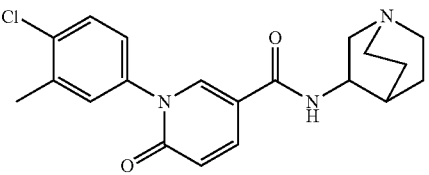 [SMILES: Cc1cc(-n2cc(C(=O)NC3CN4CCC3CC4)ccc2=O)ccc1Cl]

A target compound was obtained in the same manner as in Example 1 and Method 1, except that 4-chloro-3-methylaniline was used as a starting material.

¹H-NMR (CDCl₃, 500 MHz) δ8.02 (s, 1H), 7.62 (d, 1H), 7.42 (d, 1H), 7.28 (s, 1H), 7.18 (m, 1H), 6.63 (d, 1H), 6.01 (br, 1H), 4.06 (m, 1H), 3.42 (m, 1H), 2.80 (m, 4H), 2.59 (m, 1H), 2.42 (s, 3H), 1.97 (m, 1H), 1.63 (m, 3H), 1.48 (m, 1H)

Example 43

Synthesis of N-(1-azabicyclo[2.2.2]octan-3-yl)-1-(3,5-difluorophenyl)-6-oxo-3-pyridinecarboxamide

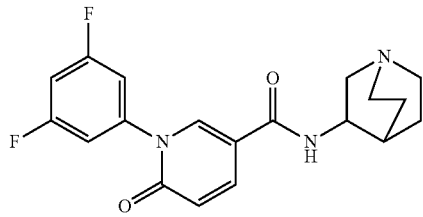 [SMILES: O=C(NC1CN2CCC1CC2)c1ccc(=O)n(-c2cc(F)cc(F)c2)c1]

A target compound was obtained in the same manner as in Example 1 and Method 1, except that 3,5-difluoroaniline was used as a starting material.

¹H-NMR (CDCl₃, 500 MHz) δ8.45 (m, 1H), 8.42 (s, 1H), 8.15 (m, 1H), 7.10 (m, 2H), 6.86 (m, 1H), 6.59 (d, 1H), 4.57 (m, 1H), 4.17 (m, 1H), 3.99 (m, 1H), 3.52 (m, 1H), 3.29 (m, 2H), 3.11 (m, 1H), 2.50 (m, 1H), 2.48 (m, 1H), 2.08 (m, 2H), 1.83 (m, 1H)

Example 44

Synthesis of N-(1-azabicyclo[2.2.2]octan-3-yl)-1-(4-fluoro-2-methylphenyl)-6-oxo-3-pyridinecarboxamide

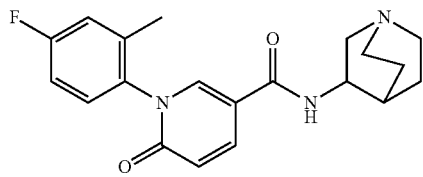

A target compound was obtained in the same manner as in Example 1 and Method 1, except that 4-fluoro-2-methylaniline was used as a starting material.

¹H-NMR (CDCl₃, 500 MHz) δ7.94 (s, 1H), 7.71 (d, 1H), 7.16 (m, 1H), 7.05 (m, 2H), 6.65 (d, 1H), 6.05 (br, 1H), 4.09 (m, 1H), 3.42 (m, 1H), 2.88 (m, 4H), 2.56 (m, 1H), 2.14 (s, 3H), 1.67 (m, 4H), 1.52 (m, 1H)

Example 45

Synthesis of N-(1-azabicyclo[2.2.2]octan-3-yl)-1-(2,5-dimethoxyphenyl)-6-oxo-3-pyridinecarboxamide

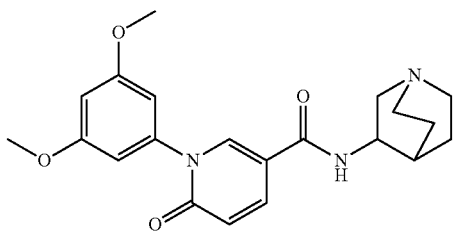 [SMILES: COc1cc(OC)cc(-n2cc(C(=O)NC3CN4CCC3CC4)ccc2=O)c1]

A target compound was obtained in the same manner as in Example 1 and Method 2, except that 2,5-dimethoxyaniline was used as a starting material.

¹H-NMR (CDCl₃, 500 MHz) δ8.06 (s, 1H), 7.74 (d, 1H), 6.57 (d, 1H), 6.52 (d, 1H), 6.50 (m, 2H), 4.08 (m, 1H), 3.79 (s, 6H), 3.37 (m, 1H), 2.95 (m, 4H), 2.60 (m, 1H), 1.98 (m, 1H), 1.66 (m, 3H), 1.48 (m, 1H)

Example 46

Synthesis of N-(1-azabicyclo[2.2.2]octan-3-yl)-1-(2,3-dichlorophenyl)-6-oxo-3-pyridinecarboxamide

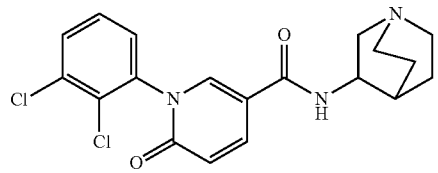 [SMILES: O=C(NC1CN2CCC1CC2)c1ccc(=O)n(-c2cccc(Cl)c2Cl)c1]

A target compound was obtained in the same manner as in Example 1 and Method 1, except that 2,3-dichloroaniline was used as a starting material.

¹H-NMR (CDCl₃, 500 MHz) δ7.99 (s, 1H), 7.80 (d, 1H), 7.61 (d, 1H), 7.38 (m, 2H), 6.63 (d, 1H), 6.29 (br, 1H), 4.08 (m, 1H), 3.42 (m, 1H), 2.85 (m, 5H), 2.08 (m, 1H), 1.82 (m, 3H), 1.59 (m, 1H)

Example 47

Synthesis of N-(1-azabicyclo[2.2.2]octan-3-yl)-1-(3-chloro-2-methoxyphenyl)-6-oxo-3-pyridinecarboxamide

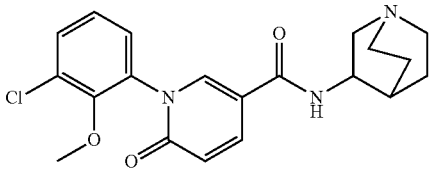 [SMILES: COc1c(Cl)cccc1-n1cc(C(=O)NC2CN3CCC2CC3)ccc1=O]

A target compound was obtained in the same manner as in Example 1 and Method 1, except that 3-chloro-2-methoxyaniline was used as a starting material.

¹H-NMR (CDCl₃, 500 MHz) δ7.97 (s, 1H), 7.81 (d, 1H), 7.52 (d, 1H), 7.21 (m, 2H), 6.72 (d, 1H), 6.21 (br, 1H), 4.14 (m, 1H), 3.84 (s, 3H), 3.41 (m, 1H), 2.98 (m, 4H), 2.68 (m, 1H), 2.03 (s, 1H), 1.68 (m, 3H), 1.45 (m, 1H)

Example 48

Synthesis of N-(1-azabicyclo[2.2.2]octan-3-yl)-1-(3-fluoro-4-methoxyphenyl)-6-oxo-3-pyridinecarboxamide

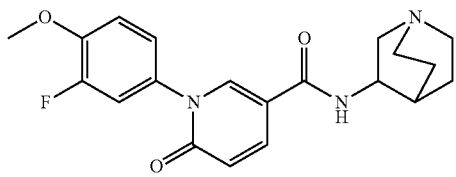

A target compound was obtained in the same manner as in Example 1 and Method 1, except that 3-fluoro-4-methoxyaniline was used as a starting material.
¹H-NMR (CDCl₃, 500 MHz) δ8.09 (s, 1H), 7.69 (d, 1H), 7.03 (m, 3H), 6.60 (d, 1H), 6.21 (br, 1H), 4.09 (m, 1H), 3.92 (s, 3H), 3.40 (m, 1H), 2.94 (m, 4H), 2.60 (m, 1H), 2.01 (m, 1H), 1.85 (m, 3H), 1.49 (m, 1H)

Example 49

Synthesis of N-(1-azabicyclo[2.2.2]octan-3-yl)-1-(2,4-dimethoxyphenyl)-6-oxo-3-pyridinecarboxamide

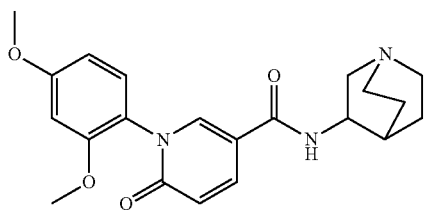 [SMILES: COc1ccc(-n2cc(C(=O)NC3CN4CCC3CC4)ccc2=O)c(OC)c1]

A target compound was obtained in the same manner as in Example 1 and Method 1, except that 2,4-dimethoxyaniline was used as a starting material.
¹H-NMR (CDCl₃, 500 MHz) δ7.95 (s, 1H), 7.72 (d, 1H), 7.18 (m, 1H), 6.61 (m, 3H), 6.17 (br, 1H), 4.12 (m, 1H), 3.85 (s, 3H), 3.79 (s, 3H), 3.42 (m, 1H), 2.92 (m, 4H), 2.60 (m, 1H), 1.90 (m, 1H), 1.73 (m, 3H), 1.41 (m, 1H)

Example 50

Synthesis of N-(1-azabicyclo[2.2.2]octan-3-yl)-1-(3-chloro-4-fluorophenyl)-6-oxo-3-pyridinecarboxamide

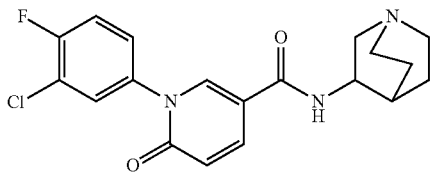 [SMILES: O=C(NC1CN2CCC1CC2)c1ccc(=O)n(-c2ccc(F)c(Cl)c2)c1]

A target compound was obtained in the same manner as in Example 1 and Method 1, except that 3-chloro-4-fluoroaniline was used as a starting material.
¹H-NMR (CDCl₃, 500 MHz) δ8.02 (s, 1H), 7.68 (d, 1H), 7.51 (d, 1H), 7.37 (m, 2H), 6.63 (d, 1H), 6.02 (br, 1H), 4.05 (m, 1H), 3.42 (m, 1H), 2.85 (m, 4H), 2.58 (m, 1H), 2.02 (m, 1H), 1.72 (m, 3H), 1.56 (m, 1H)

Example 51

Synthesis of N-(1-azabicyclo[2.2.2]octan-3-yl)-1-(4-chloro-3-methoxyphenyl)-6-oxo-3-pyridinecarboxamide

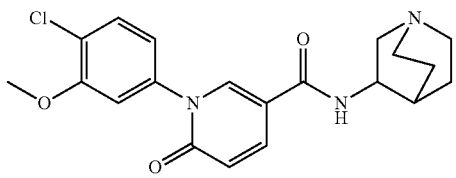 [SMILES: COc1cc(-n2cc(C(=O)NC3CN4CCC3CC4)ccc2=O)ccc1Cl]

A target compound was obtained in the same manner as in Example 1 and Method 1, except that 4-chloro-3-methoxyaniline was used as a starting material.
¹H-NMR (CDCl₃, 500 MHz) δ8.03 (s, 1H), 7.77 (d, 1H), 7.62 (d, 1H), 6.97 (m, 2H), 6.60 (d, 1H), 6.42 (br, 1H), 4.18 (m, 1H), 3.89 (s, 3H), 3.41 (m, 1H), 2.87 (m, 5H), 2.18 (m, 1H), 1.80 (m, 3H), 1.58 (m, 1H)

Example 52

Synthesis of N-(1-azabicyclo[2.2.2]octan-3-yl)-1-(2-methoxy-5-methylphenyl)-6-oxo-3-pyridinecarboxamide

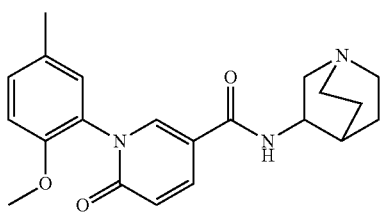 [SMILES: COc1ccc(C)cc1-n1cc(C(=O)NC2CN3CCC2CC3)ccc1=O]

A target compound was obtained in the same manner as in Example 1 and Method 1, except that 2-methoxy-5-methylaniline was used as a starting material.
¹H-NMR (CDCl₃, 500 MHz) δ8.02 (s, 1H), 7.81 (d, 1H), 7.23 (m, 1H), 7.12 (s, 1H), 6.79 (d, 1H), 6.63 (br, 1H), 6.60 (d, 1H), 4.20 (m, 1H), 3.78 (s, 3H), 3.72 (m, 1H), 3.20 (m, 1H), 2.88 (m, 4H), 2.38 (s, 3H), 2.18 (s, 1H), 1.82 (m, 3H), 1.59 (m, 1H)

Example 53

Synthesis of N-(1-azabicyclo[2.2.2]octan-3-yl)-1-(4-chloro-2-methylphenyl)-6-oxo-3-pyridinecarboxamide

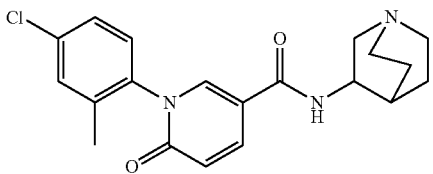 [SMILES: Cc1cc(Cl)ccc1-n1cc(C(=O)NC2CN3CCC2CC3)ccc1=O]

A target compound was obtained in the same manner as in Example 1 and Method 1, except that 4-chloro-2-methylaniline was used as a starting material.

$^1$H-NMR (CDCl$_3$, 500 MHz) δ8.01 (s, 1H), 7.81 (d, 1H), 7.37 (m, 2H), 7.14 (d, 1H), 6.78 (d, 1H), 6.48 (br, 1H), 4.15 (m, 1H), 3.49 (m, 1H), 3.05 (m, 1H), 2.89 (m, 4H), 2.17 (s, 3H), 2.10 (m, 1H), 1.80 (m, 3H), 1.63 (m, 1H)

Example 54

Synthesis of N-(1-azabicyclo[2.2.2]octan-3-yl)-1-(4-methoxy-2-methylphenyl)-6-oxo-3-pyridinecarboxamide

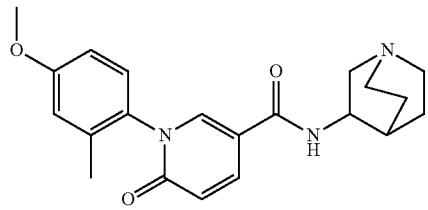 [SMILES: COc1ccc(-n2cc(C(=O)NC3CN4CCC3CC4)ccc2=O)c(C)c1]

A target compound was obtained in the same manner as in Example 1 and Method 1, except that 4-methoxy-2-methylaniline was used as a starting material.

$^1$H-NMR (CDCl$_3$, 500 MHz) δ8.01 (s, 1H), 7.85 (d, 1H), 7.06 (d, 1H), 6.79 (m, 3H), 6.58 (d, 1H), 4.20 (m, 1H), 3.79 (s, 3H), 3.44 (m, 1H), 3.05 (m, 1H), 2.90 (m, 4H), 2.09 (s, 3H), 2.07 (m, 1H), 1.81 (m, 3H), 1.59 (m, 1H)

Example 55

Synthesis of N-(1-azabicyclo[2.2.2]octan-3-yl)-1-[4-chloro-3-(trifluoromethyl)phenyl]-6-oxo-3-pyridinecarboxamide

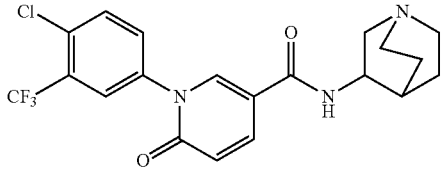 [SMILES: O=C(NC1CN2CCC1CC2)c1ccc(=O)n(-c2ccc(Cl)c(C(F)(F)F)c2)c1]

A target compound was obtained in the same manner as in Example 1 and Method 1, except that 4-chloro-3-(trifluoromethyl)aniline was used as a starting material.

$^1$H-NMR (CDCl$_3$, 500 MHz) δ8.07 (s, 1H), 7.72 (m, 3H), 7.53 (m, 1H), 6.65 (d, 1H), 6.09 (br, 1H), 4.13 (m, 1H), 3.48 (m, 1H), 2.89 (m, 4H), 2.57 (m, 1H), 2.01 (m, 1H), 1.78 (m, 2H), 1.69 (m, 1H), 1.43 (m, 1H)

Example 56

Synthesis of N-(1-azabicyclo[2.2.2]octan-3-yl)-1-(5-chloro-2-methoxyphenyl)-6-oxo-3-pyridinecarboxamide

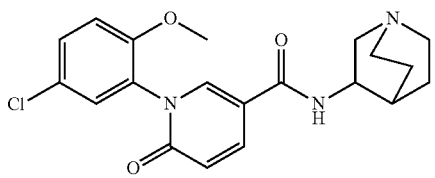 [SMILES: COc1ccc(Cl)cc1-n1cc(C(=O)NC2CN3CCC2CC3)ccc1=O]

A target compound was obtained in the same manner as in Example 1 and Method 1, except that 5-chloro-2-methoxyaniline was used as a starting material.

$^1$H-NMR (CDCl$_3$, 500 MHz) δ7.91 (s, 1H), 7.70 (d, 1H), 7.42 (d, 1H), 7.26 (s, 1H), 7.00 (d, 1H), 6.61 (d, 1H), 6.06 (br, 1H), 4.10 (m, 1H), 3.80 (s, 3H), 3.37 (m, 1H), 2.88 (m, 4H), 2.57 (m, 1H), 1.98 (m, 1H), 1.67 (m, 3H), 1.42 (m, 1H)

Example 57

Synthesis of N-(1-azabicyclo[2.2.2]octan-3-yl)-1-[2-chloro-4-(trifluoromethoxy)phenyl]-6-oxo-3-pyridinecarboxamide

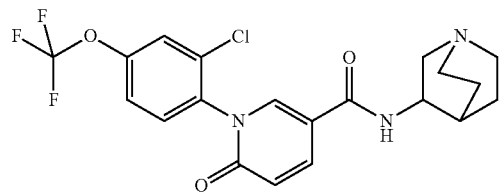 [SMILES: O=C(NC1CN2CCC1CC2)c1ccc(=O)n(-c2ccc(OC(F)(F)F)cc2Cl)c1]

A target compound was obtained in the same manner as in Example 1 and Method 2, except that 2-chloro-4-(trifluoromethoxy)aniline was used as a starting material.

$^1$H-NMR (CDCl$_3$, 500 MHz) δ7.95 (s, 1H), 7.82 (d, 1H), 7.47 (s, 1H), 7.41 (d, 1H), 7.30 (d, 1H), 6.63 (d, 1H), 6.50 (br, d, 1H), 4.11 (m, 1H), 3.36 (m, 1H), 2.87 (m, 4H), 2.62 (m, 1H), 2.00 (m, 1H), 1.71 (m, 3H), 1.50 (m, 1H)

Example 58

Synthesis of N-(1-azabicyclo[2.2.2]octan-3-yl)-1-(4-chloro-3-fluorophenyl)-6-oxo-3-pyridinecarboxamide

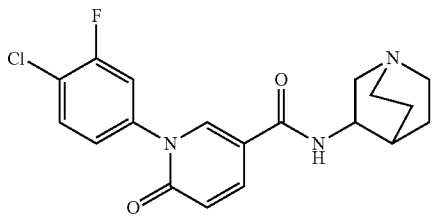 [SMILES: O=C(NC1CN2CCC1CC2)c1ccc(=O)n(-c2ccc(Cl)c(F)c2)c1]

A target compound was obtained in the same manner as in Example 1 and Method 1, except that 4-chloro-3-fluorophenylaniline was used as a starting material.

¹H-NMR (CDCl₃, 500 MHz) δ8.09 (s, 1H), 7.73 (d, 1H), 7.51 (t, 1H), 7.25 (m, 1H), 7.15 (d, 1H), 6.62 (d, 1H), 6.29 (br, 1H), 4.13 (m, 1H), 3.47 (m, 1H), 2.86 (m, 4H), 2.65 (d, 1H), 2.02 (m, 1H), 1.95 (m, 1H), 1.71 (m, 2H), 1.54 (m, 1H)

Example 59

Synthesis of N-(1-azabicyclo[2.2.2]octan-3-yl)-1-(2,4,5-trimethoxyphenyl)-6-oxo-3-pyridinecarboxamide

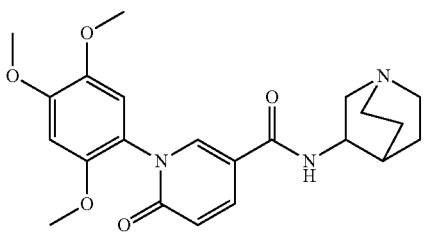 [SMILES: COc1cc(OC)c(-n2cc(C(=O)NC3CN4CCC3CC4)ccc2=O)cc1OC]

A target compound was obtained in the same manner as in Example 1 and Method 1, except that 2,4,5-trimethoxyaniline was used as a starting material.

¹H-NMR (CDCl₃, 500 MHz) δ8.09 (s, 1H), 7.69 (d, 1H), 6.65 (d, 1H), 6.56 (s, 2H), 6.07 (br, 1H), 4.11 (m, 1H), 3.87 (m, 9H), 3.43 (m, 1H), 2.82 (m, 4H), 2.59 (m, 1H), 2.01 (m, 1H), 1.69 (m, 3H), 1.54 (m, 1H)

Example 60

Synthesis of N-(1-azabicyclo[2.2.2]octan-3-yl)-1-(2,4,5-trichlorophenyl)-6-oxo-3-pyridinecarboxamide

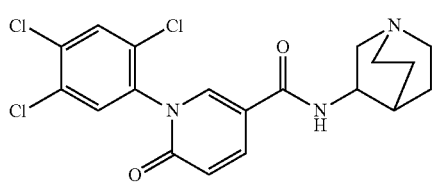 [SMILES: O=C(NC1CN2CCC1CC2)c1ccc(=O)n(-c2cc(Cl)c(Cl)cc2Cl)c1]

A target compound was obtained in the same manner as in Example 1 and Method 1, except that 2,4,5-trichloroaniline was used as a starting material.

¹H-NMR (CDCl₃, 500 MHz) δ7.93 (s, 1H), 7.78 (d, 1H), 7.69 (s, 1H), 7.49 (s, 1H), 6.68 (d, 1H), 6.22 (br, 1H), 4.13 (m, 1H), 3.42 (m, 1H), 2.88 (m, 4H), 2.67 (m, 1H), 1.78 (m, 3H), 1.65 (m, 1H), 1.47 (m, 1H)

Example 61

Synthesis of N-(1-azabicyclo[2.2.2]octan-3-yl)-1-(3,4,5-trifluorophenyl)-6-oxo-3-pyridinecarboxamide

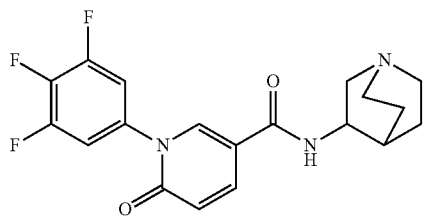 [SMILES: O=C(NC1CN2CCC1CC2)c1ccc(=O)n(-c2cc(F)c(F)c(F)c2)c1]

A target compound was obtained in the same manner as in Example 1 and Method 1, except that 3,4,5-trifluoroaniline was used as a starting material.

¹H-NMR (CDCl₃, 500 MHz) δ8.07 (s, 1H), 7.78 (d, 1H), 7.18 (m, 2H), 6.58 (m, 2H), 4.09 (m, 1H), 3.67 (m, 1H), 3.40 (m, 1H), 2.83 (m, 3H), 2.57 (m, 1H), 1.99 (m, 1H), 1.68 (m, 3H), 1.51 (m, 1H)

Example 62

Synthesis of N-(1-azabicyclo[2.2.2]octan-3-yl)-6-oxo-1-(3-phenylphenyl)-3-pyridinecarboxamide

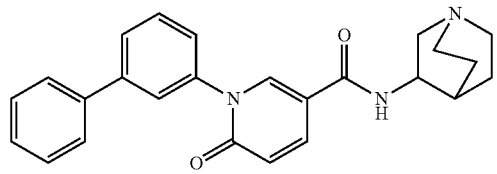 [SMILES: O=C(NC1CN2CCC1CC2)c1ccc(=O)n(-c2cccc(-c3ccccc3)c2)c1]

A target compound was obtained in the same manner as in Example 1 and Method 2, except that 3-phenylaniline was used as a starting material.

¹H-NMR (CDCl₃, 500 MHz) δ7.78 (s, 1H), 7.63 (d, 1H), 7.45 (m, 3H), 7.22 (m, 6H), 6.57 (br, d, 1H), 6.28 (d, 1H), 3.90 (m, 1H), 3.19 (m, 1H), 2.71 (m, 4H), 2.42 (m, 1H), 1.80 (m, 1H), 1.57 (m, 3H), 1.30 (m, 1H)

Example 63

Synthesis of N-(1-azabicyclo[2.2.2]octan-3-yl)-6-oxo-1-(2-phenylmethoxyphenyl)-3-pyridinecarboxamide

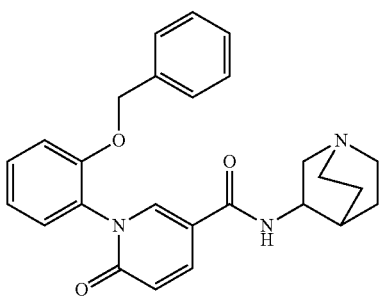 [SMILES: O=C(NC1CN2CCC1CC2)c1ccc(=O)n(-c2ccccc2OCc2ccccc2)c1]

A target compound was obtained in the same manner as in Example 1 and Method 2, except that 2-phenylmethoxyaniline was used as a starting material.

$^1$H-NMR (CDCl$_3$, 500 MHz) δ8.03 (s, 1H), 7.80 (d, 1H), 7.23 (m, 7H), 7.02 (m, 2H), 6.92 (br, d, 1H), 6.44 (d, 1H), 5.04 (s, 2H), 4.01 (m, 1H), 3.24 (m, 1H), 2.75 (m, 4H), 2.55 (m, 1H), 1.89 (m, 1H), 1.63 (m, 3H), 1.33 (m, 1H)

Example 64

Synthesis of N-(1-azabicyclo[2.2.2]octan-3-yl)-6-oxo-1-(2-phenylphenyl)-3-pyridinecarboxamide

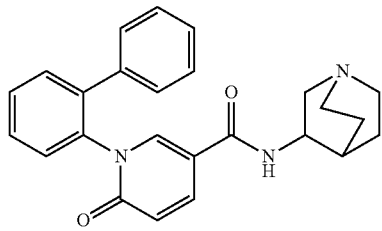 [SMILES: O=C(NC1CN2CCC1CC2)c1ccc(=O)n(-c2ccccc2-c2ccccc2)c1]

A target compound was obtained in the same manner as in Example 1 and Method 2, except that 2-phenylaniline was used as a starting material.

$^1$H-NMR (CDCl$_3$, 500 MHz) δ7.78 (s, 1H), 7.63 (d, 1H), 7.44 (m, 3H), 7.20 (m, 6H), 6.57 (br, d, 1H), 6.28 (d, 1H), 3.90 (m, 1H), 3.19 (m, 1H), 2.76 (m, 4H), 2.41 (m, 1H), 1.80 (m, 1H), 1.57 (m, 3H), 1.30 (m, 1H)

Example 65

Synthesis of N-(1-azabicyclo[2.2.2]octan-3-yl)-1-(4-phenylphenyl)-6-oxo-3-pyridinecarboxamide

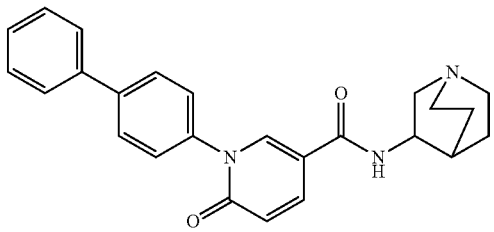 [SMILES: O=C(NC1CN2CCC1CC2)c1ccc(=O)n(-c2ccc(-c3ccccc3)cc2)c1]

A target compound was obtained in the same manner as in Example 1 and Method 1, except that 4-phenylaniline was used as a starting material.

$^1$H-NMR (CDCl$_3$, 500 MHz) δ8.16 (s, 1H), 7.72 (m, 3H), 7.62 (m, 2H), 7.49 (m, 4H), 7.42 (m, 1H), 6.67 (m, 1H), 6.14 (br, 1H), 4.12 (m, 1H), 3.42 (m, 1H), 2.86 (m, 4H), 2.58 (m, 1H), 2.02 (m, 1H), 1.72 (m, 1H), 1.53 (m, 1H)

Example 66

Synthesis of N-(1-azabicyclo[2.2.2]octan-3-yl)-1-(2-methoxy-5-phenylphenyl)-6-oxo-3-pyridinecarboxamide

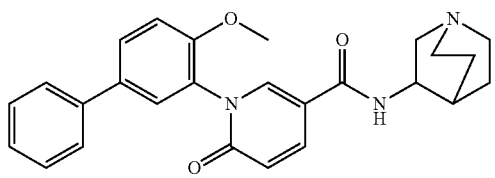 [SMILES: COc1ccc(-c2ccccc2)cc1-n1cc(C(=O)NC2CN3CCC2CC3)ccc1=O]

A target compound was obtained in the same manner as in Example 1 and Method 1, except that 2-methoxy-5-phenylaniline was used as a starting material.

$^1$H-NMR (CDCl$_3$, 500 MHz) δ8.02 (s, 1H), 7.71 (m, 2H), 7.57 (m, 2H), 7.51 (m, 1H), 7.48 (m, 2H), 7.35 (m, 1H), 7.14 (m, 1H), 6.67 (m, 1H), 6.02 (br, 1H), 4.12 (m, 1H), 3.88 (s, 3H), 3.45 (m, 1H), 2.85 (m, 4H), 2.58 (m, 1H), 2.02 (m, 1H), 1.73 (m, 3H), 1.56 (m, 1H)

Example 67

Synthesis of N-(1-azabicyclo[2.2.2]octan-3-yl)-1-[4-(4-chlorophenyl)phenyl]-6-oxo-3-pyridinecarboxamide

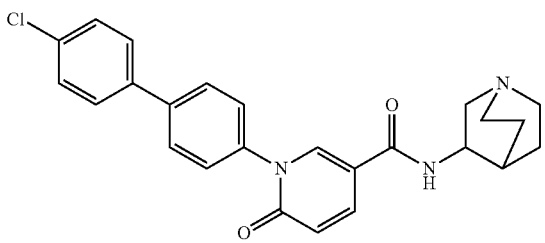 [SMILES: O=C(NC1CN2CCC1CC2)c1ccc(=O)n(-c2ccc(-c3ccc(Cl)cc3)cc2)c1]

A target compound was obtained in the same manner as in Example 1 and Method 1, except that 4-(4-chlorophenyl)aniline was used as a starting material.

$^1$H-NMR (CDCl$_3$, 500 MHz) δ8.15 (s, 1H), 7.69 (m, 3H), 7.56 (m, 2H), 7.45 (m, 4H), 6.68 (m, 1H), 6.03 (br, 1H), 4.13 (m, 1H), 3.43 (m, 1H), 2.86 (m, 4H), 2.56 (m, 1H), 2.03 (m, 1H), 1.73 (m, 1H), 1.56 (m, 1H)

Example 68

Synthesis of N-(1-azabicyclo[2.2.2]octan-3-yl)-1-[4-(4-methoxyphenyl)phenyl]-6-oxo-3-pyridinecarboxamide

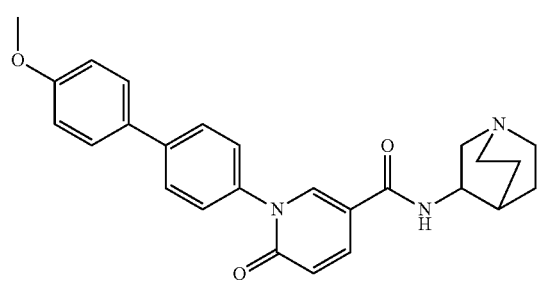 [SMILES: COc1ccc(-c2ccc(-n3cc(C(=O)NC4CN5CCC4CC5)ccc3=O)cc2)cc1]

A target compound was obtained in the same manner as in Example 1 and Method 1, except that 4-(4-methoxyphenyl)aniline was used as a starting material.

¹H-NMR (CDCl₃, 500 MHz) δ8.15 (s, 1H), 7.70 (m, 3H), 7.57 (m, 2H), 7.45 (m, 2H), 7.03 (m, 2H), 6.70 (m, 1H), 6.03 (br, 1H), 4.13 (m, 1H), 3.89 (s, 3H), 3.45 (m, 1H), 2.84 (m, 4H), 2.58 (m, 1H), 2.02 (m, 1H), 1.74 (m, 3H), 1.65 (m, 1H)

Example 69

Synthesis of N-(1-azabicyclo[2.2.2]octan-3-yl)-1-[4-(4-methylphenyl)phenyl]-6-oxo-3-pyridinecarboxamide

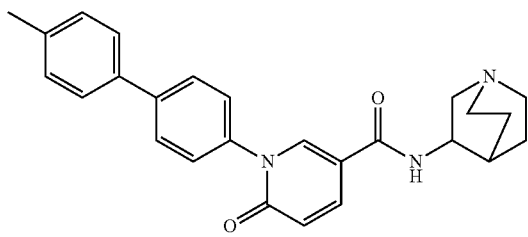 [SMILES: Cc1ccc(-c2ccc(-n3cc(C(=O)NC4CN5CCC4CC5)ccc3=O)cc2)cc1]

A target compound was obtained in the same manner as in Example 1 and Method 1, except that 4-(4-methylphenyl)aniline was used as a starting material.

¹H-NMR (CDCl₃, 500 MHz) δ8.15 (s, 1H), 7.71 (m, 3H), 7.53 (m, 2H), 7.46 (m, 2H), 7.31 (m, 2H), 6.69 (m, 1H), 6.60 (br, 1H), 4.13 (m, 1H), 3.43 (m, 1H), 2.84 (m, 4H), 2.56 (m, 1H), 2.43 (s, 3H), 2.03 (m, 1H), 1.73 (m, 3H), 1.57 (m, 1H)

Example 70

Synthesis of N-(1-azabicyclo[2.2.2]octan-3-yl)-1-(2-chloro-4-phenylphenyl)-6-oxo-3-pyridinecarboxamide

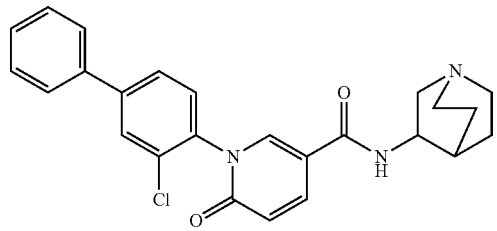 [SMILES: O=C(NC1CN2CCC1CC2)c1ccc(=O)n(-c2ccc(-c3ccccc3)cc2Cl)c1]

A target compound was obtained in the same manner as in Example 1 and Method 1, except that 2-chloro-4-phenylaniline was used as a starting material.

¹H-NMR (CDCl₃, 500 MHz) δ8.65 (s, 1H), 8.39 (m, 1H), 8.34 (m, 1H), 7.74 (m, 1H), 7.59 (m, 3H), 7.48 (m, 3H), 7.41 (m, 1H), 6.68 (d, 1H), 4.06 (m, 1H), 3.48 (m, 1H), 3.13 (m, 4H), 2.51 (m, 1H), 2.05 (m, 1H), 1.77 (m, 3H), 1.51 (m, 1H)

Example 71

Synthesis of N-(1-azabicyclo[2.2.2]octan-3-yl)-1-[4-(4-chlorophenoxy)phenyl]-6-oxo-3-pyridinecarboxamide

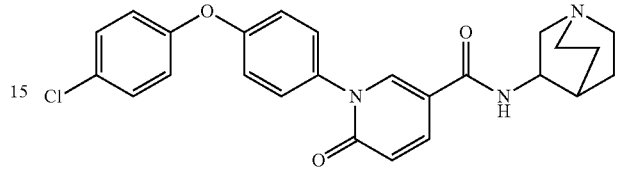

A target compound was obtained in the same manner as in Example 1 and Method 1, except that 4-(4-chlorophenoxy)aniline was used as a starting material.

¹H-NMR (CDCl₃, 500 MHz) δ8.15 (s, 1H), 7.78 (d, 1H), 7.45 (m, 3H), 7.10 (m, 2H), 7.04 (m, 3H), 6.68 (d, 1H), 6.38 (br, 1H), 4.17 (m, 1H), 3.42 (m, 1H), 3.08 (m, 1H), 2.88 (m, 4H), 2.09 (m, 1H), 1.78 (m, 3H), 1.64 (m, 1H)

Example 72

Synthesis of N-(1-azabicyclo[2.2.2]octan-3-yl)-1-[4-(4-methylphenoxy)phenyl]-6-oxo-3-pyridinecarboxamide

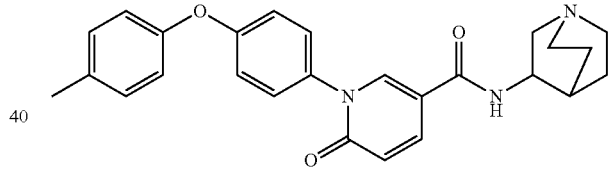

A target compound was obtained in the same manner as in Example 1 and Method 1, except that 4-(4-methylphenoxy)aniline was used as a starting material.

¹H-NMR (CDCl₃, 500 MHz) δ8.15 (s, 1H), 7.73 (m, 1H), 7.32 (m, 2H), 7.22 (m, 1H), 7.08 (m, 3H), 7.02 (m, 2H), 6.63 (d, 1H), 6.58 (br, 1H), 4.15 (m, 1H), 3.42 (m, 1H), 3.01 (m, 1H), 2.91 (m, 3H), 2.72 (m, 1H), 2.36 (s, 3H), 2.04 (m, 1H), 1.74 (m, 3H), 1.55 (m, 1H)

Example 73

Synthesis of N-(1-azabicyclo[2.2.2]octan-3-yl)-6-oxo-1-(4-phenoxyphenyl)-3-pyridinecarboxamide

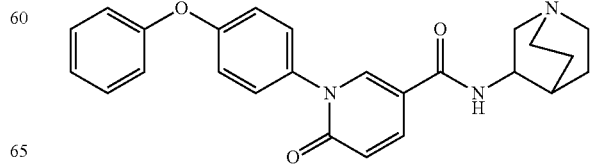

A target compound was obtained in the same manner as in Example 1 and Method 2, except that 4-phenoxyaniline was used as a starting material.

¹H-NMR (CDCl₃, 500 MHz) δ8.14 (s, 1H), 8.85 (d, 1H), 7.34 (m, 3H), 7.15 (m, 2H), 7.14 (br, s, 1H), 7.01 (m, 4H), 6.46 (d, 1H), 4.04 (m, 1H), 3.23 (m, 1H), 2.76 (m, 4H), 2.64 (m, 1H), 1.93 (m, 1H), 1.64 (m, 3H), 1.37 (m, 1H)

Example 74

Synthesis of N-(1-azabicyclo[2.2.2]octan-3-yl)-6-oxo-1-(2-phenoxyphenyl)-3-pyridinecarboxamide

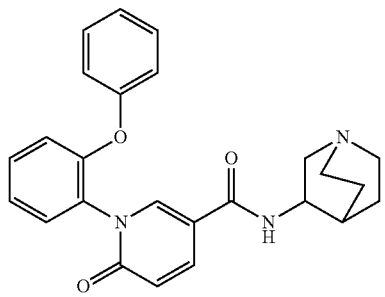

A target compound was obtained in the same manner as in Example 1 and Method 2, except that 2-phenoxyaniline was used as a starting material.

¹H-NMR (CDCl₃, 500 MHz) δ8.06 (s, 1H), 7.75 (d, 1H), 7.35 (m, 1H), 7.27 (m, 3H), 7.15 (m, 1H), 7.08 (m, 1H), 6.95 (m3H), 6.64 (br, 1H), 6.42 (d, 1H), 4.02 (m, 1H), 3.23 (m, 1H), 2.75 (m, 4H), 2.53 (m, 1H), 1.91 (m, 1H), 1.62 (m, 3H), 1.35 (m, 1H)

Example 75

Synthesis of N-(1-azabicyclo[2.2.2]octan-3-yl)-1-(4-ethynylphenyl)-6-oxo-3-pyridinecarboxamide

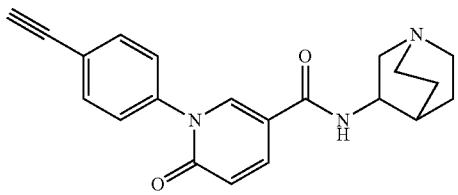 [SMILES: C#Cc1ccc(-n2cc(C(=O)NC3CN4CCC3CC4)ccc2=O)cc1]

A target compound was obtained in the same manner as in Example 1 and Method 2, except that 4-ethynyl aniline was used as a starting material.

¹H-NMR (CDCl₃, 500 MHz) δ8.09 (s, 1H), 7.80 (d, 1H), 7.53 (d, 2H), 7.26 (d, 2H), 6.95 (br, d, 1H), 6.49 (d, 1H), 4.04 (m, 1H), 3.26 (m, 1H), 3.18 (s, 1H), 2.76 (m, 4H), 2.60 (m, 1H), 1.93 (s, 3H), 1.86 (m, 1H), 1.64 (m, 3H), 1.41 (m, 1H)

Example 76

Synthesis of N-(1-azabicyclo[2.2.2]octan-3-yl)-1-[4-(methylthio)phenyl]-6-oxo-3-pyridinecarboxamide

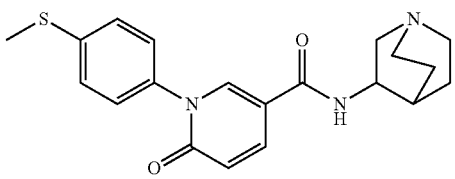 [SMILES: CSc1ccc(-n2cc(C(=O)NC3CN4CCC3CC4)ccc2=O)cc1]

A target compound was obtained in the same manner as in Example 1 and Method 2, except that 4-(methylthio)aniline was used as a starting material.

¹H-NMR (CDCl₃, 200 MHz) δ8.06 (s, 1H), 7.80 (d, 1H), 7.13 (m, 4H), 7.05 (br, d, 1H), 6.43 (d, 1H), 4.03 (m, 1H), 3.23 (m, 1H), 2.74 (m, 4H), 2.54 (m, 1H), 2.46 (s, 3H), 1.90 (m, 1H), 1.63 (m, 3H), 1.38 (m, 1H)

Example 77

Synthesis of N-(1-azabicyclo[2.2.2]octan-3-yl)-1-[2-(methylthio)phenyl]-6-oxo-3-pyridinecarboxamide

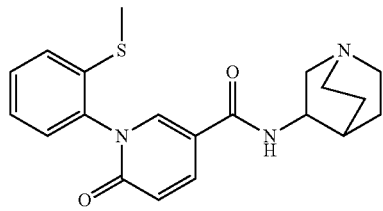 [SMILES: CSc1ccccc1-n1cc(C(=O)NC2CN3CCC2CC3)ccc1=O]

A target compound was obtained in the same manner as in Example 1 and Method 2, except that 2-(methylthio)aniline was used as a starting material.

¹H-NMR (CDCl₃, 500 MHz) δ7.94 (s, 1H), 7.86 (d, 1H), 7.42 (m, 1H), 7.33 (m, 1H), 7.23 (m, 1H), 7.13 (m, 1H), 7.11 (br, d, 1H), 6.49 (d, 1H), 3.99 (m, 1H), 3.20 (m, 1H), 2.75 (m, 4H), 2.53 (m, 1H), 2.37 (s, 3H), 1.89 (m, 1H), 1.63 (m, 3H), 1.33 (m, 1H)

Example 78

Synthesis of N-[(3R)-1-azabicyclo[2.2.2]octan-3-yl]-1-[2-(methylthio)phenyl]-6-oxo-3-pyridinecarboxamide

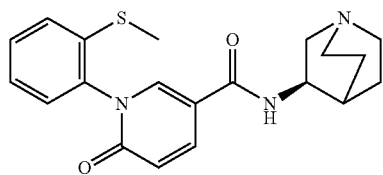 [SMILES: CSc1ccccc1-n1cc(C(=O)N[C@H]2CN3CCC2CC3)ccc1=O]

6-Oxo-1-(2-(methylthio)phenyl)-1,6-dihydro-3-pyridinecarboxylic acid was synthesized in the same manner as in Example 1-2 and Example 1-3, except that 2-(methylthio) aniline was used as a starting material. A target compound was obtained from the synthesized 6-oxo-1-(2-(methylthio) phenyl)-1,6-dihydro-3-pyridinecarboxylic acid and 3R-aminoquinuclidine dihydrochloride in the same manner as in Example 1-4 and Method 1.

¹H-NMR (CDCl₃, 500 MHz) δ7.94 (s, 1H), 7.86 (d, 1H), 7.42 (m, 1H), 7.33 (m, 1H), 7.23 (m, 1H), 7.13 (m, 1H), 7.11 (br, d, 1H), 6.49 (d, 1H), 3.99 (m, 1H), 3.20 (m, 1H), 2.75 (m, 4H), 2.53 (m, 1H), 2.37 (s, 3H), 1.89 (m, 1H), 1.63 (m, 3H), 1.33 (m, 1H)

Example 79

Synthesis of N-[(3S)-1-azabicyclo[2.2.2]octan-3-yl]-1-[2-(methylthio)phenyl]-6-oxo-3-pyridinecarboxamide

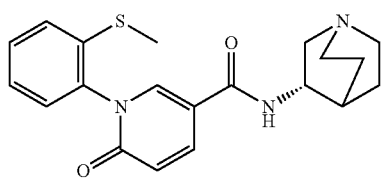 [SMILES: CSc1ccccc1-n1cc(C(=O)N[C@@H]2CN3CCC2CC3)ccc1=O]

6-Oxo-1-(2-(methylthio)phenyl)-1,6-dehydro-3-pyridinecarboxylic acid was synthesized in the same manner as in Example 1-2 and Example 1-3, except that 2-(methylthio) aniline was used as a starting material. A target compound was obtained from the synthesized 6-oxo-1-(2-(methylthio) phenyl)-1,6-dihydro-3-pyridinecarboxylic acid and 3S-aminoquinuclidine dihydrochloride in the same manner as in Example 1-4 and Method 1.

¹H-NMR (CDCl₃, 500 MHz) δ7.94 (s, 1H), 7.86 (d, 1H), 7.42 (m, 1H), 7.33 (m, 1H), 7.23 (m, 1H), 7.13 (m, 1H), 7.11 (br, d, 1H), 6.49 (d, 1H), 3.99 (m, 1H), 3.20 (m, 1H), 2.75 (m, 4H), 2.53 (m, 1H), 2.37 (s, 3H), 1.89 (m, 1H), 1.63 (m, 3H), 1.33 (m, 1H)

Example 80

Synthesis of N-(1-azabicyclo[2.2.2]octan-3-yl)-1-[2-(ethylthio)phenyl]-6-oxo-3-pyridinecarboxamide

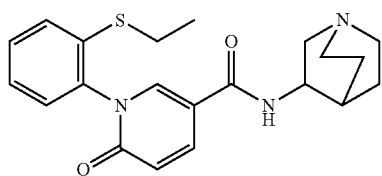 [SMILES: CCSc1ccccc1-n1cc(C(=O)NC2CN3CCC2CC3)ccc1=O]

A target compound was obtained in the same manner as in Example 1 and Method 1, except that 2-(ethylthio)aniline was used as a starting material.

¹H-NMR (CDCl₃, 500 MHz) δ7.95 (s, 1H), 7.84 (m, 1H), 7.43 (m, 2H), 7.32 (m, 1H), 7.23 (m, 1H), 6.65 (br, 1H), 6.59 (d, 1H), 4.12 (m, 1H), 3.35 (m, 1H), 2.92 (m, 1H), 2.87 (m, 5H), 2.67 (m, 1H), 2.01 (m, 1H), 1.72 (m, 3H), 1.53 (m, 1H), 1.29 (t, 3H)

Example 81

Synthesis of N-(1-azabicyclo[2.2.2]octan-3-yl)-6-oxo-1-[2-(propan-2-ylthio)phenyl]-3-pyridinecarboxamide

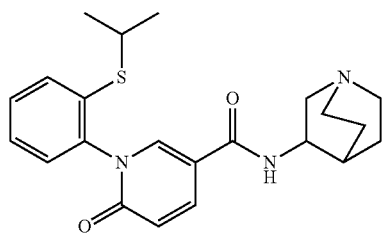 [SMILES: CC(C)Sc1ccccc1-n1cc(C(=O)NC2CN3CCC2CC3)ccc1=O]

A target compound was obtained in the same manner as in Example 1 and Method 1, except that 2-(propan-2-ylthio) aniline was used as a starting material.

¹H-NMR (CDCl₃, 500 MHz) δ7.95 (s, 1H), 7.84 (d, 1H), 7.56 (m, 1H), 7.41 (m, 1H), 7.34 (m, 1H), 7.22 (m, 1H), 6.72 (br, 1H), 6.55 (d, 1H), 4.04 (m, 1H), 3.34 (m, 2H), 2.81 (m, 4H), 2.51 (m, 1H), 1.94 (m, 1H), 1.67 (m, 3H), 1.40 (m, 1H), 1.23 (m, 6H)

Example 82

Synthesis of N-(1-azabicyclo[2.2.2]octan-3-yl)-6-oxo-1-[2-(phenylmethylthio)phenyl]-3-pyridinecarboxamide

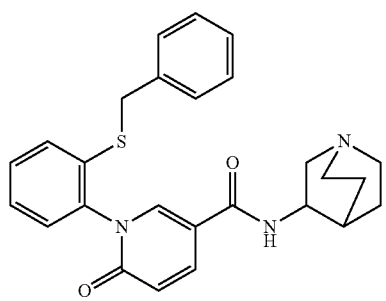 [SMILES: O=C(NC1CN2CCC1CC2)c1ccc(=O)n(-c2ccccc2SCc2ccccc2)c1]

A target compound was obtained in the same manner as in Example 1 and Method 1, except that 2-(phenylmethylthio) aniline was used as a starting material.

¹H-NMR (CDCl₃, 500 MHz) δ7.79 (m, 3H), 7.45 (m, 1H), 7.37 (m, 3H), 7.23 (m, 4H), 6.66 (d, 1H), 6.32 (br, 1H), 4.18 (m, 1H), 4.06 (s, 2H), 3.47 (m, 1H), 3.06 (m, 1H), 2.89 (m, 4H), 2.08 (m, 1H), 1.78 (m, 3H), 1.56 (m, 1H)

Example 83

Synthesis of N-(1-azabicyclo[2.2.2]octan-3-yl)-1-[2-(methylthio)-5-(trifluoromethyl)phenyl]-6-oxo-3-pyridinecarboxamide

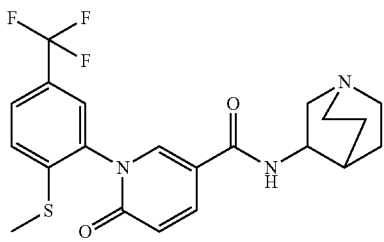 [SMILES: CSc1ccc(C(F)(F)F)cc1-n1cc(C(=O)NC2CN3CCC2CC3)ccc1=O]

A target compound was obtained in the same manner as in Example 1 and Method 1, except that 2-(methylthio)-5-(trifluoromethyl)aniline was used as a starting material.

$^1$H-NMR (CDCl$_3$, 500 MHz) δ7.93 (s, 1H), 7.89 (d, 1H), 7.78 (m, 1H), 7.50 (m, 1H), 7.43 (m, 1H), 6.67 (m, 1H), 6.15 (br, 1H), 4.13 (m, 1H), 3.41 (m, 1H), 2.94 (m, 1H), 2.89 (m, 3H), 2.83 (m, 1H), 2.47 (s, 3H), 2.03 (m, 1H), 1.72 (m, 3H), 1.54 (m, 1H)

Example 84

Synthesis of N-(1-azabicyclo[2.2.2]octan-3-yl)-1-[4-methoxy-2-(methylthio)phenyl]-6-oxo-3-pyridinecarboxamide

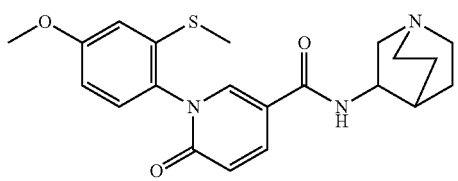 [SMILES: COc1ccc(-n2cc(C(=O)NC3CN4CCC3CC4)ccc2=O)c(SC)c1]

A target compound was obtained in the same manner as in Example 1 and Method 1, except that 4-methoxy-2-(methylthio)phenylaniline was used as a starting material.

$^1$H-NMR (CDCl$_3$, 500 MHz) δ7.97 (s, 1H), 7.74 (m, 1H), 7.18 (m, 1H), 6.87 (m, 1H), 6.79 (m, 1H), 6.69 (d, 1H), 6.10 (br, 1H), 4.05 (m, 1H), 3.88 (s, 3H), 3.42 (m, 1H), 2.87 (m, 4H), 2.65 (m, 1H), 2.42 (s, 3H), 2.05 (m, 1H), 1.73 (m, 3H), 1.58 (m, 1H)

Example 85

Synthesis of N-(1-azabicyclo[2.2.2]octan-3-yl)-1-[2-(ethylthio)-4-methoxyphenyl]-6-oxo-3-pyridinecarboxamide

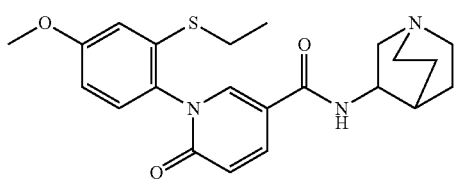 [SMILES: CCSc1cc(OC)ccc1-n1cc(C(=O)NC2CN3CCC2CC3)ccc1=O]

A target compound was obtained in the same manner as in Example 1 and Method 1, except that 2-(ethylthio)-4-methoxyaniline was used as a starting material.

$^1$H-NMR (CDCl$_3$, 500 MHz) δ7.95 (s, 1H), 7.75 (d, 1H), 7.23 (d, 1H), 7.01 (s, 1H), 6.87 (d, 1H), 6.69 (d, 1H), 6.03 (br, 1H), 4.13 (m, 1H), 3.97 (s, 3H), 3.49 (m, 1H), 2.92 (m, 4H), 2.83 (m, 2H), 2.61 (m, 1H), 2.04 (m, 1H), 1.73 (m, 3H), 1.56 (m, 1H), 1.33 (t, 3H)

Example 86

Synthesis of N-(1-azabicyclo[2.2.2]octan-3-yl)-1-[4-chloro-2-(methylthio)phenyl]-6-oxo-3-pyridinecarboxamide

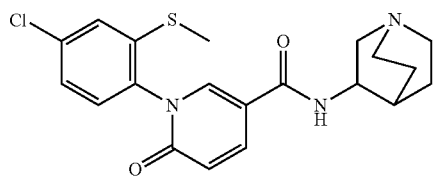 [SMILES: CSc1cc(Cl)ccc1-n1cc(C(=O)NC2CN3CCC2CC3)ccc1=O]

A target compound was obtained in the same manner as in Example 1 and Method 1, except that 4-chloro-2-(methylthio)aniline was used as a starting material.

$^1$H-NMR (CDCl$_3$, 500 MHz) δ7.94 (s, 1H), 7.86 (d, 1H), 7.26 (s, 1H), 7.21 (d, 1H), 7.10 (d, 1H), 6.88 (br, d, 1H), 6.55 (d, 1H), 4.05 (m, 1H), 3.28 (m, 1H), 2.79 (m, 4H), 2.62 (m, 1H), 2.41 (s, 3H), 1.95 (m, 1H), 1.68 (m, 3H), 1.42 (m, 1H)

Example 87

Synthesis of N-[(3R)-1-azabicyclo[2.2.2]octan-3-yl]-1-[4-chloro-2-(methylthio)phenyl]-6-oxo-3-pyridinecarboxamide

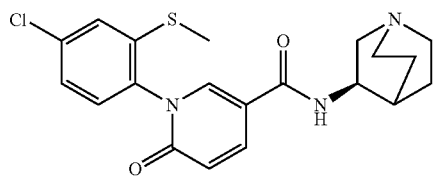 [SMILES: CSc1cc(Cl)ccc1-n1cc(C(=O)N[C@H]2CN3CCC2CC3)ccc1=O]

6-oxo-1-(4-chloro-2-(methylthio)phenyl)-1,6-dihydro-3-pyridinecarboxylic acid was synthesized in the same manner as in Example 1-2 and Example 1-3, except that 4-chloro-2-(methylthio)aniline was used as a starting material. A target compound was obtained from the synthesized 6-oxo-1-(4-chloro-2-(methylthio)phenyl)-1,6-dihydro-3-pyridinecarboxylic acid and 3R-aminoquinuclidine dihydrochloride in the same manner as in Example 1-4 and Method 1.

$^1$H-NMR (CDCl$_3$, 500 MHz) δ7.94 (s, 1H), 7.86 (d, 1H), 7.26 (s, 1H), 7.21 (d, 1H), 7.10 (d, 1H), 6.88 (br, d, 1H), 6.55 (d, 1H), 4.05 (m, 1H), 3.28 (m, 1H), 2.79 (m, 4H), 2.62 (m, 1H), 2.41 (s, 3H), 1.95 (m, 1H), 1.68 (m, 3H), 1.42 (m, 1H)

Example 88

Synthesis of N-[(3S)-1-azabicyclo[2.2.2]octan-3-yl]-1-[4-chloro-2-(methylthio)phenyl]-6-oxo-3-pyridinecarboxamide

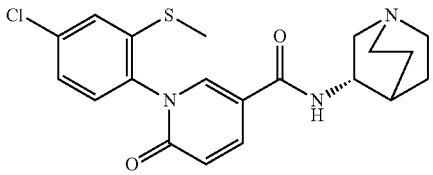 [SMILES: CSc1cc(Cl)ccc1-n1cc(C(=O)N[C@@H]2CN3CCC2CC3)ccc1=O]

6-oxo-1-(4-chloro-2-(methylthio)phenyl)-1,6-dihydro-3-pyridinecarboxylic acid was synthesized in the same manner as in Example 1-2 and Example 1-3, except that 4-chloro-2-(methylthio)aniline was used as a starting material. A target compound was obtained from the synthesized 6-oxo-1-(4-chloro-2-(methylthio)phenyl)-1,6-dihydro-3-pyridinecarboxylic acid and 3S-aminoquinuclidine dihydrochloride in the same manner as in Example 1-4 and Method 1.

$^1$H-NMR (CDCl$_3$, 500 MHz) δ7.94 (s, 1H), 7.86 (d, 1H), 7.26 (s, 1H), 7.21 (d, 1H), 7.10 (d, 1H), 6.88 (br, d, 1H), 6.55 (d, 1H), 4.05 (m, 1H), 3.28 (m, 1H), 2.79 (m, 4H), 2.62 (m, 1H), 2.41 (s, 3H), 1.95 (m, 1H), 1.68 (m, 3H), 1.42 (m, 1H)

Example 89

Synthesis of N-(1-azabicyclo[2.2.2]octan-3-yl)-1-[4-methyl-2-(methylthio)phenyl]-6-oxo-3-pyridinecarboxamide

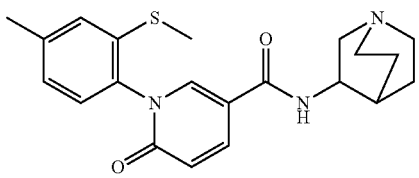 [SMILES: CSc1cc(C)ccc1-n1cc(C(=O)NC2CN3CCC2CC3)ccc1=O]

A target compound was obtained in the same manner as in Example 1 and Method 1, except that 4-methyl-2-(methylthio)aniline was used as a starting material.

$^1$H-NMR (CDCl$_3$, 500 MHz) δ7.93 (s, 1H), 7.81 (d, 1H), 7.16 (s, 1H), 7.07 (s, 2H), 6.58 (m, 2H), 4.08 (m, 1H), 3.36 (m, 1H), 2.84 (m, 4H), 2.64 (s, 3H), 2.61 (s, 3H), 1.97 (m, 1H), 1.73 (m, 3H), 1.53 (m, 1H)

Example 90

Synthesis of N-[(3R)-1-azabicyclo[2.2.2]octan-3-yl]-1-[4-methyl-2-(methylthio)phenyl]-6-oxo-3-pyridinecarboxamide

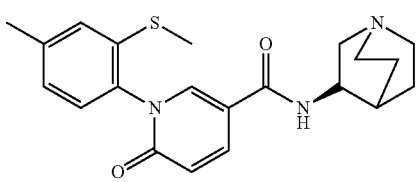

6-oxo-1-(4-methyl-2-(methylthio)phenyl)-1,6-dihydro-3-pyridinecarboxylic acid was synthesized in the same manner as in Example 1-2 and Example 1-3, except that 4-methyl-2-(methylthio)aniline was used as a starting material. A target compound was obtained from the synthesized 6-oxo-1-(4-methyl-2-(methylthio)phenyl)-1,6-dihydro-3-pyridinecarboxylic acid and 3R-aminoquinuclidine dihydrochloride in the same manner as in Example 1-4 and Method 1.

$^1$H-NMR (CDCl$_3$, 500 MHz) δ7.93 (s, 1H), 7.81 (d, 1H), 7.16 (s, 1H), 7.07 (s, 2H), 6.58 (m, 2H), 4.08 (m, 1H), 3.36 (m, 1H), 2.84 (m, 4H), 2.64 (s, 3H), 2.61 (s, 3H), 1.97 (m, 1H), 1.73 (m, 3H), 1.53 (m, 1H)

Example 91

Synthesis of N-[(3S)-1-azabicyclo[2.2.2]octan-3-yl]-1-[4-methyl-2-(methylthio)phenyl]-6-oxo-3-pyridinecarboxamide

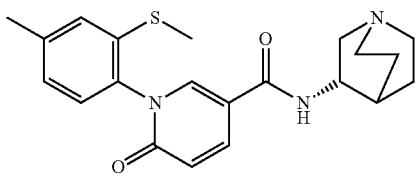

6-oxo-1-(4-methyl-2-(methylthio)phenyl)-1,6-dihydro-3-pyridinecarboxylic acid was synthesized in the same manner as in Example 1-2 and Example 1-3, except that 4-chloro-2-(methylthio)aniline was used as a starting material. A target compound was obtained from the synthesized 6-oxo-1-(4-methyl-2-(methylthio)phenyl)-1,6-dihydro-3-pyridinecarboxylic acid and 3S-aminoquinuclidine dihydrochloride in the same manner as in Example 1-4 and Method 1.

$^1$H-NMR (CDCl$_3$, 500 MHz) δ7.93 (s, 1H), 7.81 (d, 1H), 7.16 (s, 1H), 7.07 (s, 2H), 6.58 (m, 2H), 4.08 (m, 1H), 3.36 (m, 1H), 2.84 (m, 4H), 2.64 (s, 3H), 2.61 (s, 3H), 1.97 (m, 1H), 1.73 (m, 3H), 1.53 (m, 1H)

Example 92

Synthesis of N-(1-azabicyclo[2.2.2]octan-3-yl)-1-[4-tert-butyl-2-(methylthio)phenyl]-6-oxo-3-pyridinecarboxamide

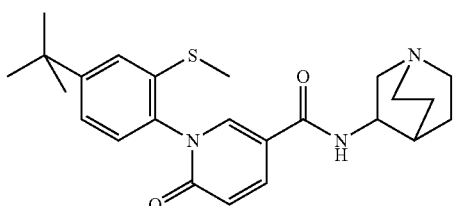

A target compound was obtained in the same manner as in Example 1 and Method 1, except that 4-tert-butyl-2-(methylthio)aniline was used as a starting material.

$^1$H-NMR (CDCl$_3$, 500 MHz) δ7.98 (s, 1H), 7.92 (m, 1H), 7.40 (m, 1H), 7.32 (m, 1H), 7.16 (m, 1H), 6.90 (br, 1H), 6.61 (d, 1H), 4.27 (m, 1H), 3.46 (m, 1H), 3.22 (m, 1H), 2.98 (m, 4H), 2.41 (s, 3H), 2.13 (s, 1H), 1.95 (m, 3H), 1.62 (m, 1H), 1.35 (s, 9H)

Example 93

Synthesis of N-(1-azabicyclo[2.2.2]octan-3-yl)-1-[4-chloro-2-(propan-2-ylthio)phenyl]-6-oxo-3-pyridinecarboxamide

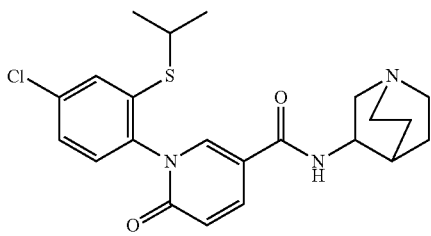 [SMILES: CC(C)Sc1cc(Cl)ccc1-n1cc(C(=O)NC2CN3CCC2CC3)ccc1=O]

A target compound was obtained in the same manner as in Example 1 and Method 1, except that 4-chloro-2-(propan-2-ylthio)aniline was used as a starting material.

$^1$H-NMR (CDCl$_3$, 500 MHz) δ7.93 (s, 1H), 7.82 (d, 1H), 7.51 (m, 1H), 7.32 (m, 1H), 7.22 (m, 1H), 6.68 (d, 1H), 6.38 (br, 1H), 4.19 (m, 1H), 3.45 (m, 2H), 3.09 (m, 1H), 2.91 (m, 4H), 2.09 (m, 1H), 1.81 (m, 3H), 1.76 (m, 1H), 1.28 (m, 6H)

Example 94

Synthesis of N-(1-azabicyclo[2.2.2]octan-3-yl)-1-[2-(methylthio)-4-propylphenyl]-6-oxo-3-pyridinecarboxamide

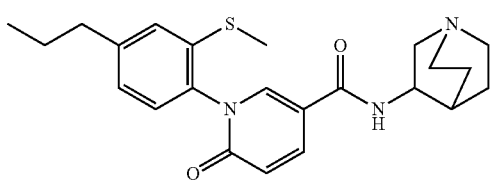 [SMILES: CCCc1ccc(-n2cc(C(=O)NC3CN4CCC3CC4)ccc2=O)c(SC)c1]

A target compound was obtained in the same manner as in Example 1 and Method 1, except that 2-(methylthio)-4-propylaniline was used as a starting material.

$^1$H-NMR (CDCl$_3$, 500 MHz) δ7.92 (s, 1H), 7.90 (m, 1H), 7.18 (m, 1H), 7.07 (m, 3H), 6.57 (br, 1H), 4.29 (m, 1H), 3.53 (m, 1H), 3.23 (m, 1H), 3.02 (m, 4H), 2.63 (m, 2H), 2.39 (s, 3H), 2.18 (m, 1H), 1.97 (m, 1H), 1.86 (m, 2H), 1.68 (m, 3H), 0.99 (t, 3H)

Example 95

Synthesis of N-(1-azabicyclo[2.2.2]octan-3-yl)-6-oxo-1-[2-(phenylthio)phenyl]-3-pyridinecarboxamide

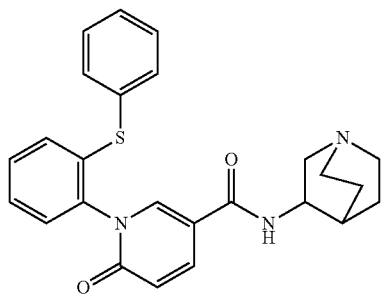

A target compound was obtained in the same manner as in Example 1 and Method 2, except that 2-(phenylthio)aniline was used as a starting material.

$^1$H-NMR (CDCl$_3$, 500 MHz) δ7.92 (m, 1H), 7.83 (d, 1H), 7.30 (m, 9H), 6.75 (br, s, 1H), 6.55 (d, 1H), 4.08 (m, 1H), 3.30 (m, 1H), 2.81 (m, 4H), 2.67 (m, 1H), 1.99 (m, 1H), 1.70 (m, 3H), 1.44 (m, 1H)

Example 96

Synthesis of N-(1-azabicyclo[2.2.2]octan-3-yl)-1-[2-(methylthio)-4-propan-2-ylphenyl]-6-oxo-3-pyridinecarboxamide

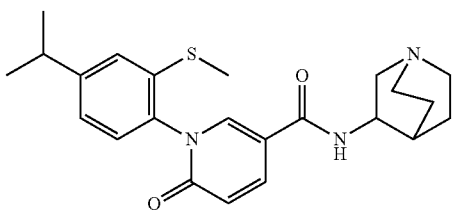 [SMILES: CSc1cc(C(C)C)ccc1-n1cc(C(=O)NC2CN3CCC2CC3)ccc1=O]

A target compound was obtained in the same manner as in Example 1 and Method 1, except that 2-(methylthio)-4-propan-2-yl aniline was used as a starting material.

$^1$H-NMR (CDCl$_3$, 500 MHz) δ8.03 (m, 2H), 7.32 (br, 1H), 7.23 (s, 1H), 7.12 (m, 2H), 6.61 (d, 1H), 4.28 (m, 1H), 3.42 (m, 1H), 3.37 (m, 1H), 3.23 (m, 1H), 2.96 (m, 4H), 2.41 (s, 3H), 2.19 (m, 1H), 2.06 (m, 1H), 1.85 (m, 2H), 1.59 (m, 1H), 1.29 (m, 6H)

Example 97

Synthesis of N-(1-azabicyclo[2.2.2]octan-3-yl)-1-[4-chloro-2-(ethylthio)phenyl]-6-oxo-3-pyridinecarboxamide

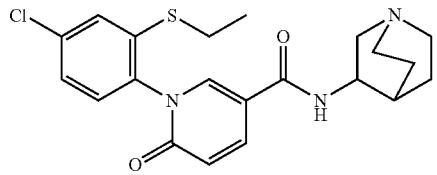 [SMILES: CCSc1cc(Cl)ccc1-n1cc(C(=O)NC2CN3CCC2CC3)ccc1=O]

A target compound was obtained in the same manner as in Example 1 and Method 1, except that 4-chloro-2-(ethylthio)aniline was used as a starting material.

$^1$H-NMR (CDCl$_3$, 500 MHz) δ8.03 (d, 1H), 7.97 (d, 1H), 7.36 (s, 1H), 7.21 (m, 1H), 7.20 (br, 1H), 7.16 (m, 1H), 6.59 (d, 1H), 4.28 (m, 1H), 3.42 (m, 1H), 3.28 (m, 1H), 3.16 (m, 1H), 2.98 (m, 5H), 2.16 (m, 1H), 1.97 (m, 1H), 1.85 (m, 2H), 1.58 (m, 1H), 1.29 (t, 3H)

Example 98

Synthesis of N-(1-azabicyclo[2.2.2]octan-3-yl)-1-[4-ethyl-2-(methylthio)phenyl]-6-oxo-3-pyridinecarboxamide

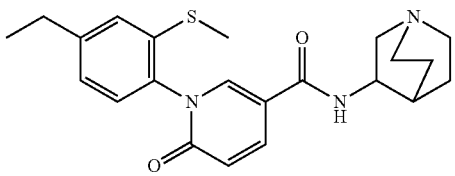 [SMILES: CCc1ccc(-n2cc(C(=O)NC3CN4CCC3CC4)ccc2=O)c(SC)c1]

A target compound was obtained in the same manner as in Example 1 and Method 1, except that 4-ethyl-2-(methylthio)aniline was used as a starting material.

¹H-NMR (CDCl₃, 500 MHz) δ7.91 (s, 1H), 7.73 (m, 1H), 7.30 (m, 1H), 7.18 (m, 2H), 6.64 (d, 1H), 6.10 (br, 1H), 4.12 (m, 1H), 3.42 (m, 1H), 2.89 (m, 4H), 2.73 (m, 3H), 2.40 (s, 3H), 2.03 (m, 1H), 1.70 (m, 3H), 1.47 (m, 1H), 1.23 (t, 3H)

Example 99

Synthesis of N-(1-azabicyclo[2.2.2]octan-3-yl)-1-[4-cyclohexyl-2-(methylthio)phenyl]-6-oxo-3-pyridinecarboxamide

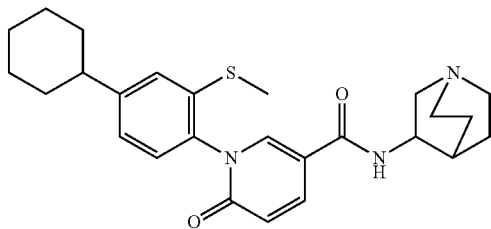 [SMILES: CSc1cc(C2CCCCC2)ccc1-n1cc(C(=O)NC2CN3CCC2CC3)ccc1=O]

A target compound was obtained in the same manner as in Example 1 and Method 1, except that 4-cyclohexyl-2-(methylthio)aniline was used as a starting material.

¹H-NMR (CDCl₃, 500 MHz) δ7.90 (s, 1H), 7.75 (d, 1H), 7.22 (s, 1H), 7.14 (m, 2H), 6.64 (d, 1H), 6.18 (br, 1H), 4.10 (m, 1H), 3.41 (m, 1H), 2.92 (m, 4H), 2.57 (m, 2H), 2.41 (s, 3H), 2.01 (m, 1H), 1.92 (m, 4H), 1.77 (m, 4H), 1.52 (m, 5H), 1.28 (m, 1H)

Example 100

Synthesis of N-(1-azabicyclo[2.2.2]octan-3-yl)-1-(2-methylsulfonylphenyl)-6-oxo-3-pyridinecarboxamide

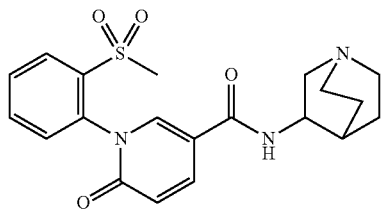 [SMILES: CS(=O)(=O)c1ccccc1-n1cc(C(=O)NC2CN3CCC2CC3)ccc1=O]

A target compound was obtained in the same manner as in Example 1 and Method 2, except that 2-methylsulfonyl aniline was used as a starting material.

¹H-NMR (CDCl₃, 500 MHz) δ8.10 (m, 1H), 7.94 (s, 1H), 7.85 (d, 1H), 7.77 (m, 1H), 7.69 (m, 1H), 7.37 (m, 1H), 6.67 (br, d, 1H), 6.53 (d, 1H), 3.94 (m, 1H), 3.22 (m, 1H), 3.07 (s, 3H), 2.74 (m, 4H), 2.49 (m, 1H), 1.88 (m, 1H), 1.61 (m, 3H), 1.36 (m, 1H)

Example 101

Synthesis of N-(1-azabicyclo[2.2.2]octan-3-yl)-1-(4-methylsulfonylphenyl)-6-oxo-3-pyridinecarboxamide

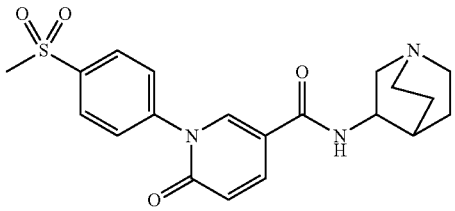 [SMILES: CS(=O)(=O)c1ccc(-n2cc(C(=O)NC3CN4CCC3CC4)ccc2=O)cc1]

A target compound was obtained in the same manner as in Example 1 and Method 2, except that 4-methylsulfonyl aniline was used as a starting material.

¹H-NMR (CDCl₃, 500 MHz) δ8.16 (s, 1H), 8.11 (d, 2H), 7.77 (d, 1H), 7.66 (d, 2H), 6.69 (d, 1H), 6.35 (br, d, 1H), 4.15 (m, 1H), 3.12 (m, 1H), 3.07 (s, 3H), 2.86 (m, 4H), 2.62 (m, 1H), 1.87 (m, 1H), 1.56 (m, 3H), 1.34 (m, 1H)

Example 102

Synthesis of N-(1-azabicyclo[2.2.2]octan-3-yl)-1-(1-naphthalenyl)-6-oxo-3-pyridinecarboxamide

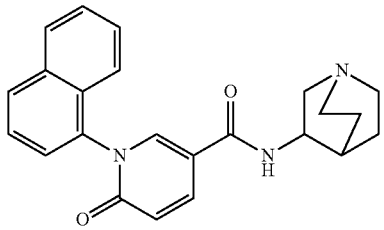 [SMILES: O=C(NC1CN2CCC1CC2)c1ccc(=O)n(-c2cccc3ccccc23)c1]

A target compound was obtained in the same manner as in Example 1 and Method 1, except that 1-aminonaphthalene was used as a starting material.

¹H-NMR (CDCl₃, 500 MHz) δ8.01 (m, 3H), 7.85 (d, 1H), 7.60 (m, 3H), 7.41 (m, 2H), 6.71 (d, 1H), 6.28 (br, 1H), 4.07 (m, 1H), 3.40 (m, 1H), 2.83 (m, 4H), 2.58 (m, 1H), 1.98 (m, 1H), 1.68 (m, 3H), 1.46 (m, 1H)

Example 103

Synthesis of N-(1-azabicyclo[2.2.2]octan-3-yl)-1-(2-naphthalenyl)-6-oxo-3-pyridinecarboxamide

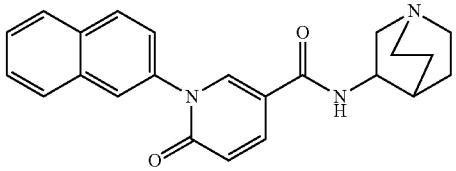 [SMILES: O=C(NC1CN2CCC1CC2)c1ccc(=O)n(-c2ccc3ccccc3c2)c1]

A target compound was obtained in the same manner as in Example 1 and Method 1, except that 2-aminonaphthalene was used as a starting material.

$^1$H-NMR (CDCl$_3$, 500 MHz) δ8.22 (s, 1H), 7.87 (m, 5H), 7.56 (m, 2H), 7.42 (m, 1H), 6.60 (m, 2H), 4.13 (m, 1H), 3.35 (m, 1H), 2.88 (m, 4H), 2.69 (m, 1H) 2.02 (m, 1H), 1.76 (m, 3H), 1.47 (m, 1H)

Example 104

Synthesis of N-(1-azabicyclo[2.2.2]octan-3-yl)-6-oxo-1-[2-(2-thiazolyl)phenyl]-3-pyridinecarboxamide

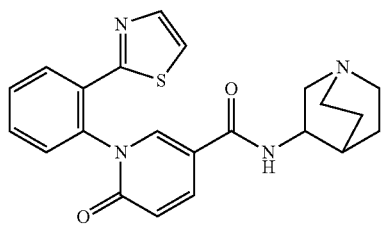 [SMILES: O=C(NC1CN2CCC1CC2)c1ccc(=O)n(-c2ccccc2-c2nccs2)c1]

A target compound was obtained in the same manner as in Example 1 and Method 2, except that 2-(2-thiazolyl)aniline was used as a starting material.

$^1$H-NMR (CDCl$_3$, 500 MHz) δ8.03 (m, 2H), 7.78 (d, 1H), 7.67 (d, 1H), 7.53 (m, 2H), 7.27 (d, 1H), 7.20 (m, 1H), 7.09 (br, d, 1H), 6.34 (d, 1H), 3.92 (m, 1H), 3.17 (m, 1H), 2.69 (m, 4H), 2.47 (m, 1H), 1.80 (m, 1H), 1.56 (m, 3H), 1.25 (m, 1H)

Example 105

Synthesis of N-(1-azabicyclo[2.2.2]octan-3-yl)-1-[4-chloro-2-(2-thiazolyl)phenyl]-6-oxo-3-pyridine carboxamide

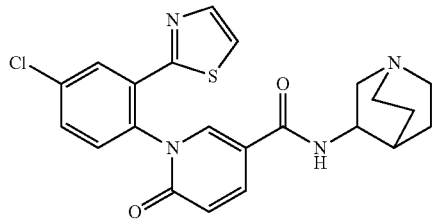 [SMILES: O=C(NC1CN2CCC1CC2)c1ccc(=O)n(-c2ccc(Cl)cc2-c2nccs2)c1]

A target compound was obtained in the same manner as in Example 1 and Method 1, except that 4-chloro-2-(2-thiazolyl)aniline was used as a starting material.

$^1$H-NMR (CDCl$_3$, 500 MHz) δ8.12 (s, 1H), 8.00 (d, 1H), 7.80 (m, 2H), 7.52 (m, 1H), 7.37 (d, 1H), 7.28 (d, 1H), 6.56 (br, 1H), 6.52 (d, 1H), 4.06 (m, 1H), 3.33 (m, 1H), 2.82 (m, 4H), 2.57 (m, 1H), 1.95 (m, 1H), 1.68 (m, 3H), 1.47 (m, 1H)

Example 106

Synthesis of N-(1-azabicyclo[2.2.2]octan-3-yl)-1-[2-(5-methyl-2-thiazolyl)phenyl]-6-oxo-3-pyridinecarboxamide

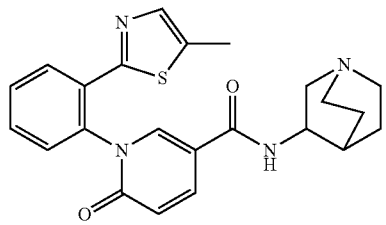 [SMILES: Cc1cnc(-c2ccccc2-n2cc(C(=O)NC3CN4CCC3CC4)ccc2=O)s1]

A target compound was obtained in the same manner as in Example 1 and Method 1, except that 2-(5-methyl-2-thiazolyl)aniline was used as a starting material.

$^1$H-NMR (CDCl$_3$, 500 MHz) δ8.02 (s, 2H), 7.80 (m, 1H), 7.56 (m, 2H), 7.39 (s, 1H), 7.29 (d, 1H), 6.61 (br, 1H), 6.53 (d, 1H), 4.07 (m, 1H), 3.33 (m, 1H), 2.83 (m, 4H), 2.66 (m, 1H), 2.42 (s, 3H), 1.98 (m, 1H), 1.68 (m, 3H), 1.45 (m, 1H)

Example 107

Synthesis of N-(1-azabicyclo[2.2.2]octan-3-yl)-1-[2-(1,3-benzothiazole-2-yl)phenyl]-6-oxo-3-pyridinecarboxamide

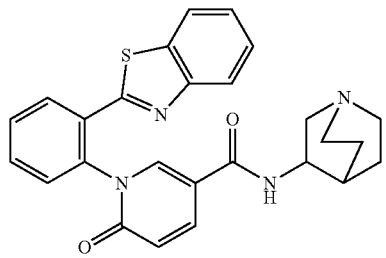 [SMILES: O=C(NC1CN2CCC1CC2)c1ccc(=O)n(-c2ccccc2-c2nc3ccccc3s2)c1]

A target compound was obtained in the same manner as in Example 1 and Method 1, except that 2-(1,3-benzothiazole-2-yl)aniline was used as a starting material.

$^1$H-NMR (CDCl$_3$, 500 MHz) δ8.19 (s, 1H), 8.07 (m, 1H), 7.91 (m, 2H), 7.81 (m, 1H), 7.79 (m, 2H), 7.47 (m, 2H), 7.40 (m, 1H), 6.62 (m, 1H), 6.14 (br, 1H), 4.13 (m, 1H), 3.42 (m, 1H), 2.87 (m, 4H), 2.62 (m, 1H), 2.06 (m, 1H), 1.72 (m, 3H), 1.55 (m, 1H)

Example 108

Synthesis of N-(1-azabicyclo[2.2.2]octan-3-yl)-1-[4-(5-methyl-2-thiophenyl)phenyl]-6-oxo-3-pyridinecarboxamide

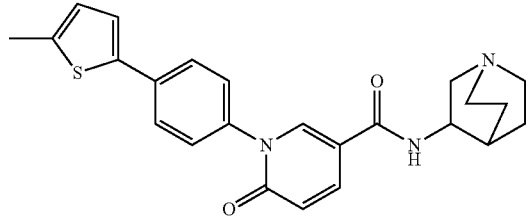 [SMILES: Cc1ccc(-c2ccc(-n3cc(C(=O)NC4CN5CCC4CC5)ccc3=O)cc2)s1]

A target compound was obtained in the same manner as in Example 1 and Method 1, except that 4-(5-methyl-2-thiophenyl)aniline was used as a starting material.

$^1$H-NMR (CDCl$_3$, 500 MHz) δ8.13 (s, 1H), 7.73 (d, 1H), 7.68 (d, 2H), 7.36 (d, 2H), 7.17 (d, 1H), 6.68 (d, 1H), 6.77 (d, 1H), 6.17 (br, 1H), 4.14 (m, 1H), 3.46 (m, 1H), 2.88 (m, 4H), 2.63 (m, 1H), 2.54 (m, 3H), 2.04 (m, 1H), 1.78 (m, 3H), 1.58 (m, 1H)

Example 109

Synthesis of N-(1-azabicyclo[2.2.2]octan-3-yl)-1-[2-chloro-4-(5-methyl-2-thiophenyl)phenyl]-6-oxo-3-pyridinecarboxamide

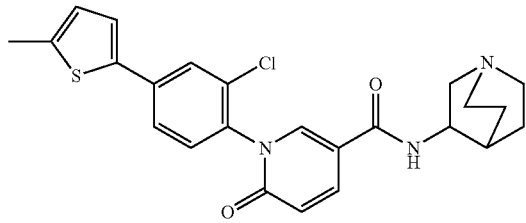 [SMILES: Cc1ccc(-c2ccc(-n3cc(C(=O)NC4CN5CCC4CC5)ccc3=O)c(Cl)c2)s1]

A target compound was obtained in the same manner as in Example 1 and Method 1, except that 2-chloro-4-(5-methyl-2-thiophenyl)aniline was used as a starting material.

$^1$H-NMR (CDCl$_3$, 500 MHz) δ8.07 (s, 1H), 7.91 (m, 1H), 7.87 (s, 1H), 7.56 (m, 1H), 7.35 (m, 1H), 7.18 (m, 1H), 6.84 (m, 2H), 6.65 (d, 1H), 4.23 (m, 1H), 3.46 (m, 1H), 3.21 (m, 1H), 2.93 (m, 4H), 2.58 (m, 3H), 2.08 (m, 1H), 1.75 (m, 3H), 1.58 (m, 1H)

Example 110

Synthesis of N-(1-azabicyclo[2.2.2]octan-3-yl)-6-oxo-1-(2-thiophene-2-ylphenyl)-3-pyridinecarboxamide

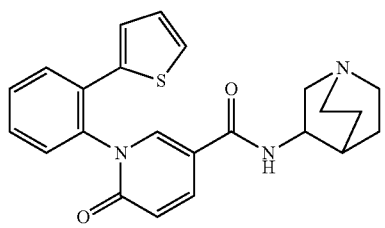 [SMILES: O=C(NC1CN2CCC1CC2)c1ccc(=O)n(-c2ccccc2-c2cccs2)c1]

A target compound was obtained in the same manner as in Example 1 and Method 1, except that 2-(thiophene-2-yl)aniline was used as a starting material.

$^1$H-NMR (CDCl$_3$, 500 MHz) δ7.93 (s, 1H), 7.92 (m, 1H), 7.71 (m, 1H), 7.54 (m, 2H), 7.46 (m, 1H), 6.99 (m, 2H), 6.62 (m, 1H), 6.60 (m, 1H), 6.52 (br, 1H), 4.21 (m, 1H), 3.40 (m, 1H), 3.20 (m, 1H), 2.93 (m, 4H), 2.12 (m, 1H), 1.92 (m, 3H), 1.62 (m, 1H)

Example 111

Synthesis of N-(1-azabicyclo[2.2.2]octan-3-yl)-1-[2-(5-methyl-2-thiophenyl)phenyl]-6-oxo-3-pyridinecarboxamide

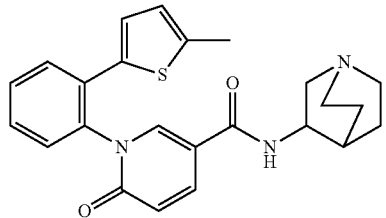 [SMILES: Cc1ccc(-c2ccccc2-n2cc(C(=O)NC3CN4CCC3CC4)ccc2=O)s1]

A target compound was obtained in the same manner as in Example 1 and Method 1, except that 2-(5-methyl-2-thiophenyl)aniline was used as a starting material.

$^1$H-NMR (CDCl$_3$, 500 MHz) δ8.54 (m, 1H), 8.49 (m, 1H), 8.23 (m, 1H), 7.63 (m, 1H), 7.47 (m, 1H), 7.44 (m, 1H), 7.35 (m, 2H), 6.76 (m, 1H), 6.60 (m, 1H), 4.54 (m, 1H), 4.22 (m, 1H), 4.04 (m, 1H), 3.36 (m, 1H), 3.16 (m, 3H), 2.45 (m, 1H), 2.41 (s, 3H), 2.05 (m, 3H), 1.76 (m, 1H)

Example 112

Synthesis of N-(1-azabicyclo[2.2.2]octan-3-yl)-1-[3-(2-methyl-4-thiazolyl)phenyl]-6-oxo-3-pyridinecarboxamide

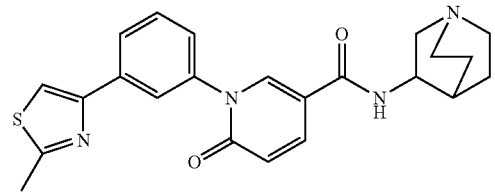 [SMILES: Cc1nc(-c2cccc(-n3cc(C(=O)NC4CN5CCC4CC5)ccc3=O)c2)cs1]

A target compound was obtained in the same manner as in Example 1 and Method 2, except that 3-(2-methyl-4-thiazolyl)aniline was used as a starting material.

$^1$H-NMR (CDCl$_3$, 500 MHz) δ8.14 (s, 1H), 7.95 (m, 2H), 7.72 (m, 1H), 7.58 (m, 1H), 7.44 (s, 1H), 7.35 (m, 1H), 6.68 (d, 1H), 6.15 (br, 1H), 4.13 (m, 1H), 3.45 (m, 1H), 2.92 (m, 4H), 2.78 (s, 3H), 2.57 (m, 1H), 2.03 (m, 1H), 1.72 (m, 3H), 1.54 (m, 1H)

Example 113

Synthesis of N-(1-azabicyclo[2.2.2]octan-3-yl)-1-[4-dimethylaminophenyl]-6-oxo-3-pyridinecarboxamide

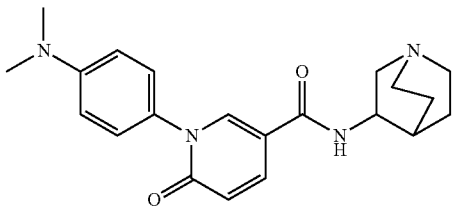 [SMILES: CN(C)c1ccc(-n2cc(C(=O)NC3CN4CCC3CC4)ccc2=O)cc1]

Example 113-1

Synthesis of methyl 1-(4-dimethylaminophenyl)-1,6-dihydro-6-oxo-3-pyridinecarboxylate After 1.24 g (6.1 mmol) of dimethyl 4-(methoxymethylene)$_2$-pentenedioate obtained in Example 1-1 was dissolved in 10 mL of DMF, 830 g (6.1 mmol) of 4-dimethylaminoaniline was added to the solution. Afterward, the resulting reaction solution was stirred under reflux at about 50° C. for about 3 hours. After termination of the reaction was determined by liquid chromatography, the solvent was removed in vacuo and was then washed using brine, followed by drying using magnesium sulfate and filtration. After distillation under reduced pressure, the resulting product was purified using column chromatography (hexane:ethyl acetate=1:1) to obtain a target compound (Actual yield: 357 mg, Yield ratio: 21%).

Example 113-2

Synthesis of 1-(4-dimethylaminophenyl)-1,6-dihydro-6-oxo-3-pyridinecarboxylic acid After 357 mg (1.31 mmol) of methyl 1-(4-dimethylaminophenyl)-1,6-dihydro-6-oxo-3-pyridinecarboxylate was dissolved in 12 mL of methanol and 4 mL of water, 94 mg (3.93 mmol) of lithium hydroxide was added to the solution. Afterward, the resulting reaction solution was stirred at about 50° C. for about 5 hours. After termination of the reaction was determined by liquid chromatography, the solvent was removed in vacuo, and aqueous HCl was then added to the reaction solution to titrate until a neutral solution was obtained. The resulting solid compound was filtrated and used in Example 113-3 without an additional purification process.

Example 113-3

Synthesis of N-(1-azabicyclo[2.2.2]octan-3-yl)-1-[4-dimethylaminophenyl]-6-oxo-3-pyridinecarboxamide After 300 mg (1.18 mmol) of 1-(4-dimethylaminophenyl)-1,6-dihydro-6-oxo-3-pyridinecarboxylic acid was dissolved in 20 mL of tetrahydrofuran and 2 mL of DMF, 391 mg (1.96 mmol) of 3-aminoquinuclidine dihydrochloride and 460 mg (3.54 mmol) of diethyliso-propylamide were added to the solution. After the reaction solution was stirred at room temperature for about 30 minutes, 600 g (1.57 mmol) of 0-(benzotriazole-1-yl)-N,N,N',N'-tetramethyluroniumhexafluorophosphate (HATU) was added to the reaction solution. This reaction solution was stirred at room temperature for about 20 hours. After termination of the reaction was determined by liquid chromatography, the solvent was removed in vacuo, followed by extraction three times with chloroform and an aqueous NaOH solution (pH 12) and purification using liquid chromatography (chloroform:methanol:ammonia water=10:1:0.1) to obtain a target compound (Actual yield: 158 mg, Percent yield: 31%).

$^1$H-NMR (CDCl$_3$, 500 MHz) δ8.11 (s, 1H), 7.78 (d, 1H), 7.13 (d, 2H), 6.84 (br, 1H), 6.68 (d, 2H), 6.53 (d, 1H), 4.10 (m, 1H), 3.35 (m, 1H), 2.98 (s, 6H), 3.16 (m, 1H), 2.82 (m, 4H), 2.68 (m, 1H), 1.99 (m, 1H), 1.72 (m, 3H), 1.46 (m, 1H)

Example 114

Synthesis of N-(1-azabicyclo[2.2.2]octan-3-yl)-1-{4-[(methyl-propl-2-ylnyl-amino)-methyl]-phenyl}-6-oxo-3-pyridinecarboxamide

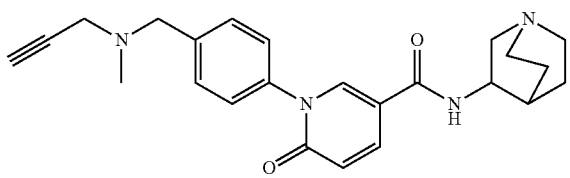 [SMILES: C#CCN(C)Cc1ccc(-n2cc(C(=O)NC3CN4CCC3CC4)ccc2=O)cc1]

A target compound was obtained in the same manner as in Example 1 and Method 113, except that 1-{4-[(methyl-prop-2-ylnyl-amino)-methyl]-phenyl}aniline was used as a starting material.

$^1$H-NMR (CDCl$_3$, 500 MHz) δ8.11 (s, 1H), 7.79 (d, 1H), 7.45 (d, 2H), 7.27 (d, 2H), 6.75 (br, d, 1H), 6.56 (d, 1H), 4.08 (m, 1H), 3.61 (s, 2H), 3.34 (m, 3H), 2.84 (m, 4H), 2.62 (m, 1H), 2.35 (s, 3H), 2.29 (s, 1H), 2.21 (s, 1H), 1.97 (m, 1H), 1.60 (m, 3H), 1.45 (m, 1H)

Example 115

Synthesis of (1-azabicyclo[2.2.2]octan-3-yl)-6-oxo-1-phenyl-3-pyridinecarboxylate

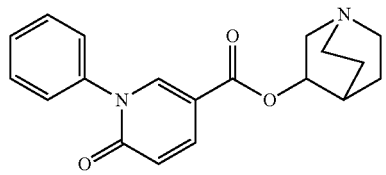 [SMILES: O=C(OC1CN2CCC1CC2)c1ccc(=O)n(-c2ccccc2)c1]

Example 115-1

Synthesis of 6-oxo-1-phenyl-1,6-dihydro-pyridine-3-carbonyl chloride

After 197 mg (0.91 mmol) of 6-oxo-1-phenyl-1,6-dihydro-pyridine-3-carboxylic acid obtained in Example 1-3 was dissolved in 10 mL of toluene, 217 mg (1.82 mmol) of thionyl chloridethionyl chloride was added to the solution. Afterward, the resulting reaction solution was stirred under reflux at about 100° C. for 2 hours. After termination of the reaction was determined by liquid chromatography, the solvent was removed in vacuo and was then used in Example 115-2 without an additional purification process.

Example 115-2

Synthesis of (1-azabicyclo[2.2.2]octan-3-yl)-6-oxo-1-phenyl-3-pyridinecarboxylate After dissolution of the mixed solution of 6-oxo-1-phenyl-1,6-dihydro-pyridine-3-carbonyl chloride obtained in Example 115-1 in 5 mL of pyridine, 231 mg (1.82 mmol) of 3-hydroxyquinuclidine was added thereto. Afterward, the resulting reaction solution was stirred at room temperature for about 3 days. After termination of the reaction was determined by liquid chromatography, the solvent was removed in vacuo. Without an additional purification process, the resulting compound was extracted three times with water and chloroform, and the organic phase was purified using liquid chromatography (chloroform:methanol: ammonia water=10:1: 0.1) to obtain a target compound (Actual yield: 65 mg, Percent yield: 20%).

$^1$H-NMR (CDCl$_3$, 500 MHz) δ8.23 (s, 1H), 7.94 (d, 1H), 7.50 (m3H), 7.40 (d, 2H), 6.66 (d, 1H), 5.01 (m, 1H), 3.33 (m, 1H), 2.83 (m, 5H), 2.12 (m, 1H), 1.87 (m, 1H), 1.74 (m, 1H), 1.63 (m, 1H), 1.48 (m, 1H)

Example 116

Synthesis of (1-azabicyclo[2.2.2]octan-3-yl)-1-(2,4-dichlorophenyl)-6-oxo-3-pyridinecarboxylate

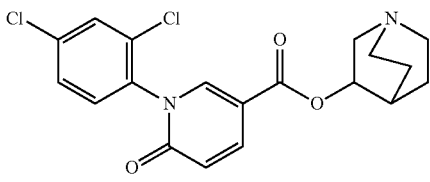 [SMILES: O=C(OC1CN2CCC1CC2)c1ccc(=O)n(-c2ccc(Cl)cc2Cl)c1]

A target compound was obtained in the same manner as in Example 115, except that 2,4-dichloroaniline was used as a starting material.

$^1$H-NMR (CDCl$_3$, 500 MHz) δ8.01 (s, 1H), 7.95 (d, 1H), 7.59 (s, 1H), 7.40 (m, 1H), 7.32 (m, 1H), 6.64 (d, 1H), 4.99 (m, 1H), 3.29 (m, 1H), 2.78 (m, 5H), 2.09 (m, 1H), 1.85 (m, 1H), 1.71 (m, 1H), 1.60 (m, 1H), 1.45 (m, 1H)

Example 117

Synthesis of N-(1-azabicyclo[2.2.2]octan-3-yl)-2-oxo-1-phenyl-3-pyridinecarboxamide

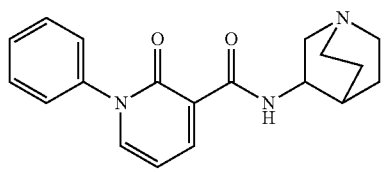 [SMILES: O=C(NC1CN2CCC1CC2)c1cccn(-c2ccccc2)c1=O]

Example 117

Synthesis of 2-hydroxynicotinic acid 1.5 g (10.6 mmol) of 2-fluoronicotinic acid was dissolved in 42 mL of 6N HCl and was then stirred under reflux for about 1 hour. Afterward, the resulting reaction product was cooled to room temperature and was then filtrated to obtain a solid compound. The resulting solid compound was used in Example 117-2 without an additional purification process.

Example 117-2

Synthesis of methyl 2-hydroxy nicotinate

After 1 g (7.19 mmol) of 2-hydroxynicotinic acid was dissolved in 20 mL of methylene chloride, 3.4 g (28.8 mmol) of thionyl chloride was added thereto. Afterward, the resulting reaction solution was stirred at about 75° C. for 3 hours. After termination of the reaction was determined by liquid chromatography, the solvent was removed in vacuo. This compound was dissolved in methanol and was then stirred at room temperature for about 2 hours. The compound was extracted three times with water and dichloromethane, and an organic solvent phase was purified using column chromatography (hexane:ethyl acetate=1:1) to obtain a target compound (Actual yield: 480 mg, Percent yield: 53%).

Example 117-3

Synthesis of methyl 2-oxo-1-phenyl-1,2-dihydropyridine-3-carboxylate

After 480 mg (3.8 mmol) of methyl 2-hydroxy nicotinate, 0.56 mL (7.6 mmol) of pyridine, and 634 mg (4.1 mmol) of acetate were mixed together, 10 mL of methylene chloride was added thereto. 775 mg (7.6 mmol) of phenylboronic acid was added to the mixed solution and was then stirred at room temperature for about 12 hours. After termination of the reaction was determined by liquid chromatography, the solvent was removed in vacuo. The resulting mixed solution was extracted three times with an aqueous ammonium chloride solution and dichloromethane, and an organic solvent phase was purified using column chromatography (hexane:ethyl acetate=1:2) to obtain a target compound (Actual yield: 430 mg, Percent yield: 49%).

Example 117-4

Synthesis of 2-oxo-1-phenyl-1,2-dihydropyridine-3-carboxylic acid

A target compound was obtained using methyl 2-oxo-1-phenyl-1,2-dihydropyridine-3-carboxylate in the same manner as in Example 1-3.

Example 117-5

Synthesis of N-(1-azabicyclo[2.2.2]octan-3-yl)-2-oxo-1-phenyl-3-pyridinecarboxamide A target compound was obtained using 2-oxo-1-phenyl-1,2-dihydropyridine-3-carboxylic acid in the same manner as in Example 1-4 and Method 2.

$^1$H-NMR (CDCl$_3$, 200 MHz) δ10.01 (br, 1H), 8.51 (d, 1H), 7.47 (m, 6H), 6.50 (t, 1H), 4.07 (m, 1H), 3.29 (m, 1H), 2.78 (m, 4H), 2.59 (m, 1H), 1.94 (m, 1H), 1.65 (m, 3H), 1.41 (m, 1H)

Example 118

Synthesis of N-(1-azabicyclo[2.2.2]octan-3-yl)-1-(4-methoxyphenyl)-2-oxo-3-pyridinecarboxamide

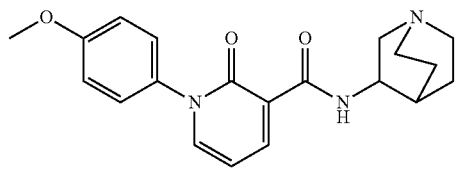 [SMILES: COc1ccc(-n2cccc(C(=O)NC3CN4CCC3CC4)c2=O)cc1]

A target compound was obtained in the same manner as in Example 117, except that 4-methoxyphenylboronic acid was used as a starting material.

¹H-NMR (CDCl₃, 500 MHz) δ10.00 (br, 1H), 8.57 (d, 1H), 7.53 (d, 1H), 7.26 (d, 2H), 7.00 (d, 2H), 6.47 (t, 1H), 4.08 (m, 1H), 3.82 (s, 3H), 3.32 (m, 1H), 2.78 (m, 4H), 2.57 (m, 1H), 1.93 (m, 1H), 1.64 (m, 3H), 1.40 (m, 1H)

Example 119

Synthesis of N-(1-azabicyclo[2.2.2]octan-3-yl)-1-(4-chlorophenyl)-2-oxo-3-pyridinecarboxamide

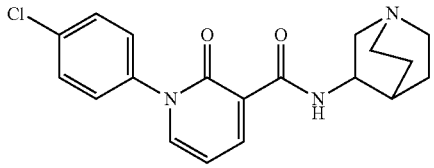 [SMILES: O=C(NC1CN2CCC1CC2)c1cccn(-c2ccc(Cl)cc2)c1=O]

A target compound was obtained in the same manner as in Example 117, except that 4-chlorophenylboronic acid was used as a starting material.

¹H-NMR (CDCl₃, 200 MHz) δ9.80 (br, 1H), 8.46 (d, 1H), 7.43 (m, 3H), 7.24 (d, 2H), 6.41 (t, 1H), 3.94 (m, 1H), 3.20 (m, 1H), 2.67 (m, 4H), 2.49 (m, 1H), 1.81 (m, 1H), 1.52 (m, 3H), 1.27 (m, 1H)

Example 120

Synthesis of N-(1-azabicyclo[2.2.2]octan-3-yl)-2-oxo-1-[4-(trifluoromethyl)phenyl]-3-pyridinecarboxamide

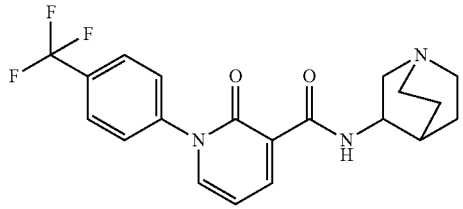 [SMILES: O=C(NC1CN2CCC1CC2)c1cccn(-c2ccc(C(F)(F)F)cc2)c1=O]

A target compound was obtained in the same manner as in Example 117, except that 4-trifluoromethylphenylboronic acid was used as a starting material.

¹H-NMR (CDCl₃, 200 MHz) δ9.90 (br, 1H), 8.64 (d, 1H), 7.83 (d, 2H), 7.54 (m, 3H), 6.56 (t, 1H), 4.11 (m, 1H), 3.34 (m, 1H), 2.78 (m, 4H), 2.59 (m, 1H), 1.94 (m, 1H), 1.66 (m, 3H), 1.42 (m, 1H)

Example 121

Synthesis of N-(1-azabicyclo[2.2.2]octan-3-yl)-1-(4-tert-butylphenyl)-2-oxo-3-pyridinecarboxamide

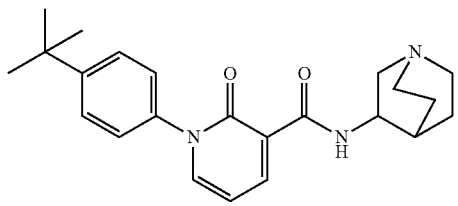 [SMILES: CC(C)(C)c1ccc(-n2cccc(C(=O)NC3CN4CCC3CC4)c2=O)cc1]

A target compound was obtained in the same manner as in Example 117, except that 4-tert-butylphenylboronic acid was used as a starting material.

¹H-NMR (CDCl₃, 200 MHz) δ10.01 (br, 1H), 8.63 (d, 1H), 7.55 (m, 3H), 7.30 (d, 2H), 6.51 (t, 1H), 4.18 (m, 1H), 3.38 (m, 1H), 2.82 (m, 4H), 2.61 (m, 1H), 1.99 (m, 1H), 1.68 (m, 3H), 1.43 (m, 1H)

Example 122

Measurement of Human α7 Nicotinic Acetylcholine Receptor (nAChR)'s Activity

Activity of heteromeric α7 nAChR was measured via Flex-Station-Ca²⁺ influx assay. In the present example, in consideration of α7 nAChR being Ca2+-permeable non-selective cationic channels, changes intracellular Ca²⁺ concentration were measured using a fluorescent dye Calcium-3 (available from Molecular Devices) and FlexStation II instrument (available from Molecular Devices).

Human CHRNA7 (NM_000746) cDNA ORF clone (C/N RC221382; Origene) and Human RIC (NM_024557) cDNA ORF clone (C/N RC205179; Origene) were subcloned into pcDNA2.1/Zeo(+) vector (available from Invitrogen, Co.) to construct HEK293T/17 cells (ATCC, CRL-11268) transfected with human α7 nAChR. Afterward, the cells were suspended in growth media (consisted of Dulbecco's Modified Eagle's Media (DMEM, available from Invitrogen), a 10% heat-inactivated fetal bovine serum (FBS, available from Invitrogen), 300 µg/ml Geneticin (available from Invitrogen), 250 µg/ml Zeocin (available from Invitrogen), and 1× penicillin/streptomycin (available from Invitrogen)), followed by plating onto a Φ150 mm plate. Twenty-four hours prior to the start of the assay, grown cells in the suspension were collected, followed by centrifugation and further suspension at a concentration of 5×10⁵ cells/mL in growth media. This cell suspension was dispensed to each well of a 96-well black plate (5×10⁴ cells/well) with a poly-D-lysine-coated transparent bottom (available from Biocoat, BD). The plate with the cells were incubated at about 37° C. in 5% CO₂ for about 24 hours.

On the day of the assay, after removal of the growth media, the cells were washed once with an assay buffer (7 mM Tris-Cl, 20 mM HEPES, 20 mM NaCl, 5 mM KCl, 0.8 mM MgSO₄, 4 mM CaCl₂, 120 mM NMDG, 5 mM D-glucose, pH 7.4), followed by addition of about 100 ul per well of a Calcium-3 dye diluted with the assay buffer, and storage at room temperature for about 1 hour. A test compound (10 mM stock in 100% dimethyl sulfoxide (DMSO)) was diluted with the assay buffer to various concentrations, from the highest at about 40 µM to be lower by ⅓, and PNU-120596 (available from Sigma) for amplifying Ca²⁺ permeability signaling was diluted to about 30 µM with the assay buffer. Epibatidine (available from Sigma) in a final concentration of about 1 µM was used as a positive control group.

To measure changes in intracellular Ca²⁺ concentration, after the plate was stored at room temperature for about 1 hour and the test compound dilution plate were put into FlexStation II equipment, fluorescence of the cells were measured for about 30 seconds prior to addition of drugs (the compounds), followed by addition of PNU-120596 and measurement of changes in fluorescence for about 120 seconds. After the cells were exposed to the test compound, changes in fluorescence for about 90 seconds were measured (excitation at 485 nm/emission at 525 nm). The largest fluorescence value at each concentration was recorded, and an EC₅₀ of the test compound was determined using non-linear regression analysis with relative fluorescence values relative to the positive control group.

The results were represented as $EC_{50}$ values. For those compounds lacking dependency on concentration, relative fluorescence values were read at a concentration with the highest fluorescence value among the compounds tested. This test was performed one time or more. Efficacies of the compounds synthesized in some examples were tested using the same method as above, and the results are shown in Tables 1 and 2 below. In Table 1, + denotes an $EC_{50}$ of 1000 nM or greater, ++ denotes an $EC_{50}$ of from 500 nM to 1000 nM, +++ denotes an $EC_{50}$ of from 100 nM to about 500 nM, and ++++ denotes an $EC_{50}$ of 100 nM or less.

TABLE 1

| Example | $EC_{50}$ of human α7nAChR(nM) |
|---|---|
| 1 | + |
| 2 | ++++ |
| 4 | + |
| 5 | + |
| 6 | + |
| 7 | ++ |
| 11 | + |
| 12 | ++ |
| 14 | ++ |
| 15 | ++ |
| 17 | ++ |
| 18 | ++ |
| 20 | ++ |
| 25 | ++ |
| 26 | +++ |
| 27 | + |
| 29 | + |
| 32 | + |
| 33 | +++ |
| 36 | +++ |
| 38 | +++ |
| 46 | +++ |
| 49 | +++ |
| 56 | ++ |
| 57 | +++ |
| 60 | ++ |
| 63 | + |
| 65 | +++ |
| 67 | ++ |
| 69 | +++ |
| 70 | +++ |
| 71 | +++ |
| 72 | +++ |
| 73 | ++ |
| 74 | +++ |
| 76 | +++ |
| 77 | ++++ |
| 78 | ++++ |
| 79 | +++ |
| 80 | ++++ |
| 81 | +++ |
| 82 | +++ |
| 83 | ++ |
| 84 | ++++ |
| 85 | ++++ |
| 86 | ++++ |
| 87 | ++++ |
| 88 | +++ |
| 89 | ++++ |
| 90 | ++++ |
| 91 | +++ |
| 93 | +++ |
| 94 | ++++ |
| 95 | ++++ |
| 96 | ++++ |
| 97 | ++++ |
| 98 | ++++ |
| 99 | +++ |
| 101 | +++ |

TABLE 1-continued

| Example | $EC_{50}$ of human α7nAChR(nM) |
|---|---|
| 102 | +++ |
| 104 | +++ |
| 105 | ++ |
| 106 | ++ |
| 107 | ++++ |
| 108 | +++ |
| 109 | +++ |
| 110 | +++ |
| 111 | +++ |
| 113 | ++ |
| 115 | + |

+; 1000 nM or greater,
++; from 500 nm to 1000 nM,
+++; from 100 mM to 500 nM,
++++; 100 nM or less Example 123

Novel Object Recognition Test (NORT) on Mice Administered with Pyridone Derivative Compound-Containing Composition A NORT, which was first introduced by Ennaceur and Delacour, is a cognitive memory test for measuring whether rats are able to remember objects with which they have had previous experience based on the nature of rats, i.e., preference to explore novel objects [Ennaceur A and Delacour J (1988) A new one-trial test for neurobiological studies of memory in rats. 1; Behavioral data. Behavioral Brain Res. 31; 47-59]. This NOR test is a popular experimental method for measuring changes in memory of objects in rodents administered with either an amnesia-inducing drug or other general drugs, by which memory recovery efficacy of a test drug in the rodents administered with the amnesia-inducing drug is explored. In the present example, the test was performed in accord with the description of Bevins and Besheer [Bevins, R. A. & Besheer, J. Object recognition in rats and mice; a one-trial non-matching-to-sample learning task to study 'recognition memory'. Nat. Protoc. 2006; 1(3); 1306-11. (2006)]. Male ICR mice (available from Orient Bio Inc., Korea) weighing from about 20 g to about 32 g were orally administered a test compound dissolved in a 30% PEG at doses of 0.03~3 mg/kg and 10 ml/kg body weight. 30 minutes after the administration, MK-801 (available from Sigma) dissolved in saline was subcutaneously administered at doses of 0.1 mg/kg and 10 ml/kg body weight to induce amnesia. About 30 minutes after the administration of MK-801, the mice were allowed to explore a rectangular stainless steel pillar or a circular plastic pillar which was previously placed in a box for about 5 minutes. About 24 hours after the exploration, one of the two objects previously presented was replaced with a new one (i.e., to include one rectangular stainless steel pillar and one circular plastic pillar), the times they took to explore were measured for about 5 minutes. A recognition index (RI) was defined as:

[(Exploration time for novel object in test compound group/Exploration time for all objects in test compound group)/(Exploration time for novel object in MK801 group/Exploration time for all objects in MK801 group)×100].

Table 2 below presents relative RIs of the compounds at a minimal dose resulting in half maximal activation ($EC_{50}$).

TABLE 2

| Example | NORT Relative RI (%)@MED |
|---|---|
| 4 | 116.2% @3po |
| 5 | 115.8% @0.1ip |
| 25 | 115.6% @3po |
| 26 | 116.4% @1po |
| 27 | 114.1% @1po |
| 33 | 112.1% @1po |
| 65 | 110.7% @1ip |
| 77 | 122.1% @0.1ip |
| 84 | 119.7% @0.3po |
| 86 | 115.2% @0.3po |
| 89 | 113.8% @0.03po |
| 91 | 118.2% @3po |
| 104 | 114.8% @3po |
| 105 | 116.2% @0.3po |
| 109 | 112.6% @3po |

The invention claimed is:

1. A compound of Formula I or II:

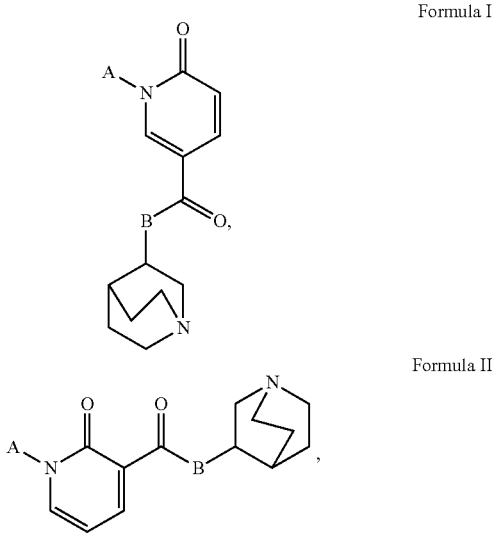

or a pharmaceutically acceptable salt, solvate or hydrate thereof, wherein

A is $C_6$-$C_{12}$ aryl optionally substituted by at least one selected from the group consisting of halo, amino, phenyl, halophenyl, $C_1$-$C_6$ alkylphenyl, $C_1$-$C_6$ alkoxyphenyl, halophenoxy, methylphenoxy, $C_1$-$C_6$ alkyl, halo-$C_1$-$C_6$ alkyl, $C_2$-$C_6$ alkynyl, $C_3$-$C_7$ cycloalkyl, $C_1$-$C_6$ alkoxy, halo-$C_1$-$C_6$ alkoxy, $C_6$-$C_{12}$ aralkoxy, $C_6$-$C_{12}$ aryloxy, $C_1$-$C_6$ alkylthio, $C_6$-$C_{12}$ aralkylthio, $C_6$-$C_{12}$ arylthio, $C_1$-$C_6$ alkylsulfonyl and $C_2$-$C_{10}$ heteroaryl optionally substituted by $C_1$-$C_6$ alkyl; and B is O or NH.

2. The compound of claim 1 or a pharmaceutically acceptable salt, solvate or hydrate thereof, wherein B is NH.

3. The compound of claim 1 or a pharmaceutically acceptable salt, solvate or hydrate thereof, wherein A is phenyl or naphthyl optionally substituted by at least one selected from the group consisting of halo, amino, phenyl, $C_1$-$C_6$ alkyl, $C_2$-$C_6$ alkynyl, $C_3$-$C_7$ cycloalkyl, $C_1$-$C_6$ alkoxy, $C_6$-$C_{12}$ aralkoxy, $C_6$-$C_{12}$ aryloxy, $C_1$-$C_6$ alkylthio, $C_6$-$C_{12}$ aralkylthio, $C_6$-$C_{12}$ arylthio, $C_1$-$C_6$ alkylsulfonyl and $C_2$-$C_{10}$ heteroaryl.

4. The compound of claim 1 or a pharmaceutically acceptable salt, solvate or hydrate thereof, wherein A is phenyl optionally substituted by at least one selected from the group consisting of halo, amino, phenyl, $C_1$-$C_6$ alkyl, $C_2$-$C_6$ alkynyl, $C_3$-$C_7$ cycloalkyl, $C_1$-$C_6$ alkoxy, $C_6$-$C_{12}$ aralkoxy, $C_6$-$C_{12}$ aryloxy, $C_1$-$C_6$ alkylthio, $C_6$-$C_{12}$ aralkylthio, $C_6$-$C_{12}$ arylthio, $C_1$-$C_6$ alkylsulfonyl and $C_2$-$C_{10}$ heteroaryl.

5. The compound of claim 1 or a pharmaceutically acceptable salt, solvate or hydrate thereof, wherein the compound is a compound of Formula I and A is phenyl optionally substituted by at least one selected from the group consisting of halo, amino, phenyl, $C_1$-$C_6$ alkyl, $C_2$-$C_6$ alkynyl, $C_3$-$C_7$ cycloalkyl, $C_1$-$C_6$ alkoxy, $C_6$-$C_{12}$ aralkoxy, $C_6$-$C_{12}$ aryloxy, $C_1$-$C_6$ alkylthio, $C_6$-$C_{12}$ aralkylthio, $C_6$-$C_{12}$ arylthio, $C_1$-$C_6$ alkylsulfonyl and $C_2$-$C_{10}$ heteroaryl.

6. The compound of claim 1 or a pharmaceutically acceptable salt, solvate or hydrate thereof, wherein A is $C_6$-$C_{12}$ aryl optionally substituted by at least one selected from the group consisting of chloro, fluoro, bromo, methyl, ethyl, propyl, iso-propyl, tert-butyl, methoxy, methylthio, ethylthio and thiazolyl.

7. The compound of claim 1 or a pharmaceutically acceptable salt, solvate or hydrate thereof, wherein the compound is selected from the group consisting of:

N-(1-azoniabicyclo[2.2.2]octan-3-yl)-6-oxo-1-phenyl-3-pyridinecarboxamide,

N-(1-azabicyclo[2.2.2]octan-3-yl)-1-(2-chlorophenyl)-6-oxo-3-pyridinecarboxamide, N-(1-azabicyclo[2.2.2]octan-3-yl)-1-(3-chlorophenyl)-6-oxo-3-pyridinecarboxamide, N-(1-azabicyclo[2.2.2]octan-3-yl)-1-(4-chlorophenyl)-6-oxo-3-pyridinecarboxamide, N-[(3R)-1-azabicyclo[2.2.2]octan-3-yl]-1-(4-chlorophenyl)-6-oxopyridine-3-carboxamide, N-([3S)-1-azabicyclo[2.2.2]octan-3-yl]-1-(4-chlorophenyl)-6-oxopyridine-3-carboxamide, N-(1-azabicyclo[2.2.2]octan-3-yl)-1-(4-fluorophenyl)-6-oxo-3-pyridinecarboxamide, N-(1-azabicyclo[2.2.2]octan-3-yl)-1-(2-fluorophenyl)-6-oxo-3-pyridinecarboxamide, N-(1-azabicyclo[2.2.2]octan-3-yl)-1-(3-fluorophenyl)-6-oxo-3-pyridinecarboxamide, N-(1-azabicyclo[2.2.2]octan-3-yl)-1-(4-bromophenyl)-6-oxo-3-pyridinecarboxamide, N-(1-azabicyclo[2.2.2]octan-3-yl)-1-(2-methylphenyl)-6-oxo-3-pyridinecarboxamide, N-(1-azabicyclo[2.2.2]octan-3-yl)-1-(4-methylphenyl)-6-oxo-3-pyridinecarboxamide, N-(1-azabicyclo[2.2.2]octan-3-yl)-1-(3-methylphenyl)-6-oxo-3-pyridinecarboxamide, N-(1-azabicyclo[2.2.2]octan-3-yl)-1-(4-ethylphenyl)-6-oxo-3-pyridinecarboxamide, N-(1-azabicyclo[2.2.2]octan-3-yl)-6-oxo-1-(4-propylphenyl)-3-pyridinecarboxamide, N-(1-azabicyclo[2.2.2]octan-3-yl)-6-oxo-1-(2-propan-2-ylphenyl)-3-pyridinecarboxamide, N-(1-azabicyclo[2.2.2]octan-3-yl)-6-oxo-1-(4-propan-2-ylphenyl)-3-pyridinecarboxamide, N-(1-azabicyclo[2.2.2]octan-3-yl)-1-(4-cyclohexylphenyl)-6-oxo-3-pyridinecarboxamide, N-(1-azabicyclo[2.2.2]octan-3-yl)-1-(4-methoxyphenyl)-6-oxo-3-pyridinecarboxamide, N-(1-azabicyclo[2.2.2]octan-3-yl)-1-(2-methoxyphenyl)-6-oxo-3-pyridinecarboxamide, N-(1-azabicyclo[2.2.2]octan-3-yl)-1-(3-methoxyphenyl)-6-oxo-3-pyridinecarboxamide, N-(1-azabicyclo[2.2.2]octan-3-yl)-6-oxo-1-[4-(trifluoromethyl)phenyl]-3-pyridinecarboxamide,
N-(1-azabicyclo[2.2.2]octan-3-yl)-6-oxo-1-[4-(trifluoromethoxy)phenyl]-3-pyridinecarboxamide,
N-(1-azabicyclo[2.2.2]octan-3-yl)-6-oxo-1-[2-(trifluoromethoxy)phenyl]-3-pyridinecarboxamide,
N-(1-azabicyclo[2.2.2]octan-3-yl)-1-(2,4-dichlorophenyl)-6-oxo-3-pyridinecarboxamide,
N-([3R)-1-azabicyclo[2.2.2]octan-3-yl)-1-(2,4-dichlorophenyl)-6-oxo-3-pyridinecarboxamide,
N-([3S)-1-azabicyclo[2.2.2]octan-3-yl)-1-(2,4-dichlorophenyl)-6-oxo-3-pyridinecarboxamide,
N-(1-azabicyclo[2.2.2]octan-3-yl)-1-(3-chloro-4-methoxyphenyl)-6-oxo-3-pyridinecarboxamide,
N-(1-azabicyclo[2.2.2]octan-3-yl)-1-(2-chloro-4-methylphenyl)-6-oxo-3-pyridinecarboxamide,
N-(1-azabicyclo[2.2.2]octan-3-yl)-1-(2,5-difluorophenyl)-6-oxo-3-pyridinecarboxamide,
N-(1-azabicyclo[2.2.2]octan-3-yl)-1-(3,5-dichlorophenyl)-6-oxo-3-pyridinecarboxamide,
N-(1-azabicyclo[2.2.2]octan-3-yl)-1-(2,4-dimethylphenyl)-6-oxo-3-pyridinecarboxamide,
N-(1-azabicyclo[2.2.2]octan-3-yl)-1-(2-chloro-4-methylphenyl)-6-oxo-3-pyridinecarboxamide,
N-(1-azabicyclo[2.2.2]octan-3-yl)-1-(2,4-difluorophenyl)-6-oxo-3-pyridinecarboxamide,
N-(1-azabicyclo[2.2.2]octan-3-yl)-1-(2-chloro-5-methylphenyl)-6-oxo-3-pyridinecarboxamide,
N-(1-azabicyclo[2.2.2]octan-3-yl)-1-(4-tert-butyl-2-chlorophenyl)-6-oxo-3-pyridinecarboxamide,
N-(1-azabicyclo[2.2.2]octan-3-yl)-1-(2-chloro-4-fluorophenyl)-6-oxo-3-pyridinecarboxamide,
N-(1-azabicyclo[2.2.2]octan-3-yl)-1-(4-chloro-2-fluorophenyl)-6-oxo-3-pyridinecarboxamide,
N-(1-azabicyclo[2.2.2]octan-3-yl)-1-(3,4-dimethoxyphenyl)-6-oxo-3-pyridinecarboxamide,
N-(1-azabicyclo[2.2.2]octan-3-yl)-1-(3,4-dichlorophenyl)-6-oxo-3-pyridinecarboxamide,
N-(1-azabicyclo[2.2.2]octan-3-yl)-1-(3,4-difluorophenyl)-6-oxo-3-pyridinecarboxamide,
N-(1-azabicyclo[2.2.2]octan-3-yl)-1-(4-chloro-3-methylphenyl)-6-oxo-3-pyridinecarboxamide,
N-(1-azabicyclo[2.2.2]octan-3-yl)-1-(3,5-difluorophenyl)-6-oxo-3-pyridinecarboxamide,
N-(1-azabicyclo[2.2.2]octan-3-yl)-1-(4-fluoro-2-methylphenyl)-6-oxo-3-pyridinecarboxamide,
N-(1-azabicyclo[2.2.2]octan-3-yl)-1-(2,5-dimethoxyphenyl)-6-oxo-3-pyridinecarboxamide,
N-(1-azabicyclo[2.2.2]octan-3-yl)-1-(2,3-dichlorophenyl)-6-oxo-3-pyridinecarboxamide,
N-(1-azabicyclo[2.2.2]octan-3-yl)-1-(3-chloro-2-methoxyphenyl)-6-oxo-3-pyridinecarboxamide,
N-(1-azabicyclo[2.2.2]octan-3-yl)-1-(3-fluoro-4-methoxyphenyl)-6-oxo-3-pyridinecarboxamide,
N-(1-azabicyclo[2.2.2]octan-3-yl)-1-(2,4-dimethoxyphenyl)-6-oxo-3-pyridinecarboxamide,
N-(1-azabicyclo[2.2.2]octan-3-yl)-1-(3-chloro-4-fluorophenyl)-6-oxo-3-pyridinecarboxamide,
N-(1-azabicyclo[2.2.2]octan-3-yl)-1-(4-chloro-3-methoxyphenyl)-6-oxo-3-pyridinecarboxamide,
N-(1-azabicyclo[2.2.2]octan-3-yl)-1-(2-methoxy-5-methylphenyl)-6-oxo-3-pyridinecarboxamide,
N-(1-azabicyclo[2.2.2]octan-3-yl)-1-(4-chloro-2-methylphenyl)-6-oxo-3-pyridinecarboxamide,
N-(1-azabicyclo[2.2.2]octan-3-yl)-1-(4-methoxy-2-methylphenyl)-6-oxo-3-pyridinecarboxamide,
N-(1-azabicyclo[2.2.2]octan-3-yl)-1-[4-chloro-3-(trifluoromethyl)phenyl]-6-oxo-3-pyridinecarboxamide,
N-(1-azabicyclo[2.2.2]octan-3-yl)-1-(5-chloro-2-methoxyphenyl)-6-oxo-3-pyridinecarboxamide,
N-(1-azabicyclo[2.2.2]octan-3-yl)-1-[2-chloro-4-(trifluoromethoxy)phenyl]-6-oxo-3-pyridinecarboxamide,
N-(1-azabicyclo[2.2.2]octan-3-yl)-1-(4-chloro-3-fluorophenyl)-6-oxo-3-pyridinecarboxamide,
N-(1-azabicyclo[2.2.2]octan-3-yl)-1-(2,4,5-trimethoxyphenyl)-6-oxo-3-pyridinecarboxamide,
N-(1-azabicyclo[2.2.2]octan-3-yl)-1-(2,4,5-trichlorophenyl)-6-oxo-3-pyridinecarboxamide,
N-(1-azabicyclo[2.2.2]octan-3-yl)-1-(3,4,5-trifluorophenyl)-6-oxo-3-pyridinecarboxamide,
N-(1-azabicyclo[2.2.2]octan-3-yl)-6-oxo-1-(3-phenylphenyl)-3-pyridinecarboxamide,
N-(1-azabicyclo[2.2.2]octan-3-yl)-6-oxo-1-(2-phenylmethoxyphenyl)-3-pyridinecarboxamide,
N-(1-azabicyclo[2.2.2]octan-3-yl)-6-oxo-1-(2-phenylphenyl)-3-pyridinecarboxamide,
N-(1-azabicyclo[2.2.2]octan-3-yl)-1-(4-phenylphenyl)-6-oxo-3-pyridinecarboxamide,
N-(1-azabicyclo[2.2.2]octan-3-yl)-1-(2-methoxy-5-phenylphenyl)-6-oxo-3-pyridinecarboxamide,
N-(1-azabicyclo[2.2.2]octan-3-yl)-1-[4-(4-chlorophenyl)phenyl]-6-oxo-3-pyridinecarboxamide,
N-(1-azabicyclo[2.2.2]octan-3-yl)-1-[4-(4-methoxyphenyl)phenyl]-6-oxo-3-pyridinecarboxamide,
N-(1-azabicyclo[2.2.2]octan-3-yl)-1-[4-(4-methylphenyl)phenyl]-6-oxo-3-pyridinecarboxamide,
N-(1-azabicyclo[2.2.2]octan-3-yl)-1-(2-chloro-4-phenylphenyl)-6-oxo-3-pyridinecarboxamide,
N-(1-azabicyclo[2.2.2]octan-3-yl)-1-[4-(4-chlorophenoxy)phenyl]-6-oxo-3-pyridinecarboxamide,
N-(1-azabicyclo[2.2.2]octan-3-yl)-1-[4-(4-methylphenoxy)phenyl]-6-oxo-3-pyridinecarboxamide,
N-(1-azabicyclo[2.2.2]octan-3-yl)-6-oxo-1-(4-phenoxyphenyl)-3-pyridinecarboxamide,
N-(1-azabicyclo[2.2.2]octan-3-yl)-6-oxo-1-(2-phenoxyphenyl)-3-pyridinecarboxamide,
N-(1-azabicyclo[2.2.2]octan-3-yl)-1-(4-ethynylphenyl)-6-oxo-3-pyridinecarboxamide,
N-(1-azabicyclo[2.2.2]octan-3-yl)-1-[4-(methylthio)phenyl]-6-oxo-3-pyridinecarboxamide,
N-(1-azabicyclo[2.2.2]octan-3-yl)-1-[2-(methylthio)phenyl]-6-oxo-3-pyridinecarboxamide,
N-([3R)-1-azabicyclo[2.2.2]octan-3-yl]-1-[2-(methylthio)phenyl]-6-oxo-3-pyridinecarboxamide,
N-([3S)-1-azabicyclo[2.2.2]octan-3-yl]-1-[2-(methylthio)phenyl]-6-oxo-3-pyridinecarboxamide,
N-(1-azabicyclo[2.2.2]octan-3-yl)-1-[2-(ethylthio)phenyl]-6-oxo-3-pyridinecarboxamide,
N-(1-azabicyclo[2.2.2]octan-3-yl)-6-oxo-1-[2-(propan-2-ylthio)phenyl]-3-pyridinecarboxamide,
N-(1-azabicyclo[2.2.2]octan-3-yl)-6-oxo-1-[2-(phenylmethylthio)phenyl]-3-pyridinecarboxamide,
N-(1-azabicyclo[2.2.2]octan-3-yl)-1-[2-(methylthio)-5-(trifluoromethyl)phenyl]-6-oxo-3-pyridinecarboxamide,
N-(1-azabicyclo[2.2.2]octan-3-yl)-1-[4-methoxy-2-(methylthio)phenyl]-6-oxo-3-pyridinecarboxamide,
N-(1-azabicyclo[2.2.2]octan-3-yl)-1-[2-(ethylthio)-4-methoxyphenyl]-6-oxo-3-pyridinecarboxamide,
N-(1-azabicyclo[2.2.2]octan-3-yl)-1-[4-chloro-2-(methylthio)phenyl]-6-oxo-3-pyridinecarboxamide,
N-([3R)-1-azabicyclo[2.2.2]octan-3-yl]-1-[4-chloro-2-(methylthio)phenyl]-6-oxo-3-pyridinecarboxamide, N-([3S]-1-azabicyclo[2.2.2]octan-3-yl]-1-[4-chloro-2-(methylthio)phenyl]-6-oxo-3-pyridinecarboxamide,
N-(1-azabicyclo[2.2.2]octan-3-yl)-1-[4-methyl-2-(methylthio)phenyl]-6-oxo-3-pyridinecarboxamide,
N-(1-azabicyclo[2.2.2]octan-3-yl]-1-[4-methyl-2-(methylthio)phenyl]-6-oxo-3-pyridinecarboxamide,
N-[(3S)-1-azabicyclo[2.2.2]octan-3-yl]-1-[4-methyl-2-(methylthio)phenyl]-6-oxo-3-pyridinecarboxamide,
N-(1-azabicyclo[2.2.2]octan-3-yl)-1-[4-tert-butyl-2-(methylthio)phenyl]-6-oxo-3-pyridinecarboxamide,
N-(1-azabicyclo[2.2.2]octan-3-yl)-1-[4-chloro-2-(propan-2-ylthio)phenyl]-6-oxo-3-pyridinecarboxamide,
N-(1-azabicyclo[2.2.2]octan-3-yl)-1-[2-(methylthio)-4-propylphenyl]-6-oxo-3-pyridinecarboxamide,
N-(1-azabicyclo[2.2.2]octan-3-yl)-6-oxo-1-[2-(phenylthio)phenyl]-3-pyridinecarboxamide,
N-(1-azabicyclo[2.2.2]octan-3-yl)-1-[2-(methylthio)-4-propan-2-ylphenyl]-6-oxo-3-pyridinecarboxamide,
N-(1-azabicyclo[2.2.2]octan-3-yl)-1-[4-chloro-2-(ethylthio)phenyl]-6-oxo-3-pyridinecarboxamide,
N-(1-azabicyclo[2.2.2]octan-3-yl)-1-[4-ethyl-2-(methylthio)phenyl]-6-oxo-3-pyridinecarboxamide,
N-(1-azabicyclo[2.2.2]octan-3-yl)-1-[4-cyclohexyl-2-(methylthio)phenyl]-6-oxo-3-pyridinecarboxamide,
N-(1-azabicyclo[2.2.2]octan-3-yl)-1-(2-methylsulfonylphenyl)-6-oxo-3-pyridinecarboxamide,
N-(1-azabicyclo[2.2.2]octan-3-yl)-1-(4-methylsulfonylphenyl)-6-oxo-3-pyridinecarboxamide,
N-(1-azabicyclo[2.2.2]octan-3-yl)-1-(1-naphthalenyl)-6-oxo-3-pyridinecarboxamide,
N-(1-azabicyclo[2.2.2]octan-3-yl)-1-(2-naphthalenyl)-6-oxo-3-pyridinecarboxamide,
N-(1-azabicyclo[2.2.2]octan-3-yl)-6-oxo-1-[2-(2-thiazolyl)phenyl]-3-pyridinecarboxamide,
N-(1-azabicyclo[2.2.2]octan-3-yl)-1-[4-chloro-2-(2-thiazolyl)phenyl]-6-oxo-3-pyridinecarboxamide,
N-(1-azabicyclo[2.2.2]octan-3-yl)-1-[2-(5-methyl-2-thiazolyl)phenyl]-6-oxo-3-pyridinecarboxamide,
N-(1-azabicyclo[2.2.2]octan-3-yl)-1-[2-(1,3-benzothiazole-2-yl)phenyl]-6-oxo-3-pyridinecarboxamide,
N-(1-azabicyclo[2.2.2]octan-3-yl)-1-[4-(5-methyl-2-thiophenyl)phenyl]-6-oxo-3-pyridinecarboxamide,
N-(1-azabicyclo[2.2.2]octan-3-yl)-1-[2-chloro-4-(5-methyl-2-thiophenyl)phenyl]-6-oxo-3-pyridinecarboxamide,
N-(1-azabicyclo[2.2.2]octan-3-yl)-6-oxo-1-(2-thiophene-2-ylphenyl)-3-pyridinecarboxamide,
N-(1-azabicyclo[2.2.2]octan-3-yl)-1-[2-(5-methyl-2-thiophenyl)phenyl]-6-oxo-3-pyridinecarboxamide,
N-(1-azabicyclo[2.2.2]octan-3-yl)-1-[3-(2-methyl-4-thiazolyl)phenyl]-6-oxo-3-pyridinecarboxamide,
N-(1-azabicyclo[2.2.2]octan-3-yl)-1-[4-dimethylaminophenyl]-6-oxo-3-pyridinecarboxamide,
N-(1-azabicyclo[2.2.2]octan-3-yl)-1-{4-[(methyl-prop-2-ynyl-amino)-methyl]-phenyl}-6-oxo-3-pyridinecarboxamide,
(1-azabicyclo[2.2.2]octan-3-yl)-6-oxo-1-phenyl-3-pyridinecarboxylate,
(1-azabicyclo[2.2.2]octan-3-yl)-1-(2,4-dichlorophenyl)-6-oxo-3-pyridinecarboxylate,
N-(1-azabicyclo[2.2.2]octan-3-yl)-2-oxo-1-phenyl-3-pyridinecarboxamide,
N-(1-azabicyclo[2.2.2]octan-3-yl)-1-(4-methoxyphenyl)-2-oxo-3-pyridinecarboxamide,
N-(1-azabicyclo[2.2.2]octan-3-yl)-1-(4-chlorophenyl)-2-oxo-3-pyridinecarboxamide,
N-(1-azabicyclo[2.2.2]octan-3-yl)-2-oxo-1-[4-(trifluoromethyl)phenyl]-3-pyridinecarboxamide, and
N-(1-azabicyclo[2.2.2]octan-3-yl)-1-(4-tert-butylphenyl)-2-oxo-3-pyridinecarboxamide.

8. The compound of claim 1 or a pharmaceutically acceptable salt, solvate or hydrate thereof, wherein the compound is selected from the group consisting of:
N-(1-azabicyclo[2.2.2]octan-3-yl)-1-(4-chlorophenyl)-6-oxo-3-pyridinecarboxamide,
N-([3R)-1-azabicyclo[2.2.2]octan-3-yl]-1-(4-chlorophenyl)-6-oxopyridine-3-carboxamide,
N-(1-azabicyclo[2.2.2]octan-3-yl)-1-(2,4-dichlorophenyl)-6-oxo-3-pyridinecarboxamide,
N-([3R)-1-azabicyclo[2.2.2]octan-3-yl]-1-(2,4-dichlorophenyl)-6-oxo-3-pyridinecarboxamide,
N-([3S)-1-azabicyclo[2.2.2]octan-3-yl]-1-(2,4-dichlorophenyl)-6-oxo-3-pyridinecarboxamide,
N-(1-azabicyclo[2.2.2]octan-3-yl)-1-(2-chloro-4-methylphenyl)-6-oxo-3-pyridinecarboxamide,
N-(1-azabicyclo[2.2.2]octan-3-yl)-1-(4-phenylphenyl)-6-oxo-3-pyridinecarboxamide,
N-(1-azabicyclo[2.2.2]octan-3-yl)-1-[2-(methylthio)phenyl]-6-oxo-3-pyridinecarboxamide,
N-(1-azabicyclo[2.2.2]octan-3-yl)-1-[4-methoxy-2-(methylthio)phenyl]-6-oxo-3-pyridinecarboxamide,
N-(1-azabicyclo[2.2.2]octan-3-yl)-1-[4-chloro-2-(methylthio)phenyl]-6-oxo-3-pyridinecarboxamide,
N-(1-azabicyclo[2.2.2]octan-3-yl)-1-[4-methyl-2-(methylthio)phenyl]-6-oxo-3-pyridinecarboxamide,
N-([3S)-1-azabicyclo[2.2.2]octan-3-yl]-1-[4-methyl-2-(methylthio)phenyl]-6-oxo-3-pyridinecarboxamide,
N-(1-azabicyclo[2.2.2]octan-3-yl)-6-oxo-1-[2-(2-thiazolyl)phenyl]-3-pyridinecarboxamide,
N-(1-azabicyclo[2.2.2]octan-3-yl)-1-[4-chloro-2-(2-thiazolyl)phenyl]-6-oxo-3-pyridinecarboxamide, and
N-(1-azabicyclo[2.2.2]octan-3-yl)-1-[2-chloro-4-(5-methyl-2-thiophenyl)phenyl]-6-oxo-3-pyridinecarboxamide.

9. The compound of claim 1 or a pharmaceutically acceptable salt, solvate or hydrate thereof, wherein the compound is selected from the group consisting of:
N-[(3R)-1-azabicyclo[2.2.2]octan-3-yl]-1-(4-chlorophenyl)-6-oxopyridine-3-carboxamide,
N-[(3S)-1-azabicyclo[2.2.2]octan-3-yl]-1-(4-chlorophenyl)-6-oxopyridine-3-carboxamide,
N-([3R)-1-azabicyclo[2.2.2]octan-3-yl]-1-(2,4-dichlorophenyl)-6-oxo-3-pyridinecarboxamide,
N-([3S)-1-azabicyclo[2.2.2]octan-3-yl]-1-(2,4-dichlorophenyl)-6-oxo-3-pyridinecarboxamide,
N-([3R)-1-azabicyclo[2.2.2]octan-3-yl]-1-[2-(methylthio)phenyl]-6-oxo-3-pyridinecarboxamide,
N-([3S)-1-azabicyclo[2.2.2]octan-3-yl]-1-[2-(methylthio)phenyl]-6-oxo-3-pyridinecarboxamide,
N-([3R)-1-azabicyclo[2.2.2]octan-3-yl]-1-[4-chloro-2-(methylthio)phenyl]-6-oxo-3-pyridinecarboxamide,
N-([3S)-1-azabicyclo[2.2.2]octan-3-yl]-1-[4-chloro-2-(methylthio)phenyl]-6-oxo-3-pyridinecarboxamide,
N-([3R)-1-azabicyclo[2.2.2]octan-3-yl]-1-[4-methyl-2-(methylthio)phenyl]-6-oxo-3-pyridinecarboxamide, and
N-([3S)-1-azabicyclo[2.2.2]octan-3-yl]-1-[4-methyl-2-(methylthio)phenyl]-6-oxo-3-pyridinecarboxamide.

10. The compound of claim 1 or a pharmaceutically acceptable salt, solvate or hydrate thereof, wherein the compound is
N-(1-azabicyclo[2.2.2]octan-3-yl)-1-(2,4-dichlorophenyl)-6-oxo-3-pyridinecarboxamide, N-([3R)-1-azabicyclo[2.2.2]octan-3-yl)-1-(2,4-dichlorophenyl)-6-oxo-3-pyridinecarboxamide, or N-([3S)-1-azabicyclo[2.2.2]octan-3-yl)-1-(2,4-dichlorophenyl)-6-oxo-3-pyridinecarboxamide.

11. The compound of claim 1 or a pharmaceutically acceptable salt, solvate or hydrate thereof, wherein the compound is N-[(3R)-1-azabicyclo[2.2.2]octan-3-yl)-1-(2,4-dichlorophenyl)-6-oxo-3-pyridinecarboxamide.

12. A pharmaceutical composition comprising the compound of claim 1 or a pharmaceutically acceptable salt, solvate or hydrate thereof and a pharmaceutically acceptable carrier.

13. The pharmaceutical composition of claim 12, which is an oral formulation.

* * * * *